US012588993B2

(12) United States Patent
    Ekvall et al.

(10) Patent No.:   US 12,588,993 B2
(45) Date of Patent:    Mar. 31, 2026

(54) DEVICES AND METHODS FOR DELIVERING A PROSTHETIC HEART VALVE USING SUPRA-ANNULAR SUPPORT

(71) Applicant: VDyne, Inc., Maple Grove, MN (US)

(72) Inventors: Craig Ekvall, East Bethel, MN (US); Robert Vidlund, Forest Lake, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 18/410,230

(22) Filed: Jan. 11, 2024

(65) Prior Publication Data

US 2024/0138983 A1    May 2, 2024

Related U.S. Application Data

(63) Continuation of application No. PCT/US2023/076845, filed on Oct. 13, 2023.
            (Continued)

(51) Int. Cl.
    *A61F 2/24*       (2006.01)
(52) U.S. Cl.
    CPC ............ *A61F 2/2436* (2013.01); *A61F 2/243* (2013.01); *A61F 2220/0025* (2013.01)
(58) Field of Classification Search
    CPC .... A61F 2/2427; A61F 2/2436; A61F 2/2439; A61F 2/2433; A61F 2/2418
    See application file for complete search history.

(56) References Cited

U.S. PATENT DOCUMENTS 3,744,060 A    7/1973   Bellhouse et al.
4,079,468 A    3/1978   Liotta et al.
          (Continued)

FOREIGN PATENT DOCUMENTS

AU    2006203686 A1   9/2006
AU    2009219415 A1   9/2009
          (Continued)

OTHER PUBLICATIONS

Extended European Search Report for European Application No. 19863898.3, mailed Apr. 29, 2022, 13 pages.
          (Continued)

*Primary Examiner* — Alvin J Stewart
(74) *Attorney, Agent, or Firm* — COOLEY LLP

(57)       ABSTRACT

A delivery system includes a delivery sheath with a control device and at least one supra-annular support being movable through a lumen of the delivery sheath. The control device includes a connection member coupled to a distal end of a control catheter. The connection member is configured to removably couple to the prosthetic valve at a proximal position along a supra-annular portion of the prosthetic valve. The control device is operable to advance the prosthetic valve in a compressed configuration through the delivery sheath and to at least partially deploy the prosthetic valve in an expanded configuration into a native valve annulus. The supra-annular support(s) is/are removably coupleable at one or more positions along the supra-annular portion of the prosthetic valve and is/are configured to stabilize or actuate at least a portion of the prosthetic valve relative to an annular plane of a native heart valve during deployment.

30 Claims, 17 Drawing Sheets

Related U.S. Application Data

(60) Provisional application No. 63/510,699, filed on Jun. 28, 2023, provisional application No. 63/505,966, filed on Jun. 2, 2023, provisional application No. 63/379,569, filed on Oct. 14, 2022.

(56) References Cited

U.S. PATENT DOCUMENTS

| | | | |
|---|---|---|---|
| 5,397,351 | A | 3/1995 | Pavcnik et al. |
| 5,509,428 | A | 4/1996 | Dunlop |
| 5,554,185 | A | 9/1996 | Block et al. |
| 5,800,531 | A | 9/1998 | Cosgrove et al. |
| 5,906,642 | A | 5/1999 | Caudillo et al. |
| 6,006,134 | A | 12/1999 | Hill et al. |
| 6,197,013 | B1 | 3/2001 | Reed et al. |
| 6,290,719 | B1 | 9/2001 | Garberoglio |
| 6,312,464 | B1 | 11/2001 | Navia |
| 6,449,507 | B1 | 9/2002 | Hill et al. |
| 6,458,153 | B1 | 10/2002 | Bailey et al. |
| 6,532,388 | B1 | 3/2003 | Hill et al. |
| 6,582,467 | B1 | 6/2003 | Teitelbaum et al. |
| 6,628,987 | B1 | 9/2003 | Hill et al. |
| 6,669,724 | B2 | 12/2003 | Park et al. |
| 6,702,845 | B1 | 3/2004 | Cully et al. |
| 6,718,208 | B2 | 4/2004 | Hill et al. |
| 6,769,434 | B2 | 8/2004 | Liddicoat et al. |
| 6,890,330 | B2 | 5/2005 | Streeter et al. |
| 6,896,690 | B1 | 5/2005 | Lambrecht et al. |
| 6,904,318 | B2 | 6/2005 | Hill et al. |
| 6,929,653 | B2 | 8/2005 | Strecter |
| 7,074,189 | B1 | 7/2006 | Montegrande |
| 7,125,418 | B2 | 10/2006 | Duran et al. |
| 7,175,660 | B2 | 2/2007 | Cartledge et al. |
| 7,201,761 | B2 | 4/2007 | Woolfson et al. |
| 7,225,019 | B2 | 5/2007 | Jahns et al. |
| 7,269,457 | B2 | 9/2007 | Shafer et al. |
| 7,331,991 | B2 | 2/2008 | Kheradvar et al. |
| 7,361,189 | B2 | 4/2008 | Case et al. |
| 7,374,571 | B2 | 5/2008 | Pease et al. |
| 7,442,204 | B2 | 10/2008 | Schwammenthal et al. |
| 7,449,027 | B2 | 11/2008 | Hunt et al. |
| 7,621,948 | B2 | 11/2009 | Herrmann et al. |
| 7,648,527 | B2 | 1/2010 | Agnew |
| 7,717,952 | B2 | 5/2010 | Case et al. |
| 7,749,245 | B2 | 7/2010 | Cohn et al. |
| 7,753,949 | B2 | 7/2010 | Lamphere et al. |
| 7,811,316 | B2 | 10/2010 | Kalmann et al. |
| 7,828,840 | B2 | 11/2010 | Biggs et al. |
| 7,846,199 | B2 | 12/2010 | Paul, Jr. et al. |
| 8,303,648 | B2 | 11/2012 | Grewe et al. |
| 8,366,768 | B2 | 2/2013 | Zhang |
| 8,491,650 | B2 | 7/2013 | Wiemeyer et al. |
| 8,568,474 | B2 | 10/2013 | Yeung et al. |
| 8,628,571 | B1 | 1/2014 | Hacohen et al. |
| 8,641,752 | B1 | 2/2014 | Holm et al. |
| 8,696,743 | B2 | 4/2014 | Holecek et al. |
| 8,728,153 | B2 | 5/2014 | Bishop et al. |
| 8,758,395 | B2 | 6/2014 | Kleshinski et al. |
| 8,846,390 | B2 | 9/2014 | Dove et al. |
| 8,876,892 | B2 | 11/2014 | Tran et al. |
| 8,900,295 | B2 | 12/2014 | Migliazza et al. |
| 8,915,958 | B2 | 12/2014 | Braido |
| 8,926,690 | B2 | 1/2015 | Kovalsky |
| 8,926,692 | B2 | 1/2015 | Dwork |
| 8,926,694 | B2 * | 1/2015 | Costello ............... A61F 2/2436 |
| | | | 623/2.11 |
| 8,940,044 | B2 | 1/2015 | Hammer et al. |
| 8,956,404 | B2 | 2/2015 | Bortlein et al. |
| 8,986,370 | B2 | 3/2015 | Annest |
| 8,998,982 | B2 | 4/2015 | Richter et al. |
| 9,011,524 | B2 | 4/2015 | Eberhardt |
| 9,017,399 | B2 | 4/2015 | Gross et al. |
| 9,050,188 | B2 | 6/2015 | Schweich, Jr. et al. |
| 9,072,604 | B1 | 7/2015 | Melnick et al. |
| 9,119,714 | B2 | 9/2015 | Shandas et al. |
| 9,216,076 | B2 | 12/2015 | Mitra et al. |
| 9,232,995 | B2 | 1/2016 | Kovalsky et al. |
| 9,241,792 | B2 | 1/2016 | Benichou et al. |
| 9,248,016 | B2 | 2/2016 | Oba et al. |
| 9,259,215 | B2 | 2/2016 | Chou et al. |
| 9,277,990 | B2 | 3/2016 | Klima et al. |
| 9,289,282 | B2 | 3/2016 | Olson et al. |
| 9,289,296 | B2 | 3/2016 | Braido et al. |
| 9,295,547 | B2 | 3/2016 | Costello et al. |
| 9,301,839 | B2 | 4/2016 | Stante et al. |
| 9,308,086 | B2 | 4/2016 | Ho |
| 9,339,367 | B2 | 5/2016 | Carpenter et al. |
| 9,370,418 | B2 | 6/2016 | Pintor et al. |
| 9,381,083 | B2 | 7/2016 | Costello |
| 9,387,075 | B2 | 7/2016 | Bortlein et al. |
| 9,393,111 | B2 | 7/2016 | Ma et al. |
| 9,402,720 | B2 | 8/2016 | Richter et al. |
| 9,414,915 | B2 | 8/2016 | Lombardi et al. |
| 9,433,500 | B2 | 9/2016 | Chau et al. |
| 9,440,054 | B2 | 9/2016 | Bishop et al. |
| 9,456,899 | B2 | 10/2016 | Yeung et al. |
| 9,468,525 | B2 | 10/2016 | Kovalsky |
| 9,474,604 | B2 | 10/2016 | Centola et al. |
| 9,486,306 | B2 | 11/2016 | Tegels et al. |
| 9,504,562 | B2 | 11/2016 | Richter et al. |
| 9,510,941 | B2 | 12/2016 | Bishop et al. |
| 9,526,613 | B2 | 12/2016 | Gross et al. |
| 9,554,902 | B2 | 1/2017 | Braido et al. |
| 9,579,196 | B2 | 2/2017 | Morriss et al. |
| 9,579,200 | B2 | 2/2017 | Lederman et al. |
| 9,597,181 | B2 | 3/2017 | Christianson et al. |
| 9,610,159 | B2 | 4/2017 | Christianson et al. |
| 9,615,925 | B2 | 4/2017 | Subramanian et al. |
| 9,629,719 | B2 | 4/2017 | Rothstein |
| 9,636,222 | B2 | 5/2017 | Oslund |
| 9,649,191 | B2 | 5/2017 | Savage et al. |
| 9,662,202 | B2 | 5/2017 | Quill et al. |
| 9,662,203 | B2 | 5/2017 | Sheahan et al. |
| 9,662,209 | B2 | 5/2017 | Gross et al. |
| 9,675,454 | B2 | 6/2017 | Vidlund et al. |
| 9,675,485 | B2 | 6/2017 | Essinger et al. |
| 9,687,343 | B2 | 6/2017 | Bortlein et al. |
| 9,707,076 | B2 | 7/2017 | Stack et al. |
| 9,713,530 | B2 | 7/2017 | Cabiri et al. |
| 9,750,607 | B2 | 9/2017 | Ganesan et al. |
| 9,763,778 | B2 | 9/2017 | Eidenschink et al. |
| 9,763,779 | B2 | 9/2017 | Bortlein et al. |
| 9,788,946 | B2 | 10/2017 | Bobo, Jr. et al. |
| 9,839,511 | B2 | 12/2017 | Ma et al. |
| 9,849,011 | B2 | 12/2017 | Zimmerman et al. |
| 9,855,384 | B2 | 1/2018 | Cohen et al. |
| 9,861,464 | B2 | 1/2018 | Azimpour et al. |
| 9,895,219 | B2 | 2/2018 | Costello |
| 9,901,330 | B2 | 2/2018 | Akpinar |
| 9,918,838 | B2 | 3/2018 | Ring |
| 9,943,409 | B2 | 4/2018 | Kim et al. |
| 9,949,825 | B2 | 4/2018 | Braido et al. |
| 9,968,444 | B2 | 5/2018 | Millwee et al. |
| 9,968,445 | B2 | 5/2018 | Kheradvar |
| 9,980,815 | B2 | 5/2018 | Nitzan et al. |
| 9,987,121 | B2 | 6/2018 | Blanzy |
| 10,010,411 | B2 | 7/2018 | Peter |
| 10,010,412 | B2 | 7/2018 | Taft et al. |
| 10,022,054 | B2 | 7/2018 | Najafi et al. |
| 10,022,222 | B2 | 7/2018 | Groothuis et al. |
| 10,022,223 | B2 | 7/2018 | Bruchman |
| 10,028,821 | B2 | 7/2018 | Centola et al. |
| 10,028,831 | B2 | 7/2018 | Morin et al. |
| 10,034,667 | B2 | 7/2018 | Morris et al. |
| 10,034,747 | B2 | 7/2018 | Harewood |
| 10,039,638 | B2 | 8/2018 | Bruchman et al. |
| 10,058,315 | B2 | 8/2018 | Rafiee et al. |
| 10,058,411 | B2 | 8/2018 | Fifer et al. |
| 10,058,421 | B2 | 8/2018 | Eberhardt et al. |
| 10,058,426 | B2 | 8/2018 | Barbarino |
| 10,064,405 | B2 | 9/2018 | Dale et al. |
| 10,080,653 | B2 | 9/2018 | Conklin et al. |
| 10,085,834 | B2 | 10/2018 | Benson et al. |
| 10,085,835 | B2 | 10/2018 | Thambar et al. |

(56)             References Cited

U.S. PATENT DOCUMENTS

| | | |
|---|---|---|
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 * | 6/2019 | Christianson ......... A61F 2/2409 |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,662 B2 | 11/2019 | Alkhatib |
| 10,485,976 B2 | 11/2019 | Streeter et al. |
| 10,517,718 B2 | 12/2019 | Richter et al. |
| 10,537,425 B2 | 1/2020 | Richter et al. |
| 10,595,994 B1 * | 3/2020 | Christianson ......... A61L 31/129 |
| 10,631,983 B1 * | 4/2020 | Christianson ......... A61F 2/2436 |
| 10,653,522 B1 * | 5/2020 | Vidlund ................ A61F 2/2433 |
| 10,653,523 B2 * | 5/2020 | Chambers ............... A61F 2/243 |
| 10,758,346 B1 * | 9/2020 | Christianson ......... A61F 2/2439 |
| 10,761,511 B2 | 9/2020 | Chen et al. |
| 10,779,937 B2 | 9/2020 | Vidlund et al. |
| 11,071,627 B2 * | 7/2021 | Saikrishnan ............ A61F 2/243 |
| 11,076,956 B2 * | 8/2021 | Christianson ......... A61F 2/2418 |
| 11,109,969 B2 * | 9/2021 | Vidlund ................ A61F 2/2466 |
| 11,166,814 B2 * | 11/2021 | Vidlund, I ............ A61F 2/9522 |
| 11,173,027 B2 * | 11/2021 | Christianson ......... A61F 2/2436 |
| 11,179,239 B2 * | 11/2021 | Vidlund ................ A61F 2/2418 |
| 11,185,409 B2 * | 11/2021 | Christianson ......... A61F 2/2418 |
| 11,202,706 B2 * | 12/2021 | Christianson ............. A61F 2/24 |
| 11,234,812 B2 | 2/2022 | Green et al. |
| 11,234,813 B2 * | 2/2022 | Perrin ................... A61F 2/2433 |
| 11,253,359 B2 * | 2/2022 | Vidlund ................ A61F 2/2436 |
| 11,273,032 B2 * | 3/2022 | Christianson ......... A61F 2/2427 |
| 11,273,033 B2 | 3/2022 | Christianson et al. |
| 11,278,437 B2 * | 3/2022 | Christianson ............. A61F 2/95 |
| 11,298,227 B2 * | 4/2022 | Vidlund ................ A61F 2/2412 |
| 11,331,186 B2 * | 5/2022 | Christianson ......... A61F 2/2427 |
| 11,337,807 B2 * | 5/2022 | Christianson ......... A61F 2/2415 |
| 11,344,412 B2 * | 5/2022 | Vidlund ................ A61F 2/243 |
| 11,344,413 B2 * | 5/2022 | Christianson ......... A61F 2/2436 |
| 11,712,335 B2 * | 8/2023 | Christianson ......... A61F 2/2418 |
| | | 623/2.11 |
| 11,717,399 B2 | 8/2023 | Armer et al. |
| 11,786,366 B2 | 10/2023 | Vidlund et al. |
| 12,138,158 B2 | 11/2024 | Vidlund et al. |
| 12,144,731 B2 | 11/2024 | Vidlund et al. |
| 12,150,852 B2 | 11/2024 | Vidlund et al. |
| 12,186,187 B2 | 1/2025 | Christianson et al. |
| 12,310,850 B2 | 5/2025 | Christianson et al. |
| 12,318,286 B2 | 6/2025 | Christianson |
| 12,324,737 B2 | 6/2025 | Vidlund et al. |
| 12,343,256 B2 | 7/2025 | Christianson et al. |
| 2002/0138138 A1 | 9/2002 | Yang |
| 2002/0183827 A1 | 12/2002 | Derus et al. |
| 2003/0040772 A1 | 2/2003 | Hyodoh et al. |
| 2003/0040808 A1 | 2/2003 | Stack et al. |
| 2003/0055495 A1 | 3/2003 | Pease et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0117009 A1 | 6/2004 | Cali et al. |
| 2004/0167619 A1 | 8/2004 | Case et al. |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0203614 A1 | 9/2005 | Forster et al. |
| 2005/0228472 A1 | 10/2005 | Case et al. |
| 2005/0228495 A1 | 10/2005 | Macoviak |
| 2006/0015167 A1 | 1/2006 | Armstrong et al. |
| 2006/0173524 A1 * | 8/2006 | Salahieh ............... A61F 2/2418 |
| | | 623/1.11 |
| 2006/0190075 A1 | 8/2006 | Jordan et al. |
| 2006/0195180 A1 | 8/2006 | Kheradvar et al. |
| 2006/0195183 A1 | 8/2006 | Navia et al. |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0073387 A1 | 3/2007 | Forster et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0048656 A1 | 2/2009 | Wen |
| 2009/0054976 A1 | 2/2009 | Tuval et al. |
| 2009/0094189 A1 | 4/2009 | Stephens |
| 2009/0132035 A1 | 5/2009 | Roth et al. |
| 2009/0164003 A1 | 6/2009 | Kheradvar |
| 2009/0192586 A1 | 7/2009 | Tabor et al. |
| 2009/0192601 A1 | 7/2009 | Rafiee et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0016894 A1 | 1/2010 | Houard et al. |
| 2010/0049294 A1 | 2/2010 | Zukowski et al. |
| 2010/0049313 A1 | 2/2010 | Alon et al. |
| 2010/0087918 A1 | 4/2010 | Vesely et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |

(56) References Cited

U.S. PATENT DOCUMENTS

| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0185275 A1 | 7/2010 | Richter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1 | 6/2011 | Chau et al. |
| 2011/0137399 A1 | 6/2011 | Chomas et al. |
| 2011/0160836 A1 | 6/2011 | Behan |
| 2011/0172764 A1 | 7/2011 | Badhwar |
| 2011/0172784 A1 | 7/2011 | Richter et al. |
| 2011/0208298 A1 | 8/2011 | Tuval et al. |
| 2011/0224785 A1 | 9/2011 | Hacohen |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2011/0319989 A1 | 12/2011 | Lane et al. |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0035719 A1 | 2/2012 | Forster et al. |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHUGO |
| 2012/0310328 A1 | 12/2012 | Olson et al. |
| 2013/0035759 A1 | 2/2013 | Gross et al. |
| 2013/0046373 A1 | 2/2013 | Cartledge et al. |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0178931 A1 | 7/2013 | Fargahi |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1 | 11/2013 | McLean et al. |
| 2013/0310917 A1 | 11/2013 | Richter et al. |
| 2013/0325110 A1 | 12/2013 | Khalil et al. |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Biadillah et al. |
| 2014/0025164 A1 | 1/2014 | Montorfano et al. |
| 2014/0031924 A1 | 1/2014 | Bruchman et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0067037 A1* | 3/2014 | Fargahi ............... A61F 2/2439 |
| | | 623/1.12 |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0172077 A1 | 6/2014 | Bruchman et al. |
| 2014/0172083 A1 | 6/2014 | Bruchman et al. |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0249621 A1 | 9/2014 | Eidenschink |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0277563 A1 | 9/2014 | White |
| 2014/0288480 A1 | 9/2014 | Zimmerman et al. |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1* | 2/2015 | Costello ............... A61F 2/2436 |
| | | 623/2.11 |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119978 A1 | 4/2015 | Tegels et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173897 A1 | 6/2015 | Raanani et al. |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |

(56) References Cited

U.S. PATENT DOCUMENTS

| | | |
|---|---|---|
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0297381 A1 | 10/2015 | Essinger et al. |
| 2015/0305867 A1 | 10/2015 | Liu et al. |
| 2015/0313701 A1* | 11/2015 | Krahbichler ............... A61F 2/01 |
| | | 606/300 |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220363 A1 | 8/2016 | Peter |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235525 A1 | 8/2016 | Rothstein et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0302921 A1 | 10/2016 | Gosal et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056163 A1 | 3/2017 | Tayeb et al. |
| 2017/0056166 A1 | 3/2017 | Ratz et al. |
| 2017/0056171 A1 | 3/2017 | Cooper et al. |
| 2017/0071733 A1 | 3/2017 | Ghione |
| 2017/0071736 A1* | 3/2017 | Zhu ....................... A61F 2/2418 |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100236 A1 | 4/2017 | Robertson et al. |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143446 A1 | 5/2017 | Kölbel |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1* | 9/2017 | Racchini ............... A61F 2/2418 |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0319333 A1 | 11/2017 | Tegels et al. |
| 2017/0325943 A1 | 11/2017 | Robin et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1* | 12/2017 | Kheradvar ............ A61F 2/2436 |
| 2017/0360558 A1 | 12/2017 | Ma |
| 2017/0360561 A1 | 12/2017 | Bell et al. |
| 2018/0000586 A1* | 1/2018 | Ganesan ............... A61F 2/2409 |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042721 A1 | 2/2018 | Chambers |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071086 A1 | 3/2018 | Vesely |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0098847 A1 | 4/2018 | Tuseth et al. |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |

(56)                    References Cited

U.S. PATENT DOCUMENTS

| | | |
|---|---|---|
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133009 A1 | 5/2018 | Alon |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318071 A1 | 11/2018 | Lozonschi et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0333259 A1 | 11/2018 | Dibie |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008636 A1 | 1/2019 | Francis et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1* | 2/2019 | Cohen ................... A61F 2/2439 |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1* | 4/2019 | Barash ................. A61F 2/2415 |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0321171 A1 | 10/2019 | Morriss et al. |
| 2019/0365538 A1 | 12/2019 | Chambers et al. |
| 2019/0388219 A1 | 12/2019 | Lane et al. |
| 2020/0008941 A1 | 1/2020 | Stappenbeck et al. |
| 2020/0093589 A1* | 3/2020 | Christianson ......... A61F 2/2409 |
| 2020/0121452 A1* | 4/2020 | Saikrishnan ............ A61F 2/243 |
| 2020/0121458 A1* | 4/2020 | Vidlund ................ A61F 2/2418 |
| 2020/0179146 A1* | 6/2020 | Christianson ............. A61F 2/91 |
| 2020/0188097 A1* | 6/2020 | Perrin .................. A61F 2/2433 |
| 2020/0237506 A1* | 7/2020 | Christianson ......... A61F 2/2439 |
| 2020/0289259 A1 | 9/2020 | Christianson et al. |
| 2020/0289263 A1* | 9/2020 | Christianson ......... A61F 2/2433 |
| 2021/0000592 A1* | 1/2021 | Christianson ......... A61F 2/2427 |
| 2021/0137677 A1* | 5/2021 | Christianson ......... A61F 2/2436 |
| 2021/0154010 A1 | 5/2021 | Schneider et al. |
| 2021/0154011 A1* | 5/2021 | Christianson ......... A61F 2/2418 |
| 2021/0186693 A1* | 6/2021 | Vidlund, I ............ A61F 2/2433 |
| 2021/0220126 A1* | 7/2021 | Perrin .................. A61F 2/2433 |
| 2021/0220127 A1* | 7/2021 | Vidlund ................ A61F 2/2439 |
| 2021/0220134 A1* | 7/2021 | Christianson ......... A61F 2/2415 |
| 2021/0228349 A1* | 7/2021 | Vidlund ................ A61F 2/2457 |
| 2021/0236280 A1* | 8/2021 | Christianson ............. A61F 2/24 |
| 2021/0244533 A1 | 8/2021 | Vidlund et al. |
| 2021/0244535 A1* | 8/2021 | Iyer ...................... A61F 2/2418 |
| 2021/0244536 A1* | 8/2021 | Christianson .......... B33Y 80/00 |
| 2021/0290381 A1 | 9/2021 | Vidlund et al. |
| 2021/0290385 A1* | 9/2021 | Christianson ......... A61F 2/2433 |
| 2021/0315694 A1* | 10/2021 | Vidlund ............. A61N 1/37512 |
| 2021/0330459 A1* | 10/2021 | Christianson ......... A61F 2/2418 |

(56)  References Cited

U.S. PATENT DOCUMENTS

| | | | |
|---|---|---|---|
| 2021/0353412 A1 | 11/2021 | Christianson et al. | |
| 2021/0401572 A1* | 12/2021 | Nasr | A61F 2/2436 |
| 2022/0000614 A1 | 1/2022 | Vidlund et al. | |
| 2022/0087815 A1 | 3/2022 | Bernshtein et al. | |
| 2022/0096226 A1 | 3/2022 | Christianson et al. | |
| 2022/0160504 A1 | 5/2022 | Vidlund et al. | |
| 2022/0249228 A1 | 8/2022 | Vidlund et al. | |
| 2022/0280292 A1 | 9/2022 | Vidlund et al. | |
| 2022/0280296 A1 | 9/2022 | Christianson et al. | |
| 2022/0296369 A1* | 9/2022 | Kheradvar | A61F 2/2427 |
| 2022/0323212 A1 | 10/2022 | Vidlund et al. | |
| 2022/0338978 A1* | 10/2022 | Yushtein | A61F 2/2418 |
| 2022/0370198 A1* | 11/2022 | Nir | A61F 2/2415 |
| 2022/0378410 A1 | 12/2022 | Hacohen et al. | |
| 2022/0387174 A1* | 12/2022 | Schwarcz | A61F 2/2439 |
| 2022/0395370 A1 | 12/2022 | Vidlund et al. | |
| 2022/0409369 A1 | 12/2022 | Christianson et al. | |
| 2023/0157816 A1 | 5/2023 | Perrin | |
| 2023/0172710 A1* | 6/2023 | Nir | A61F 2/2436 623/2.11 |
| 2023/0190463 A1* | 6/2023 | Nir | A61F 2/2439 623/2.11 |
| 2023/0200990 A1* | 6/2023 | Chen | A61F 2/2418 623/2.11 |
| 2023/0263630 A1* | 8/2023 | Saar | A61F 2/2436 623/2.11 |
| 2023/0338140 A1* | 10/2023 | Cartledge | A61F 2/2436 |
| 2024/0074855 A1* | 3/2024 | Atias | A61F 2/2436 |
| 2024/0148496 A1 | 5/2024 | Christianson | |
| 2024/0148497 A1* | 5/2024 | Bukin | A61F 2/2433 |
| 2024/0225828 A1 | 7/2024 | Vidlund et al. | |
| 2025/0064585 A1 | 2/2025 | Vidlund et al. | |
| 2025/0073025 A1 | 3/2025 | Vidlund et al. | |
| 2025/0073028 A1 | 3/2025 | Vidlund et al. | |
| 2025/0073031 A1 | 3/2025 | Christianson et al. | |
| 2025/0255718 A1 | 8/2025 | Christianson et al. | |

FOREIGN PATENT DOCUMENTS

| | | | |
|---|---|---|---|
| AU | 2011236036 A1 | 11/2011 | |
| AU | 2011238752 A1 | 10/2012 | |
| AU | 2011240940 A1 | 10/2012 | |
| AU | 2012272855 A1 | 1/2014 | |
| AU | 2011248657 B2 | 12/2014 | |
| AU | 2016228261 A1 | 4/2017 | |
| AU | 2017210659 A1 | 8/2017 | |
| AU | 2013245201 B2 | 10/2017 | |
| AU | 2014360294 B2 | 10/2017 | |
| AU | 2016249819 A1 | 11/2017 | |
| AU | 2016371525 A1 | 5/2018 | |
| AU | 2016366783 A1 | 6/2018 | |
| AU | 2017214672 B2 | 10/2018 | |
| AU | 2017285993 A1 | 1/2019 | |
| AU | 2014201920 B2 | 2/2019 | |
| AU | 2015411406 B2 | 2/2019 | |
| AU | 2019202290 A1 | 4/2019 | |
| AU | 2017388857 A1 | 8/2019 | |
| BR | PI0909379 B1 | 9/2019 | |
| CA | 2531528 A1 | 1/2005 | |
| CA | 2609800 A1 | 1/2007 | |
| CA | 2822636 A1 | 10/2008 | |
| CA | 2398948 C | 8/2009 | |
| CA | 2813419 A1 | 4/2012 | |
| CA | 2856088 A1 | 5/2013 | |
| CA | 2866315 A1 | 9/2013 | |
| CA | 2922123 A1 | 4/2015 | |
| CA | 2504258 C | 6/2015 | |
| CA | 2677648 C | 10/2015 | |
| CA | 2815331 C | 10/2015 | |
| CA | 2986584 A1 | 11/2015 | |
| CA | 2975294 A1 | 8/2016 | |
| CA | 2995603 A1 | 2/2017 | |
| CA | 2753853 C | 4/2017 | |
| CA | 2702615 C | 6/2017 | |
| CA | 2744395 C | 8/2017 | |
| CA | 3020238 A1 | 11/2017 | |
| CA | 3033666 A1 | 2/2018 | |
| CA | 3031572 A1 | 3/2018 | |
| CA | 3022641 A1 | 5/2018 | |
| CA | 3044062 A1 | 6/2018 | |
| CA | 3048893 A1 | 7/2018 | |
| CA | 3049792 A1 | 7/2018 | |
| CA | 3046693 A1 | 8/2018 | |
| CA | 2778944 C | 8/2019 | |
| CN | 2855366 Y | 1/2007 | |
| CN | 100584292 C | 1/2010 | |
| CN | 101677820 A | 3/2010 | |
| CN | 101677851 A | 3/2010 | |
| CN | 102858272 A | 1/2013 | |
| CN | 102869320 A | 1/2013 | |
| CN | 102892384 A | 1/2013 | |
| CN | 103118630 A | 5/2013 | |
| CN | 103189015 A | 7/2013 | |
| CN | 103228231 A | 7/2013 | |
| CN | 103298426 A | 9/2013 | |
| CN | 103370035 A | 10/2013 | |
| CN | 103391756 A | 11/2013 | |
| CN | 103826570 A | 5/2014 | |
| CN | 102245120 B | 8/2014 | |
| CN | 104220027 A | 12/2014 | |
| CN | 102917668 B | 1/2015 | |
| CN | 104394803 A | 3/2015 | |
| CN | 104582637 A | 4/2015 | |
| CN | 102905647 B | 7/2015 | |
| CN | 103648570 B | 9/2015 | |
| CN | 104884000 A | 9/2015 | |
| CN | 104160076 B | 12/2015 | |
| CN | 105380730 A | 3/2016 | |
| CN | 105451687 A | 3/2016 | |
| CN | 105520792 A | 4/2016 | |
| CN | 105530893 A | 4/2016 | |
| CN | 102458309 B | 5/2016 | |
| CN | 103200900 B | 5/2016 | |
| CN | 105555232 A | 5/2016 | |
| CN | 105578992 A | 5/2016 | |
| CN | 103338709 B | 6/2016 | |
| CN | 105658178 A | 6/2016 | |
| CN | 105792780 A | 7/2016 | |
| CN | 103347467 B | 8/2016 | |
| CN | 103648439 B | 8/2016 | |
| CN | 103889472 B | 8/2016 | |
| CN | 105899150 A | 8/2016 | |
| CN | 103153232 B | 9/2016 | |
| CN | 106061437 A | 10/2016 | |
| CN | 106068109 A | 11/2016 | |
| CN | 106073946 A | 11/2016 | |
| CN | 106255475 A | 12/2016 | |
| CN | 103917194 B | 2/2017 | |
| CN | 106456324 A | 2/2017 | |
| CN | 106456325 A | 2/2017 | |
| CN | 105073068 B | 3/2017 | |
| CN | 106470641 A | 3/2017 | |
| CN | 105451684 B | 4/2017 | |
| CN | 106573129 A | 4/2017 | |
| CN | 103945792 B | 5/2017 | |
| CN | 106659394 A | 5/2017 | |
| CN | 106716098 A | 5/2017 | |
| CN | 106794063 A | 5/2017 | |
| CN | 106890035 A | 6/2017 | |
| CN | 106943207 A | 7/2017 | |
| CN | 106999054 A | 8/2017 | |
| CN | 106999281 A | 8/2017 | |
| CN | 104114127 B | 9/2017 | |
| CN | 107115161 A | 9/2017 | |
| CN | 107249482 A | 10/2017 | |
| CN | 107260366 A | 10/2017 | |
| CN | 104918582 B | 11/2017 | |
| CN | 107374783 A | 11/2017 | |
| CN | 107427364 A | 12/2017 | |
| CN | 107438415 A | 12/2017 | |
| CN | 106255476 B | 1/2018 | |
| CN | 107530157 A | 1/2018 | |
| CN | 107530167 A | 1/2018 | |

(56)                    References Cited

FOREIGN PATENT DOCUMENTS

| | | | |
|---|---|---|---|
| CN | 107530177 | A | 1/2018 |
| CN | 107613908 | A | 1/2018 |
| CN | 104869948 | B | 2/2018 |
| CN | 107714240 | A | 2/2018 |
| CN | 107920862 | A | 4/2018 |
| CN | 107920897 | A | 4/2018 |
| CN | 104853696 | B | 6/2018 |
| CN | 108135696 | A | 6/2018 |
| CN | 108430392 | A | 8/2018 |
| CN | 108472142 | A | 8/2018 |
| CN | 108495602 | A | 9/2018 |
| CN | 106726007 | B | 11/2018 |
| CN | 109124829 | A | 1/2019 |
| CN | 109199641 | A | 1/2019 |
| CN | 109561962 | A | 4/2019 |
| CN | 109567991 | A | 4/2019 |
| CN | 109862835 | A | 6/2019 |
| CN | 109906063 | A | 6/2019 |
| CN | 109996581 | A | 7/2019 |
| CN | 110013358 | A | 7/2019 |
| CN | 110290764 | A | 9/2019 |
| DE | 102014102648 | A1 | 9/2015 |
| DE | 102014102650 | A1 | 9/2015 |
| DE | 102014102718 | A1 | 9/2015 |
| DE | 102014102722 | A1 | 9/2015 |
| DE | 202017104793 | U1 | 11/2018 |
| DE | 202016008737 | U1 | 4/2019 |
| DK | 2549953 | T3 | 2/2017 |
| DK | 2254514 | T3 | 12/2018 |
| EA | 027348 | B1 | 7/2017 |
| EP | 0902704 | A4 | 3/1999 |
| EP | 1301225 | A2 | 4/2003 |
| EP | 1684666 | A2 | 8/2006 |
| EP | 1996246 | A2 | 12/2008 |
| EP | 2211779 | A1 | 8/2010 |
| EP | 2254513 | A1 | 12/2010 |
| EP | 2263605 | A1 | 12/2010 |
| EP | 2273947 | A1 | 1/2011 |
| EP | 2296744 | A1 | 3/2011 |
| EP | 2379008 | A2 | 10/2011 |
| EP | 2400926 | A2 | 1/2012 |
| EP | 2427145 | A2 | 3/2012 |
| EP | 1582178 | B1 | 9/2012 |
| EP | 2542186 | A2 | 1/2013 |
| EP | 2558030 | A1 | 2/2013 |
| EP | 2560579 | A1 | 2/2013 |
| EP | 2575681 | A1 | 4/2013 |
| EP | 2603172 | A2 | 6/2013 |
| EP | 2637607 | A1 | 9/2013 |
| EP | 2651337 | A2 | 10/2013 |
| EP | 2658476 | A1 | 11/2013 |
| EP | 2699201 | A1 | 2/2014 |
| EP | 2405966 | B1 | 4/2014 |
| EP | 2055263 | B1 | 6/2014 |
| EP | 2741711 | A2 | 6/2014 |
| EP | 2793763 | A1 | 10/2014 |
| EP | 2822503 | A2 | 1/2015 |
| EP | 2538879 | B1 | 4/2015 |
| EP | 2444031 | B1 | 7/2015 |
| EP | 1702247 | B1 | 8/2015 |
| EP | 2772228 | B1 | 11/2015 |
| EP | 2943160 | A2 | 11/2015 |
| EP | 2470098 | B1 | 12/2015 |
| EP | 1991168 | B1 | 1/2016 |
| EP | 2254512 | B1 | 1/2016 |
| EP | 2964152 | A1 | 1/2016 |
| EP | 2967853 | A1 | 1/2016 |
| EP | 2967860 | A1 | 1/2016 |
| EP | 2994073 | A1 | 3/2016 |
| EP | 3001978 | A1 | 4/2016 |
| EP | 3003187 | A1 | 4/2016 |
| EP | 3007649 | A1 | 4/2016 |
| EP | 3010447 | A1 | 4/2016 |
| EP | 3017792 | A1 | 5/2016 |
| EP | 3019092 | A1 | 5/2016 |
| EP | 2563236 | B1 | 6/2016 |
| EP | 3027143 | A1 | 6/2016 |
| EP | 3037064 | A1 | 6/2016 |
| EP | 2211758 | B1 | 7/2016 |
| EP | 3052053 | A1 | 8/2016 |
| EP | 3060140 | A1 | 8/2016 |
| EP | 3062745 | A1 | 9/2016 |
| EP | 3071149 | A1 | 9/2016 |
| EP | 2282700 | B1 | 11/2016 |
| EP | 2967854 | B1 | 11/2016 |
| EP | 1998713 | B1 | 12/2016 |
| EP | 3099271 | A1 | 12/2016 |
| EP | 3100701 | A1 | 12/2016 |
| EP | 3141219 | A1 | 3/2017 |
| EP | 3157469 | A1 | 4/2017 |
| EP | 2538880 | B1 | 5/2017 |
| EP | 2967852 | B1 | 6/2017 |
| EP | 3174503 | A1 | 6/2017 |
| EP | 3182931 | A1 | 6/2017 |
| EP | 2830536 | B1 | 8/2017 |
| EP | 2830537 | B1 | 9/2017 |
| EP | 2720642 | B1 | 10/2017 |
| EP | 3232941 | A1 | 10/2017 |
| EP | 3256076 | A1 | 12/2017 |
| EP | 3281608 | A1 | 2/2018 |
| EP | 2608815 | B1 | 3/2018 |
| EP | 3310302 | A1 | 4/2018 |
| EP | 3311778 | A1 | 4/2018 |
| EP | 3337412 | A1 | 6/2018 |
| EP | 3340931 | A1 | 7/2018 |
| EP | 3344188 | A1 | 7/2018 |
| EP | 3344197 | A1 | 7/2018 |
| EP | 3345573 | A1 | 7/2018 |
| EP | 2822473 | B1 | 8/2018 |
| EP | 3354208 | A1 | 8/2018 |
| EP | 3370649 | A1 | 9/2018 |
| EP | 3372198 | A1 | 9/2018 |
| EP | 3372199 | A1 | 9/2018 |
| EP | 3375411 | A1 | 9/2018 |
| EP | 2928538 | B1 | 11/2018 |
| EP | 3399947 | A1 | 11/2018 |
| EP | 3400913 | A1 | 11/2018 |
| EP | 3406224 | A1 | 11/2018 |
| EP | 2555709 | B1 | 12/2018 |
| EP | 3417813 | A1 | 12/2018 |
| EP | 3426188 | A1 | 1/2019 |
| EP | 3429507 | A1 | 1/2019 |
| EP | 3431040 | A1 | 1/2019 |
| EP | 3432825 | A1 | 1/2019 |
| EP | 3432834 | A1 | 1/2019 |
| EP | 3437669 | A1 | 2/2019 |
| EP | 3448312 | A1 | 3/2019 |
| EP | 3454787 | A1 | 3/2019 |
| EP | 2663259 | B1 | 5/2019 |
| EP | 3302364 | B1 | 5/2019 |
| EP | 3478224 | A1 | 5/2019 |
| EP | 3484411 | A1 | 5/2019 |
| EP | 3487420 | A1 | 5/2019 |
| EP | 2560580 | B1 | 6/2019 |
| EP | 3508113 | A1 | 7/2019 |
| EP | 3518748 | A1 | 8/2019 |
| EP | 3522830 | A1 | 8/2019 |
| EP | 3528749 | A1 | 8/2019 |
| EP | 3288495 | B1 | 9/2019 |
| EP | 3538024 | A1 | 9/2019 |
| EP | 3538025 | A1 | 9/2019 |
| EP | 3019123 | B1 | 10/2019 |
| EP | 3552584 | A1 | 10/2019 |
| EP | 3552655 | A1 | 10/2019 |
| EP | 3897462 | A1 | 10/2021 |
| ES | 2369241 | T3 | 11/2011 |
| ES | 2647777 | T3 | 12/2017 |
| ES | 2664243 | T3 | 4/2018 |
| ES | 2675726 | T3 | 7/2018 |
| GB | 2539444 | A | 12/2016 |
| JP | 2003530956 | A | 10/2003 |
| JP | 2005521513 | A | 7/2005 |
| JP | 2008506459 | A | 3/2008 |
| JP | 2008512211 | A | 4/2008 |

(56) References Cited

FOREIGN PATENT DOCUMENTS

| | | | |
|---|---|---|---|
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010508093 A | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013517011 A | 5/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2014528761 A | 10/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008055301 A1 | 5/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010079427 A1 | 7/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO-2012035279 A1 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |

(56)                    References Cited

FOREIGN PATENT DOCUMENTS

| WO | WO-2016183523 A1 | 11/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017123802 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018136726 A1 | 7/2018 |
| WO | WO-2018138658 A1 | 8/2018 |
| WO | WO-2018145055 A1 | 8/2018 |
| WO | WO-2018148839 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO-2019190800 A1 | 10/2019 |
| WO | WO-2019191102 A1 | 10/2019 |
| WO | WO-2019195860 A2 | 10/2019 |
| WO | WO-2020061124 A1 | 3/2020 |
| WO | WO-2020061331 A2 | 3/2020 |
| WO | WO-2020131978 A1 | 6/2020 |
| WO | WO-2020146842 A1 | 7/2020 |
| WO | WO-2020154735 A1 | 7/2020 |
| WO | WO-2020181154 A2 | 9/2020 |
| WO | WO-2020186251 A1 | 9/2020 |
| WO | WO-2020227249 A1 | 11/2020 |
| WO | WO-2021035032 A1 | 2/2021 |
| WO | WO-2021040996 A1 | 3/2021 |
| WO | WO-2021146515 A1 | 7/2021 |
| WO | WO-2022010974 A1 | 1/2022 |
| WO | WO-2023164489 A2 | 8/2023 |
| WO | WO-2024081883 A1 | 4/2024 |
| WO | WO-2025006451 A1 | 1/2025 |

OTHER PUBLICATIONS

Extended European Search Report for European Application No. 19897707.6, mailed Sep. 6, 2022, 7 pages.
Extended European Search Report for European Application No. 20745513.0, mailed Sep. 20, 2022, 9 pages.
Extended European Search Report for European Application No. 20767325.2, mailed on Oct. 25, 2022, 5 pages.
Extended European Search Report for European Application No. 20769769.9, mailed Oct. 17, 2022, 6 pages.
Extended European Search Report for European Application No. 20801681.6, mailed Jan. 18, 2023, 13 pages.
Extended European Search Report for European Application No. EP20854535 dated Jun. 23, 2023, 8 pages.
Extended European Search Report for European Application No. EP20856704 dated Aug. 22, 2023, 11 pages.
International Search Report and Written Opinion for International Application No. PCT/US2019/028822, mailed Oct. 24, 2019, 14 pages.
International Search Report and Written Opinion for International Application No. PCT/US2019/051615, mailed Mar. 2, 2020, 14 pages.
International Search Report and Written Opinion for International Application No. PCT/US2019/051957, mailed Apr. 30, 2020, 16 pages.
International Search Report and Written Opinion for International Application No. PCT/US2019/067010, mailed Mar. 10, 2020, 17 pages.

(56) References Cited

OTHER PUBLICATIONS

International Search Report and Written Opinion for International Application No. PCT/US2020/013240, mailed Jun. 3, 2020, 7 pages.
International Search Report and Written Opinion for International Application No. PCT/US2020/015231, mailed Apr. 23, 2020, 10 pages.
International Search Report and Written Opinion for International Application No. PCT/US2020/021300, mailed Oct. 7, 2020, 6 pages.
International Search Report and Written Opinion for International Application No. PCT/US2020/022828, mailed May 19, 2020, 12 pages.
International Search Report and Written Opinion for International Application No. PCT/US2020/031390, mailed Aug. 3, 2020, 10 pages.
International Search Report and Written Opinion for International Application No. PCT/US2020/045195, mailed Jan. 8, 2021, 18 pages.
International Search Report and Written Opinion for International Application No. PCT/US2020/047162, mailed Dec. 30, 2020, 9 pages.
International Search Report and Written Opinion for International Application No. PCT/US2021/013570, mailed Apr. 1, 2021, 9 pages.
International Search Report and Written Opinion for PCT Application No. PCT/US2023/063044 dated Oct. 24, 2023, 13 pages.
Invitation to pay additional fees for International Application No. PCT/US2023/063044, dated Jul. 31, 2023, 2 pages.
Office Action for European Application No. 19863898.3 mailed Nov. 27, 2023, 4 pages.
Office Action for European Application No. 20769769.9 dated Sep. 8, 2023, 4 pages.
Office Action for European Application No. EP20200801681 dated Dec. 11, 2023, 7 pages.
Office Action for European Application No. 19863898.3 dated Mar. 24, 2023, 6 pages.
Office Action for Japanese Application No. JP20210516666 dated Aug. 31, 2023, 19 pages.
Office Action for Japanese Application No. JP20210535023 dated Oct. 27, 2023, 17 pages.
Office Action for U.S. Appl. No. 16/155,890, mailed Feb. 8, 2019, 13 pages.
Office Action for U.S. Appl. No. 16/163,577, mailed Mar. 8, 2021, 10 pages.
Office Action for U.S. Appl. No. 16/435,687, mailed Aug. 7, 2019, 19 pages.
Office Action for U.S. Appl. No. 16/442,504, mailed Jan. 14, 2020, 11 pages.
Office Action for U.S. Appl. No. 16/443,862, mailed Nov. 12, 2021, 9 pages.
Office Action for U.S. Appl. No. 16/445,210, mailed Jan. 28, 2021, 7 pages.
Office Action for U.S. Appl. No. 16/448,108, mailed Jan. 21, 2020, 14 pages.
Office Action for U.S. Appl. No. 16/448,108, mailed Mar. 8, 2021, 8 pages.
Office Action for U.S. Appl. No. 16/448,108, mailed Sep. 1, 2020, 14 pages.
Office Action for U.S. Appl. No. 16/449,420, mailed Sep. 1, 2021, 16 pages.
Office Action for U.S. Appl. No. 16/455,417, mailed Sep. 23, 2019, 11 pages.
Office Action for U.S. Appl. No. 16/455,740, mailed Jul. 24, 2020, 7 pages.
Office Action for U.S. Appl. No. 16/711,415, mailed Jan. 18, 2022, 7 pages.
Office Action for U.S. Appl. No. 17/062,080, mailed Dec. 15, 2022, 14 pages.

Office Action for U.S. Appl. No. 17/154,227, mailed Jun. 18, 2021, 8 pages.
Office Action for U.S. Appl. No. 17/154,227, mailed Mar. 29, 2021, 6 pages.
Office Action for U.S. Appl. No. 17/154,438, mailed May 3, 2021, 16 pages.
Office Action for U.S. Appl. No. 17/167,983, mailed Apr. 13, 2021, 20 pages.
Office Action for U.S. Appl. No. 17/167,988, mailed Sep. 22, 2021, 19 pages.
Office Action for U.S. Appl. No. 17/193,936, mailed May 27, 2021, 6 pages.
Office Action for U.S. Appl. No. 17/207,076 dated Aug. 17, 2023, 6 pages.
Office Action for U.S. Appl. No. 17/221,547, mailed Aug. 4, 2021, 11 pages.
Office Action for U.S. Appl. No. 17/221,547, mailed Oct. 21, 2021, 9 pages.
Office Action for U.S. Appl. No. 17/222,182, mailed Sep. 2, 2021, 23 pages.
Office Action for U.S. Appl. No. 17/222,430, mailed Oct. 7, 2021, 17 pages.
Office Action for U.S. Appl. No. 17/236,219, mailed Aug. 4, 2021, 17 pages.
Office Action for U.S. Appl. No. 17/388,983, mailed Jan. 6, 2022, 11 pages.
Office Action for U.S. Appl. No. 17/666,086 dated Jul. 5, 2023, 16 pages.
International Search Report and Written Opinion for International Application No. PCT/US2023/076845 dated Mar. 4, 2024, 10 pages.
Non-Final Office Action for U.S. Appl. No. 17/526,691 dated Mar. 11, 2024, 9 pages.
Office Action and Search report for Chinese Application No. CN201980075586.9 dated Feb. 5, 2024, 15 pages.
Office Action for Canadian Application No. CA3152042 dated Feb. 20, 2024, 5 pages.
Office Action for Canadian Patent Application No. CA20203152632 dated Feb. 19, 2024, 4 pages.
Office Action for Canadian Patent Application No. CA3113429 dated Feb. 13, 2024, 4 pages.
Office Action for Japanese Application No. JP20210563105 mailed Feb. 26, 2024, 8 pages.
Office Action for Japanese Patent Application No. JP20210555207 dated Jan. 31, 2024, 6 pages.
Office Action for Japanese Patent Application No. JP2021547343 dated Jan. 31, 2024, 6 pages.
Office Action and Search report for Chinese Patent Application No. CN201980090378.6 dated Mar. 12, 2024, 28 pages.
Extended European Search Report for European Application No. 23215329.6, mailed on Jul. 5, 2024, 5 pages.
Office Action for Australian Application No. 2019342130 mailed May 22, 2024, 3 pages.
Office Action for Australian Application No. 2019406832 mailed Jul. 26, 2024, 4 pages.
Office Action for Chinese Application No. 202080074543.1, with Search Report, mailed Mar. 28, 2024, 18 pages, English translation included.
Office Action for European Application No. 20801681.6 mailed Jul. 31, 2024, 5 pages.
Office Action for European Application No. 20856704.0 mailed Jul. 29, 2024, 4 pages.
Office Action for Japanese Application No. 2021-516666 mailed Apr. 22, 2024, 6 pages, English translation included.
Office Action for Japanese Application No. 2021-535023 mailed Apr. 22, 2024, 4 pages, English translation included.
Office Action for Japanese Application No. 2021-547343 mailed May 13, 2024, 4 pages, English translation included.
Office Action for Japanese Application No. 2022-511360 mailed Apr. 18, 2024, 6 pages, English translation included.
Office Action for Japanese Application No. 2022-513172 mailed Apr. 18, 2024, 12 pages, English translation included.

(56) References Cited

OTHER PUBLICATIONS

Office Action for U.S. Appl. No. 17/372,022 mailed Aug. 1, 2024, 15 pages.
Office Action for U.S. Appl. No. 17/707,493 mailed Jul. 8, 2024, 9 pages.
Office Action for U.S. Appl. No. 17/707,493 mailed Mar. 29, 2024, 21 pages.
Office Action for U.S. Appl. No. 17/825,551, mailed Aug. 29, 2024, 11 pages.
International Search Report and Written Opinion for International Application No. PCT/US2024/035388, mailed Dec. 3, 2024, 12 pages.
Invitation to Pay Additional Fees for International Application No. PCT/US2024/035388, mailed Sep. 17, 2024, 3 pages.
Office Action for Australian Application No. 2020231221 mailed Sep. 11, 2024, 4 pages.
Office Action for Australian Application No. 2020239265 mailed Sep. 2, 2024, 3 pages.
Office Action for Australian Application No. 2020267390 mailed Jan. 23, 2025, 3 pages.
Office Action for U.S. Appl. No. 17/682,875, mailed Sep. 28, 2024, 18 pages.
Office Action for U.S. Appl. No. 18/329,098, mailed Oct. 24, 2024, 12 pages.
Extended European Search Report for European Application No. 24205403.9, mailed on Mar. 7, 2025, 11 pages.

Extended European Search Report for European Application No. 24209298.9, mailed Feb. 21, 2025, 10 pages.
Extended European Search Report for European Application No. 24222817.9, mailed on Apr. 15, 2025, 17 pages.
Office Action for Australian Application No. 2019406832 mailed Apr. 4, 2025, 4 pages.
Office Action for Australian Application No. 2020334080 mailed Feb. 20, 2025, 4 pages.
Office Action for Australian Application No. 2020337235 mailed May 13, 2025, 4 pages.
Office Action for Canadian Application No. 3113429 mailed Feb. 13, 2025, 3 pages.
Office Action for Chinese Application No. 202080018634.3, mailed Feb. 15, 2025, 21 pages, English translation included.
Office Action for Chinese Application No. 202080031726.5, mailed Feb. 22, 2025, with English Translation, 13 pages.
Office Action for Chinese Application No. 202080036597.9, mailed Feb. 27, 2025, with English Translation, 11 pages.
Office Action for Chinese Application No. 202080073176.3, mailed Mar. 8, 2025, with English Translation, 14 pages.
Office Action for Chinese Application No. 202080074543.1, mailed Jan. 20, 2025, 11 pages, English translation included.
Office Action for U.S. Appl. No. 17/751,177, mailed Jun. 4, 2025, 10 pages.
Office Action for U.S. Appl. No. 17/825,551, mailed May 9, 2025, 10 pages.
Office Action for Canadian Application No. 3132162, mailed Jul. 31, 2025, 6 pages.

* cited by examiner

100

104

182
179
170
124
114
122

Outer
Frame
110

Flow
Control
150

10

Removably couple a control device to a supra-annular portion
of the prosthetic valve
11

Removably couple a supra-annular support to the supra-annular
portion of the prosthetic valve
12

Advance the control device and the prosthetic valve in a
compressed configuration through a lumen of a delivery catheter
to place a distal end portion of the control device and the
prosthetic valve into a chamber of the heart
13

Transition the supra-annular support from a first state to a
second state
14

Seat the prosthetic valve in the native annulus while the supra-
annular support is in the second state
15

Decouple each of the control device and the supra-annular
support from the prosthetic valve after the seating
16

DEVICES AND METHODS FOR DELIVERING A PROSTHETIC HEART VALVE USING SUPRA-ANNULAR SUPPORT

CROSS-REFERENCE TO RELATED APPLICATIONS

This application is a continuation of International Application No. PCT/US2023/076845, filed Oct. 13, 2023, entitled "Devices and Methods for Delivering a Prosthetic Heart Valve using Supra-Annular Support," which claims priority to and the benefit of U.S. Provisional Patent Application No. 63/510,699, filed Jun. 28, 2023, entitled "Devices and Methods for Delivering a Prosthetic Heart Valve using Supra-Annular Support," U.S. Provisional Patent Application No. 63/505,966, filed Jun. 2, 2023, entitled "Devices and Methods for Delivering a Prosthetic Heart Valve using Supra-Annular Support," and U.S. Provisional Patent Application No. 63/379,569, filed Oct. 14, 2022, entitled "Devices and Methods for Delivering a Prosthetic Heart Valve using a Supra-Annular Support," the disclosure of each of which is incorporated herein by reference in its entirety.

BACKGROUND

Embodiments described herein relate generally to transcatheter prosthetic heart valves and more particularly, to devices, systems, and/or methods for delivering side-deliverable transcatheter prosthetic heart valves using one or more supra-annular supports and/or actuators such as one or more tethers.

Prosthetic heart valves can pose challenges for delivery, deployment, and/or retrieval within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to a lengthwise or longitudinal axis of the delivery catheter. In other words, traditional prosthetic valves are loaded into a delivery catheter such that a radial extent of the valve is aligned with and/or fits within a radial extent of a lumen extending through the delivery catheter. The valves are deployed from an end of the delivery catheter and expanded outwardly in a radial direction from the central annular axis. The vasculature of a patient, however, places limitations on a diameter of the delivery catheter, which in turn, places limits on the radial extent of the lumen extending through the delivery catheter, and thus, limits the expanded size (e.g., diameter) of a prosthetic valve delivered using the traditional, radial compressed delivery method. The competing interest of minimizing delivery catheter size presents challenges to increasing the expanded diameter of radially compressed valves (e.g., trying to compress too much material and structure into too little space). Moreover, the orientation of the traditional valves during deployment can create additional challenges when trying to align the valves with the native valve annulus.

Some transcatheter prosthetic valves can be configured for side and/or orthogonal delivery, which can allow for an increase in an expanded diameter relative to traditionally delivered valves. With side delivery, for example, the valve can be placed in a compressed or delivery configuration and loaded into a delivery catheter such that a central annular axis of the valve is substantially perpendicular and/or orthogonal to the lengthwise or longitudinal axis of the delivery catheter. More particularly, the valve can be compressed axially (e.g., along the central annular axis) and laterally (e.g., perpendicular to each of the central annular axis and a longitudinal axis of the valve), and uncompressed or elongated longitudinally (e.g., in a direction parallel to the lengthwise or longitudinal axis of the delivery catheter). The compressed valve (e.g., the valve in a delivery configuration) can be loaded into a lumen of the delivery catheter in a side-ways or orthogonal orientation, in which the central annular axis of the valve is substantially perpendicular and/or orthogonal to the lengthwise or longitudinal axis of the delivery catheter. Once loaded, the compressed valve can be advanced through the lumen of the delivery catheter and deployed from the end of the delivery catheter (e.g., into a chamber of the heart such as an atrium). Furthermore, in some instances, the side-ways or orthogonal orientation of the deployed side-delivered valve relative to the delivery catheter, in general, results in the valve being deployed in a desired orientation relative to the native valve annulus.

While side delivery can allow for the delivery of larger valves and can simplify a process of aligning or orienting the valve relative to the native annulus relative to traditional delivery, challenges exist with seating side-deliverable prosthetic valves in the native annulus. For example, traditional, radially compressed valves can be maintained in an at least partially compressed state while a portion of the prosthetic valve is inserted through the annulus. Once in a desired position, the prosthetic valve can be allowed to transition to a radially uncompressed state, thereby seating the traditionally delivered valve in the native annulus. On the other hand, in some tricuspid valve replacements, seating a side-deliverable prosthetic valve can include inserting a distal portion of the valve into the annulus such that a distal wall of the valve contacts a distal wall of the annulus, a distal subannular portion, tab, or anchor is below the annulus and disposed in or near a ventricular outflow tract (RVOT), and a supra-annular portion of the valve such as an atrial cuff or the like is above the annulus. Once positioned, the valve can be pivoted relative to the annular plane to insert a proximal portion of the valve into/through the native annulus, thereby seating the valve. In some instances, however, it may be desirable to increase a stability of such a side-deliverable valve while the valve is being deployed (pivoted) into the annulus. It may also be desirable to decrease a likelihood of a supra-annular portion of the valve (e.g., a portion of an atrial cuff or the like) falling into the annulus and/or to decrease or adjust an amount or manner of contact between a distal portion of the valve and at least a portion of the tissue defining or surrounding the annulus.

Accordingly, a need exists for devices, systems, and/or methods for delivering side-deliverable transcatheter prosthetic heart valves using one or more supra-annular supports and/or actuators such as one or more tethers.

SUMMARY

The embodiments described herein are directed to side-deliverable transcatheter prosthetic heart valves and devices, systems, and/or methods for delivering the prosthetic valves using one or more supra-annular supports and/or actuators. In some embodiments, a delivery system includes a delivery sheath with each of a control device and at least one supra-annular support being movable through a lumen of the delivery sheath. The control device includes a control catheter and a connection member coupled to a distal end of the control catheter. The connection member is configured to removably couple to the prosthetic valve at a proximal position along a supra-annular portion of the prosthetic valve. The control device is operable to advance the pros-
thetic valve in a compressed configuration through the
delivery sheath and to at least partially deploy the prosthetic
valve in an expanded configuration into a native valve
annulus. The supra-annular support(s) is/are removably
coupleable to the prosthetic valve at one or more positions
along a supra-annular portion thereof and is/are configured
to stabilize or actuate at least a portion of the prosthetic
valve relative to an annular plane of a native heart valve
during deployment.

BRIEF DESCRIPTION OF THE DRAWINGS

FIG. 26 is a flowchart illustrating a method of delivering
and deploying a side-deliverable transcatheter prosthetic
valve into an annulus of a native valve according to an
embodiment.

DETAILED DESCRIPTION

Figures 1, 2:
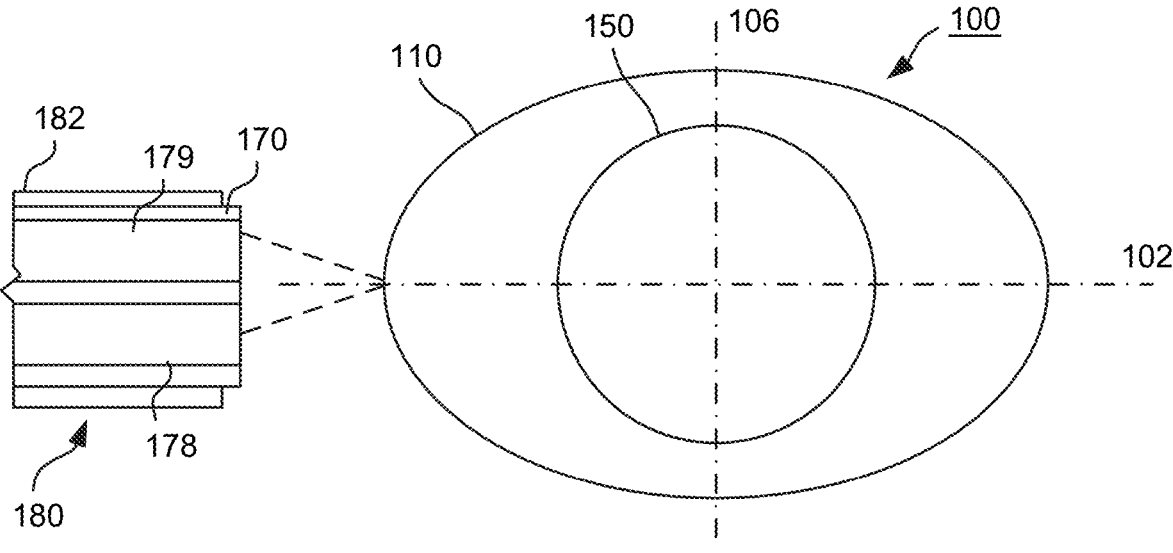
FIGS. 1-6 are schematic illustrations of a side-deliverable
transcatheter prosthetic valve selectively coupled to a deliv-
ery system (or portions thereof) used to deliver and deploy
the prosthetic valve into an annulus of a native heart valve,
according to an embodiment.

Disclosed embodiments are directed to side-deliverable
transcatheter prosthetic heart valves and/or components
thereof, and devices, systems, and/or methods of delivering
and deploying the prosthetic valves into an annulus of a
native valve using one or more supra-annular supports. In
some embodiments, a delivery system includes a delivery
sheath with each of a control device and at least one
supra-annular support being movable through a lumen of the
delivery sheath. The control device includes a control cath-
eter and a connection member coupled to a distal end of the
control catheter. The connection member is configured to
removably couple to the prosthetic valve at a proximal
position along a supra-annular portion of the prosthetic
valve. The control device is operable to advance the pros-
thetic valve in a compressed configuration through the
delivery sheath and to at least partially deploy the prosthetic
valve in an expanded configuration into a native valve
annulus. The supra-annular support(s) is/are removably
coupleable to the prosthetic valve at one or more positions
along a supra-annular portion thereof and is/are configured
to stabilize or actuate at least a portion of the prosthetic
valve relative to an annular plane of a native heart valve
during deployment.

In some embodiments, a delivery system includes a
delivery sheath with each of a control device and a supra-
annular support being movable through a lumen of the
delivery sheath. The control device includes a connection
member coupled to a distal end of a control catheter and
configured to removably couple to a proximal supra-annular
portion of the prosthetic valve. The control device operable
to advance the prosthetic valve in a compressed configura-
tion through the delivery sheath and to deploy the prosthetic
valve in an expanded configuration into a native valve
annulus. The supra-annular support removably coupleable to
a distal supra-annular portion of the prosthetic valve and
configured to transition from a first state to a second state
when the prosthetic valve is in the expanded configuration.
The supra-annular support in the second state forming a
substantially fixed-length connection between the delivery
sheath and the distal supra-annular portion of the prosthetic
valve.

In some embodiments, a method of delivering and/or
deploying a side-deliverable prosthetic valve into a native
valve annulus of a heart includes removably coupling a
control device and a supra-annular support to a supra-
annular portion of the prosthetic valve. In some implemen-
tations, the control device can be removably coupled to a
proximal supra-annular portion of the prosthetic valve while the supra-annular support is removably coupled to a distal supra-annular portion of the prosthetic valve. The control device and the prosthetic valve in a compressed configuration are advanced through a lumen of a delivery catheter to place a distal end portion of the control device and the prosthetic valve into a chamber of the heart. The prosthetic valve is configured to transition to an expanded configuration when in the chamber of the heart. With the prosthetic valve in the chamber of the heart, the supra-annular support is transitioned from a first state to a second state. In some implementations, transitioning the supra-annular support from the first state to the second state can allow the supra-annular support to form a substantially rigid connection between a distal end of a delivery sheath and the distal subannular portion of the prosthetic valve. In some implementations, transitioning the supra-annular support from the first state to the second state can actuate the supra-annular portion of the prosthetic valve (e.g., can move, bend, flex, and/or otherwise reconfigure at least part of the supra-annular portion of the prosthetic valve). The prosthetic valve is seated in the native annulus while the supra-annular support is in the second state. Each of the control device and the supra-annular support are decoupled from the prosthetic valve after the seating. In some implementations, decoupling the supra-annular support can include, for example, withdrawing a guidewire catheter into the delivery sheath to release a distal end portion of the supra-annular support.

Any of the prosthetic valves described herein can be relatively low-profile, transcatheter prosthetic heart valves. The prosthetic heart valves herein can have a valve frame and a flow control component mounted within a central lumen, aperture, and/or channel of the valve frame that extends along a central axis of the valve or valve frame that is co-axial or at least substantially parallel with a blood flow direction through the valves. The valve frame can provide structural support for the prosthetic valve and/or at least the flow control component mounted thereto. The valve frame can also provide one or more components or elements for anchoring or otherwise securing the prosthetic valves in an annulus of a native valve. The flow control component (e.g., a 2-leaflet or 3-leaflet sleeve, valve, and/or the like) can be configured to permit blood flow in a first direction through an inflow end of the valve and out an outflow end of the valve, and block blood flow in a second direction, opposite the first direction.

Any of the delivery and/or deployment systems and/or methods described herein can be used and/or implemented for traditionally deliverable valves or orthogonal/side-deliverable valves unless clearly stated otherwise. For example, the valves described herein can be configured to transition (e.g., via balloon inflation or via one or more self-expanding structures) between a compressed or delivery configuration for introduction into the body via a delivery catheter, and an expanded or deployment/deployed configuration for implanting at a desired location in the body. The delivery catheter can be, for example, a 24-36 French (Fr) delivery catheter that is advanced through the vasculature of a patient and into a chamber of a heart. In general, traditionally delivered/deliverable valves are configured to be compressed in, for example, a radial direction relative to the central axis or blood flow direction through the valve, and inserted into and/or advanced through the delivery catheter such that the central axis of the compressed valve is parallel to a longitudinal or lengthwise axis of the delivery catheter used to deliver the valve. The valves are deployed from the end of the delivery catheter and expanded outwardly in a radial direction from the central cylinder axis. The delivery orientation of the valve generally means that the valve is completely released from the delivery catheter while in the atrium of the heart and reoriented relative to the annulus, which in some instances, can limit a size of the valve. Accordingly, in some implementations, traditional delivery can be used for relatively small diameter valves such as, for example, prosthetic pulmonary and/or aortic valves.

Orthogonal or side-delivered/deliverable valves are configured to be compressed in at least one of a lateral direction (orthogonal to the blood flow direction through the valve) or an axial direction (parallel to or aligned with the blood flow direction). In some embodiments, any of the valves can be compressed in two directions—the lateral direction and the axial direction—without compressing the valve in a direction along a lengthwise or longitudinal axis of the valve (orthogonal to the blood flow direction through the valve). With orthogonal or side-delivery, the compressed valve can be inserted and/or advanced through a delivery catheter such that the central axis of the compressed valve is substantially orthogonal or perpendicular to a longitudinal or lengthwise axis of the delivery catheter. Said another way, in orthogonal or side-delivery, the lengthwise or longitudinal axis of the valve can be substantially parallel to the lengthwise or longitudinal axis of the delivery catheter through which the valve is delivered. Thus, an orthogonally delivered and/or side delivered prosthetic valve is compressed and/or delivered sideways (e.g., at a roughly 90-degree angle) compared to traditional processes of compressing and delivering transcatheter prosthetic valves.

In some implementations, the orientation of orthogonally delivered valves relative to the annulus can allow a distal portion of the valve to be at least partially inserted into the annulus of the native heart valve while the proximal portion of the valve, at least in part, remains in the delivery catheter, thereby avoiding at least some of the size constraints faced with some known traditional delivery techniques. For example, a relatively large side-deliverable prosthetic valve in an expanded configuration can have a height of about 5-60 millimeters (mm) and a diameter of about 20-80 mm, and in a compressed configuration can have a height of about 5-12 mm, a width (e.g., in a lateral direction) of about 8-12 mm, and a length (e.g., in a longitudinal or lengthwise direction) of about 25-80 mm. Moreover, orthogonal or side delivery can allow the valves to be deployed from the inferior vena cava (IVC) into the annulus of a native mitral or tricuspid valve without positioning the delivery catheter at an acute angle relative to the native valve, which is otherwise common in traditional transcatheter delivery.

While valves configured for orthogonal delivery can allow for the deployment of relatively large valves, traditionally delivered valve are configured to be radially compressed during delivery, and in some instances, such radial compression may facilitate the process of seating some traditionally delivered prosthetic valve in the annulus of a native heart valve. For example, such valves can be at least partially radially compressed to allow a portion of the prosthetic valve to be dropped into the annulus. Once the valve is in a desired position, the valve can be transitioned and/or allowed to transition to a radially expanded (or radially uncompressed) state, thereby seating the prosthetic valve in the annulus of the native heart valve. On the other hand, the process of deploying and/or seating certain orthogonally delivered prosthetic valves can include inserting a distal portion of the prosthetic valve through the annulus and then pivoting the remaining portion(s) of the valve into a desired position. In some instances, this difference in the process of seating the valve in the annulus can give rise to a desire for additional features and/or methods that increase stability of the orthogonally delivered valve during deployment (seating) into the native annulus, such as any of those described herein.

Any of the prosthetic heart valves described herein can include an outer support frame that includes and/or forms a supra-annular region, a subannular region, and a transannular region coupled therebetween. The supra-annular region can form, for example, an upper collar portion of the outer support frame and can include any number of features configured to engage native tissue, an inner flow control component of the prosthetic valve, and/or a delivery, actuator, and/or retrieval mechanism. The subannular region can form, for example, one or more anchoring elements configured to engage subannular (ventricular) tissue when the prosthetic valve is seated in the native annulus. The transannular region can be coupled between the supra-annular region and the subannular region. The transannular region can form a shape such as a funnel, cylinder, flat cone, or circular hyperboloid when the outer support frame is in an expanded configuration.

In some embodiments, the outer support frame includes and/or is at least partially formed from a wire, a braided wire, or a laser-cut wire frame, and is at least partially covered with a biocompatible material. For example, the outer support frame and/or at least the transannular region thereof can include and/or form a set of compressible wire cells such as braided-wire cells, laser-cut wire cells, photolithography produced wire cells, 3D printed wire cells, wire cells formed from intermittently connected single strand wires in a wave shape, a zig-zag shape, or spiral shape, and/or combinations thereof. In some implementations the compressible wire cells can have an orientation and cell geometry substantially orthogonal to the central axis to reduce or substantially minimize wire cell strain when the outer support frame is in a delivery configuration (e.g., a compressed, rolled, and/or folded configuration).

Any of the prosthetic heart valves described herein (and/ or outer frames thereof) can include a single anchoring element or multiple anchoring elements configured to anchor the valve in the annulus of a native valve (e.g., subannular anchoring elements, supra-annular anchoring elements, and/or a combination thereof). For example, in some implementations, a prosthetic valve and/or outer frame can include one or more of a distal subannular anchoring element configured to engage ventricular tissue distal to the annulus (e.g., can extend into a right ventricular outflow tract (RVOT)); a proximal subannular anchoring element configured to engage ventricular tissue proximal to the annulus (e.g., between the septal leaflets and the posterior leaflets of the heart); a septal anchoring element configured to engage at least one of a native septal wall or a native septal leaflet when the prosthetic heart valve is seated in the annulus (e.g., to pin at least the native septal leaflet away from the coapting leaflets of the prosthetic valve); and/or any other suitable anchoring element. In some implementations, one or more of the subannular anchoring elements can stabilize the valve against intra-annular rolling forces and/or twisting forces that might affect a desired location or positioning of the prosthetic valve within the annulus, (e.g., tilted, angled, twisted, rolled, etc.).

Any of the prosthetic valves and/or outer frames thereof can also include, for example, a distal and/or proximal upper anchoring element configured to be positioned into a supra-annular position in contact with and/or adjacent to supra-annular tissue of the right atrium. In some implementations, the upper anchoring element(s) can be configured to exert a force on supra-annular tissue and the lower anchoring element(s) can be configured to exert a force in an opposite direction on subannular tissue, thereby securing the prosthetic valve in the native annulus. In some implementations, the anchoring element(s) can include and/or can be formed from a wire loop or wire frame, an integrated frame section, and/or a stent, extending from the frame (e.g., about 10-40 mm away from a perimeter of at least a corresponding portion of the frame).

Any of the prosthetic valves described herein can include an inner flow control component that has a leaflet frame with 2-4 flexible leaflets mounted thereon. The 2-4 leaflets are configured to permit blood flow in a first direction through an inflow end of the valve and out an outflow end of the valve, and block blood flow in a second direction, opposite the first direction. The leaflet frame can include any number of panels or walls of diamond-shaped or eye-shaped wire cells made from heat-set shape memory alloy material such as, for example, nickel-titanium alloys (e.g., Nitinol®). The leaflet frame can be configured to be foldable along a z-axis (e.g., a longitudinal axis) from a rounded or cylindrical configuration to a flattened cylinder configuration, and compressible along a vertical y-axis (e.g., a central axis) to a compressed configuration. In some implementations, the leaflet frame can include a pair of hinge areas, fold areas, connection points, etc. that can allow the leaflet frame to be folded flat along the z-axis prior to the leaflet frame being compressed along the vertical y-axis. The leaflet frame can be, for example, a single-piece structure with two or more living hinges (e.g., stress concentration riser(s) and/or any suitable structure configured to allow for elastic/nonpermanent deformation of the leaflet frame) or a two-piece structure where the hinge areas are formed using a secondary attachment method (e.g. sutures, fabrics, molded polymer components, etc. In some embodiments, the inner flow control component in an expanded configuration forms a shape such as a funnel, cylinder, flat cone, or circular hyperboloid. In some embodiments, the inner flow control component has a leaflet frame with a side profile of a flat cone shape having an outer diameter R of about 20-60 mm, an inner diameter r of about 10-50 mm, where diameter R is great than diameter r, and a height of about 5-60 mm. In some embodiments, the leaflet frame is comprised of a wire, a braided wire, or a laser-cut wire frame.

Any of the prosthetic valves and/or components thereof may be fabricated from any suitable biocompatible material or combination of biocompatible materials. For example, an outer valve frame, an inner valve frame (e.g., of an inner flow control component), and/or components thereof may be fabricated from biocompatible metals, metal alloys, polymer coated metals, and/or the like. Suitable biocompatible metals and/or metal alloys can include stainless steel (e.g., 316 L stainless steel), cobalt chromium (Co—Cr) alloys, nickel-titanium alloys (e.g., Nitinol®), and/or the like. Moreover, any of the outer or inner frames described herein can be formed from superelastic or shape-memory alloys such as nickel-titanium alloys (e.g., Nitinol®). Synthetic biocompatible materials can include, for example, polyesters, polyurethanes, elastomers, thermoplastics, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron®), Poly-L-lactic acids (PLLA), polyglycolic acid (PGA), poly(D, L-lactide/glycolide) copolymer (PDLA), silicone polyesters, poly-amides (Nylon), polytetrafluoroethylene (PTFE) (e.g., Tef-lon), elongated PTFE, expanded PTFE, siloxane polymers and/or oligomers, polylactones, and/or the like or block co-polymers using the same.

Any of the prosthetic valves and/or components thereof can include and/or can be formed with one or more bio-compatible coating(s) and/or the like. Suitable polymer coatings can include, for example, polyethylene vinyl acetate (PEVA), poly-butyl methacrylate (PBMA), translute Styrene Isoprene Butadiene (SIBS) copolymer, polylactic acid, polyester, polylactide, D-lactic polylactic acid (DL-PLA), polylactic-co-glycolic acid (PLGA), and/or the like. Some such polymer coatings may form a suitable carrier matrix for drugs such as, for example, Sirolimus, Zotaroli-mus, Biolimus, Novolimus, Tacrolimus, Paclitaxel, Probu-col, and/or the like.

Any of the outer valve frames, inner flow control frames, and/or portions or components thereof can be internally or externally covered, partially or completely, with a natural or synthetic biocompatible and/or biological material such as pericardium, or the like. For example, where a thin, durable synthetic material is contemplated (e.g., for a covering), synthetic polymer materials such expanded PTFE, PET, or polyester (or any of the other materials described herein) may optionally be used. Suitable biological material or tissue used as a covering or the like can include, for example, chemically stabilized pericardial tissue of an ani-mal, such as a cow (bovine pericardium), sheep (ovine pericardium), pig (porcine pericardium), or horse (equine pericardium). For example suitable tissue include, but is not limited to, tissue used in the products Duraguard®, Peri-Guard®, and Vascu-Guard®, products currently used in surgical procedures, products which are marketed as being harvested generally from cattle less than 30 months old, and/or the like. In some implementations, a valve can be configured such that an inner surface of the outer valve frame (e.g., the wireframe cells) is covered with pericardial tissue and an outer surface is covered with a woven synthetic polyester material (or vice versa), or both the inner surface and outer surface is covered with pericardial tissue or a woven synthetic polyester material.

Any method for delivering and/or deploying prosthetic heart valves described herein can include delivery of the prosthetic heart valve to a native annulus of a human heart that includes advancing a delivery catheter to at least one of (i) the tricuspid valve or pulmonary artery of the heart through the inferior vena cava (IVC) via the femoral vein or through the superior vena cava (SVC) via the jugular vein, or (ii) the mitral valve or aortic valve of the heart through a trans-atrial approach (e.g., fossa ovalis or lower), via the IVC-femoral or the SVC jugular approach. The prosthetic valve(s) is/are removably coupled to a portion of the deliv-ery system, placed into a compressed or delivery configu-ration, loaded into a delivery device and/or the delivery catheter, and advanced through a lumen of the delivery catheter. The prosthetic valve(s) can then be released from a distal end of the delivery catheter, which is disposed in an atrium of the heart using the IVC-femoral or the SVC jugular approach. The prosthetic valve(s) is/are allowed to transition to an expanded or released configuration when released from the delivery catheter.

Any method for delivering and/or deploying prosthetic valves described herein can include positioning the valve or a portion thereof in a desired position relative to the native tissue. For example, a method can include inserting a distal subannular anchoring element of a prosthetic valve through an annulus of the native tricuspid valve and into, for example, the RVOT of the right ventricle. In some imple-mentations, the method can include partially inserting a prosthetic valve into the annulus (e.g., of the native tricuspid valve) such that a distal portion thereof contacts native annular tissue while a proximal portion of the prosthetic valve is at least partially compressed and disposed in the delivery catheter. In some embodiments, the method can include rotating the prosthetic heart valve, using a steerable control catheter, a yoke, a set of tethers, an actuator, and/or any other portion of a delivery/deployment system (or combinations thereof), along an axis parallel to the plane of the valve annulus. In some embodiments, the method can include transitioning one or more anchoring elements into a desired position and/or state to engage native tissue sur-rounding at least a portion of the annulus. In some imple-mentations, one or more tissue anchors may be attached to the valve and to native tissue to secure the valve in a desired position.

Any of the delivery and/or deployment systems described herein can include an outer catheter (e.g., a delivery cath-eter), a control catheter, and/or other suitable portion(s) that can include one or more members, components, features, and/or the like configured to facilitate delivery and/or deployment of the valve into an annulus of a native heart valve. For example, in some implementations, a delivery and/or deployment system can include any number of sup-ports or the like that can at least temporarily couple to the prosthetic valve to support, stabilize, actuate, and/or control one or more portions of the prosthetic valve, for example, during deployment. Some such supports or the like can be and/or can include tethers, sutures, tensile or tension mem-bers, rods, cables, wires, catheters, hypotubes, connectors, couplers, etc. In such implementations, the supports can engage one or more portions of the prosthetic valve to support, stabilize, actuate, and/or control the prosthetic valve (e.g., during deployment) and then can be decoupled and/or removed from the prosthetic valve once it is seated in the annulus of the native valve in a desired manner, orien-tation, etc. For example, certain embodiments described herein can include one or more supports that are configured to removably couple to a supra-annular portion of the prosthetic valve to at least partially support, stabilize, actu-ate, control, etc. the prosthetic valve and/or at least one or more portions thereof.

The terminology used herein is for the purpose of describ-ing particular embodiments only and is not intended to limit the full scope of the claims. Unless defined otherwise, technical and scientific terms used herein have the same meanings as commonly understood by one of ordinary skill in the art.

As used herein, the singular forms "a," "an," and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "includ-ing" should be interpreted as "including but not limited to," the term "having" should be interpreted as "having at least,"

etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that any suitable disjunctive word and/or phrase presenting two or more alternative terms, whether in the description, claims, or drawings, contemplate the possibilities of including one of the terms, either of the terms, or both/all terms. For example, the phrase "A or B" will be understood to include the possibilities of "A" or "B" or "A and B."

Any ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The terms "prosthetic heart valve," and/or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place). As used herein, the term "valve" may be used to refer to either a "prosthetic valve" or a "native valve," and will be understood within the specific context in which the term is used.

Prosthetic valves disclosed herein can include a member (e.g., a "frame") that can be seated within a native valve annulus and can be used as a mounting element for a leaflet structure, a flow control component, or a flexible reciprocating sleeve or sleeve-valve. Such a member may or may not include such a leaflet structure or flow control component, depending on the embodiment. Such members can be referred to herein as an "annular support frame," "wire frame," "valve frame," "flange," "collar," "cuff," and/or any other similar terms.

The term "flow control component" can refer in a non-limiting sense to a leaflet structure having 2-, 3-, 4-leaflets of flexible biocompatible material such a treated or untreated pericardium that can be sewn, joined, and/or mounted to an annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves and/or components. For example, such (bio) prosthetics can include ball valves (e.g., Starr-Edwards), bileaflet valves (St. Jude), tilting disc valves (e.g., Bjork-Shiley), stented pericardium heart valves (bovine, porcine, ovine) (Edwards' line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves.

The terms "anchoring element" or "tab" or "arm" refer to structural elements extending from a portion of the valve or valve frame (e.g., extending away from a valve sidewall, body, or collar) to provide an anchoring or stabilizing function to the valve. When used in conjunction with the terms distal, proximal, septal, and/or anterior, it should be understood that the anchoring or stabilizing element so described is attached to and/or integral with the valve (or valve frame) at a distal, proximal, septal, and/or anterior location, respectively. A distal location on a valve refers to a portion of the valve furthest from the practitioner which exits the delivery catheter first, and which can be placed at or near distal subannular native tissue such as the ventricular outflow tract. A proximal location on a valve refers to a portion of the valve closest to the practitioner which exits the delivery catheter last, and which can be placed at or near proximal subannular native tissue such as tissue closest to the inferior vena cava. A septal location on a valve refers to a portion of the valve at a point between a proximal and a distal location, and which can be placed at or near septal subannular native tissue such as the septal leaflet or septal wall. An anterior location on a valve refers to a portion of the valve at a point between a proximal and a distal location, and which can be placed at or near anterior tissue opposite the septal tissue. When used in conjunction with the term "lower," or "subannular" it should be understood that the anchoring or stabilizing element so described is attached to and/or integral with the valve sidewall, body, and/or frame at or along a lower or subannular region of the valve. Conversely, when used in conjunction with the term "upper," or "supra-annular" it should be understood that the anchoring or stabilizing element so described is attached to and/or integral with the valve or frame at or along a supra-annular region, collar, or atrial cuff of the valve.

Any of the disclosed valve embodiments may be delivered by a transcatheter approach. The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein and IVC, via the lumen of the brachial artery and/or vein, via lumen of the carotid artery, via the lumen of the jugular vein and SVC, via the intercostal (rib) and/or sub-xiphoid space, and/or the like. Moreover, transcatheter cardiac access can also include a trans-atrial (e.g., fossa ovalis or lower) approach to the left atrium and/or ventricle. Transcatheter can be synonymous with transluminal and is functionally related to the term "percutaneous" as it relates to delivery of heart valves.

As used herein the terms "orthogonal delivery," "orthogonally delivered," "side-delivery," "side-delivered," "side-deliverable," and/or so forth can be used interchangeably to describe such a delivery method and/or a valve delivered using such a method. The term "orthogonal" refers to an intersecting angle of 90 degrees between two lines or planes (e.g., perpendicular). As used herein, the term "substantially orthogonal" refers to an intersecting angle of 90 degrees plus or minus a suitable tolerance. For example, "substantially orthogonal" can refer to an intersecting angle ranging from 75 to 105 degrees. Orthogonal and/or side delivery of prosthetic valves can be such that the central axis of the valve is substantially orthogonal to the lengthwise or longitudinal axis of the delivery catheter (e.g., the valve is oriented sideways relative to traditional, radially compressed valves).

The mode of cardiac access can be based at least in part on a "body channel," used to define a blood conduit or vessel within the body, and the particular application of the disclosed embodiments of prosthetic valves can determine the body channel at issue. An aortic valve replacement, for example, would be implanted in, or adjacent to, the aortic annulus. Likewise, a tricuspid or mitral valve replacement would be implanted at the tricuspid or mitral annulus, respectively. While certain features described herein may be particularly advantageous for a given implantation site, unless the combination of features is structurally impossible or excluded by claim language, any of the valve embodiments described herein could be implanted in any body channel.

The terms "expandable" and/or "compressible" as used herein may refer to a prosthetic heart valve or a component of the prosthetic heart valve capable of expanding and/or compressing from a first size or configuration to a second size or configuration. For example, a prosthetic valve may be "compressible" to a delivery size or configuration and/or "expandable" to an implantation or deployment size or configuration. Therefore, unless the context clearly indicates otherwise, an "expandable"/"compressible" structure is not intended to refer to a structure that might undergo slight expansion/compression such as, for example, from a change in temperature or other such incidental cause. Conversely, "non-expandable"/"non-compressible" should not be interpreted to mean completely rigid or a dimensionally stable, as some slight expansion/compression of conventional "non-expandable"/"non-compressible" heart valves, for example, may be observed.

The prosthetic valves disclosed herein and/or components thereof are generally capable of transitioning between two or more configurations, states, shapes, and/or arrangements. For example, prosthetic valves described herein can be compressible and/or expandable between any suitable number of configurations. Various terms can be used to describe or refer to these configurations and are not intended to be limiting unless the context clearly states otherwise. For example, a prosthetic valve can be described as being placed in a "delivery configuration," which may be any suitable configuration that allows or enables delivery of the prosthetic valve. Examples of delivery configurations can include a compressed configuration, a folded configuration, a rolled configuration, and/or similar configuration or any suitable combinations thereof. Similarly, a prosthetic valve can be described as being placed in an "expanded configuration," which may be any suitable configuration that is not expressly intended for delivery of the prosthetic valve. Examples of expanded configuration can include a released configuration, a relaxed configuration, a deployed configuration, a non-delivery configuration, and/or similar configurations or any suitable combinations thereof. Some prosthetic valves described herein and/or components or features thereof can have a number of additional configurations that can be associated with various modes, levels, states, and/or portions of actuation, deployment, engagement, etc. Examples of such configurations can include an actuated configuration, a seated configuration, a secured configuration, an engaged configuration, and/or similar configurations or any suitable combinations thereof. While specific examples are provided above, it should be understood that they are not intended to be an exhaustive list of configurations. Other configurations may be possible. Moreover, various terms can be used to describe the same or substantially similar configurations and thus, the use of particular terms are not intended to be limiting and/or to the exclusion of other terms unless the terms and/or configurations are mutually exclusive, or the context clearly states otherwise.

The examples and/or embodiments described herein are intended to facilitate an understanding of structures, functions, and/or aspects of the embodiments, ways in which the embodiments may be practiced, and/or to further enable those skilled in the art to practice the embodiments herein. Similarly, methods and/or ways of using the embodiments described herein are provided by way of example only and not limitation. Specific uses described herein are not provided to the exclusion of other uses unless the context expressly states otherwise. For example, any of the prosthetic valves described herein can be used to replace a native valve of a human heart including, for example, a mitral valve, a tricuspid valve, an aortic valve, and/or a pulmonary valve. While some prosthetic valves are described herein in the context of replacing a native mitral valve or a native tricuspid valve, it should be understood that such a prosthetic valve can be used to replace any native valve unless expressly stated otherwise or unless one skilled in the art would clearly recognize that one or more components and/or features would otherwise make the prosthetic valve incompatible for such use. Specific examples, embodiments, methods, and/or uses described herein should not be construed as limiting the scope of the inventive concepts herein. Rather, examples and embodiments are provided so that this disclosure will be thorough and complete, and will fully convey the scope of the inventive concepts to those skilled in the art.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not obscure the embodiments herein. Like numbers refer to like elements throughout. A discussion of various embodiments, components, and/or features of prosthetic valve(s) (e.g., side-deliverable, transcatheter prosthetic heart valves) is followed by a discussion of delivery/deployment systems and methods of using such systems to deliver and/or deploy a prosthetic valve into an annulus of a native heart valve.

FIGS. 1-6 are various schematic illustrations of a side-deliverable transcatheter prosthetic heart valve 100 (also referred to herein as "prosthetic valve" or simply "valve") according to an embodiment. As described in further detail herein, the valve 100 generally includes an annular support frame 110 and a flow control component 150 mounted within the annular support frame 110. In addition, FIGS. 1-6 illustrate at least a portion of a delivery/deployment system 180 that can at least temporarily couple to and/or otherwise engage the valve 100 and/or portions thereof to facilitate the delivery and/or deployment of the valve 100 into a desired location of a body. For example, delivery/deployment system 180 can be used to deliver and deploy the prosthetic valve 100 in an annulus of a native valve of a human heart (e.g., a tricuspid, mitral, aortic, and/or pulmonary valve of the human heart) and once deployed, the prosthetic valve 100 is configured to permit blood flow in a first direction (e.g., through or via the flow control component 150) from an inflow end of the prosthetic valve 100 to an outflow end of the prosthetic valve 100 and to block blood flow in a second direction, opposite the first direction. Thus, the prosthetic valve 100 can be configured to supplement and/or replace the functioning of the native valve. In some embodiments, the valve 100 and/or the delivery/deployment system 180 can be similar to and/or substantially the same as the valve(s) and/or the delivery/deployment system(s) described in WIPO Patent Publication No. WO 2021/040996 (referred to herein as "the '996 PCT"), filed Aug. 6, 2020, entitled "Side-Deliverable Transcatheter Prosthetic Valves and Methods for Delivering and Anchoring the Same" and WIPO Patent Publication No. WO 2021/035032 (referred to herein as "the '032 PCT"), filed Aug. 20, 2020, entitled "Delivery and Retrieval Devices and Methods for Side-Deliverable Transcatheter Prosthetic Valves," the disclosure of each of which is incorporated herein by reference in its entirety.

Figure 3:
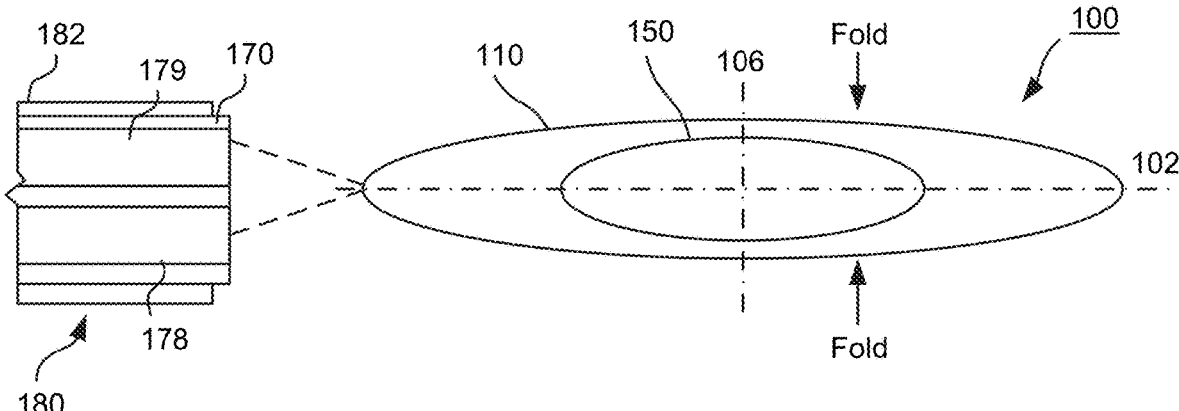
Figure 4:
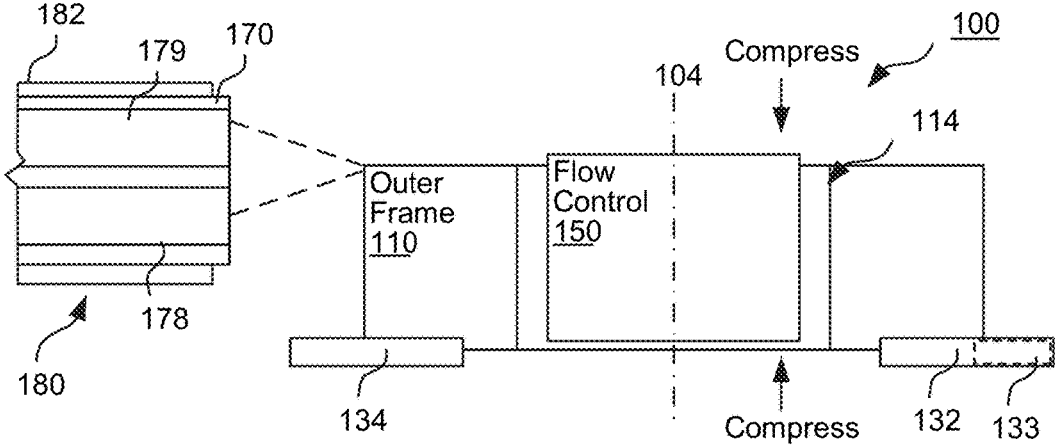

The prosthetic valve 100 is compressible and expandable between an expanded configuration (FIGS. 1 and 2) for implanting at a desired location in a body (e.g., a human heart) and a compressed or delivery configuration (FIGS. 3 and 4) for introduction into the body via, for example, a delivery catheter 182 of the delivery/deployment system 180. The prosthetic valve 100 can be compressible and expandable in at least one direction relative to a longitudinal axis 102 of the valve 100 (also referred to herein as "horizontal axis," "long-axis," or "lengthwise axis"). For example, the valve 100 can compressible/expandable along a central axis 104, with a first height or size along the central axis 104 when in the expanded configuration (FIG. 1) and a second height or size, less than the first height or size, along the central axis 104 when in the compressed configuration (FIG. 3). In some embodiments, the prosthetic valve 100 can be compressible and expandable in at least two directions relative to the longitudinal axis 102 of the valve 100. For example, the valve 100 can be compressible/expandable along the central axis 104 (as just described) and compressible/expandable along a lateral axis 106 that is perpendicular to both the longitudinal axis 102 and the central axis 104 (see e.g., FIGS. 1 and 2). In such embodiments, the valve 100 can have the first height and a first width when in the expanded configuration (FIGS. 1 and 2) and can have a second height and a second width—less than the first height and first width, respectively—when in the compressed configuration (FIGS. 3 and 4).

Figure 6:
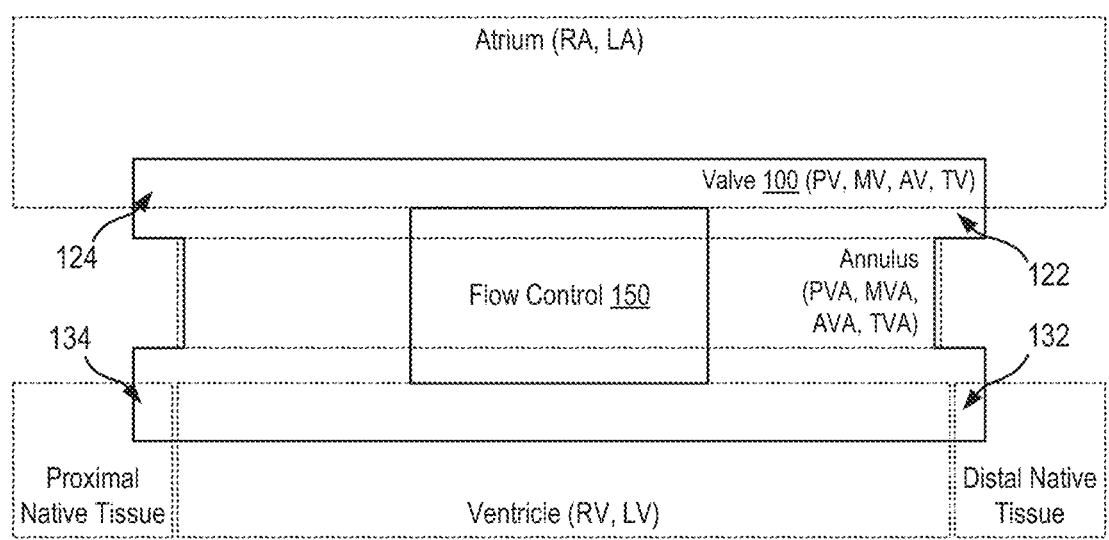

When in the expanded configuration shown in FIGS. 1, 2, and 6, the valve 100 has an extent in any direction orthogonal or lateral to the longitudinal axis 102 (e.g., along the central axis 104 and/or the lateral axis 106) that is larger than a diameter of the lumen of the delivery catheter 182 used to deliver the valve 100. For example, in some embodiments, the valve 100 can have an expanded height (e.g., along the central axis 104) of 5-60 mm. In some embodiments, the valve 100 can have an expanded length (e.g., along the longitudinal axis 102) and width (e.g., along the lateral axis 106) of about 20-80 mm, or about 40-80 mm. When in the compressed configuration shown in FIGS. 3 and 4, the valve 100 has an extent in any direction orthogonal or lateral to the longitudinal axis 102 (e.g., along the central axis 104 and/or the lateral axis 106) that is smaller than the diameter of the lumen of the delivery catheter 182, allowing the valve 100 to be delivered therethrough. For example, in some embodiments, the valve 100 can have a compressed height (e.g., along the central axis 104) and a compressed width (e.g., along the lateral axis 106) of about 5-15 mm, about 8-12 mm, or about 9-10 mm. The valve 100 can be compressed by compressing, rolling, folding, and/or any other suitable manner, or combinations thereof. In some implementations, the length of the valve 100 (e.g., along the longitudinal axis 102) is not compressed for or during delivery. Rather, in some implementations, the length of the valve 100 can be increased in response to compression of the valve 100 along the central axis 104 and/or the lateral axis 106.

In some embodiments, the valve 100 (and/or at least a portion thereof) may be heat-shaped and/or otherwise formed into any desired shape such as, for example, a roughly tubular shape, a roughly hourglass shape, and/or the like. In some embodiments, the valve 100 can include a supra-annular section or region (e.g., an upper atrial cuff or flange for atrial sealing), a subannular section or region (e.g., a lower ventricle cuff or flange for ventricular sealing), and a transannular section or region (e.g., a body section, a tubular section, a cylindrical section, etc.) disposed therebetween. The transannular region can have an hourglass cross-section for about 60-80% of the circumference to conform to the native annulus along the posterior and anterior annular segments while remaining substantially vertically flat along 20-40% of the annular circumference to conform to the septal annular segment.

While the valve 100 is shown in FIGS. 1-6 as having a given shape (a generic shape), it should be understood that the size and/or shape of the valve 100 (and/or at least a portion thereof) can be based on a size and/or shape of the anatomical structures of the native tissue. For example, the valve 100 can be centric (e.g., radially symmetrical relative to a central axis 104 (y-axis)) or eccentric (e.g., radially asymmetrical relative to the central axis 104). In some eccentric embodiments, the valve 100, or an outer frame thereof, may have a complex shape determined by the anatomical structures where the valve 100 is being mounted. For example, in some instances, the valve 100 may be deployed in an annulus of a native tricuspid valve having a circumference in the shape of a rounded ellipse with a substantially vertical septal wall, which is known to enlarge in disease states along an anterior-posterior line. In some instances, the valve 100 may be deployed in an annulus of a native mitral valve (e.g., near the anterior leaflet) having a circumference in the shape of a rounded ellipse with a substantially vertical septal wall, which is known to enlarge in disease states.

As such, the valve 100 can have a complex shape that is determined, at least in part, by the native annulus and/or a disease state of the native valve. By way of example, the valve 100 or the outer frame thereof may have a D-shape (viewed from the top) so the flat or substantially flat portion can be matched to the anatomy in which the valve 100 will be deployed (e.g., a substantially vertical septal wall). In some embodiments, the valve 100 or the outer frame thereof can have a circumference in the shape of a rounded ellipse, such as a hyperbolic paraboloid, to account for the positions of native septal, anterior, and/or posterior leaflets, and/or the native septal wall; to avoid native electrical bundles such as the atrioventricular (A-V) node and/or A-V node-related structures like the Triangle of Koch, AV bundle, etc.; to avoid interference with coronary blood flow such as the coronary sinus; to accommodate variances in the septal wall that is known to be substantially vertical but that enlarges along the anterior-posterior axis toward the free wall in disease states; and/or the like.

As shown, the valve 100 generally includes the annular support frame 110 and the flow control component 150 mounted within the annular support frame 110. In addition, the valve 100 and/or at least the annular support frame 110 of the valve 100 can include, can couple to, and/or can otherwise engage the delivery/deployment system 180. The annular support frame 110 (also referred to herein as "valve frame," "wire frame," "outer frame," "support frame," "frame," etc.) can have a supra-annular region 120, a subannular region 130, and a transannular region 112, disposed and/or coupled therebetween. In some embodiments, the frame 110 can be monolithically and/or unitarily constructed. In some embodiments, one or more of the supra-annular region 120, the subannular region 130, and/or the transannular region 112 can be separate, independent, and/or modular components that are coupled to collectively form the frame 110. For example, in some embodiments, the supra-annular region 120 can be an atrial collar, cuff, portion, and/or the like coupled to a top, upper, and/or supra-annular edge of the transannular region 112 and the subannular region 130 can be a ventricular collar, cuff, portion, and/or the like coupled to a bottom, lower, and/or subannular edge of the transannular region 112. Alternatively, the subannular region 130 can be and/or can be formed by a bottom, lower, and/or subannular portion or section of the transannular region 112.

In some implementations, a modular and/or at least partially modular configuration can allow the frame 110 to be adapted to a given size and/or shape of the anatomical structures where the valve 100 is being mounted. For example, one or more of the supra-annular region 120, the subannular region 130, and/or the transannular region 112 can be designed and/or adapted so that that the support frame 110 has any desirable height, outer diameter, and/or inner diameter such as any of those described above. Moreover, such a modular configuration can allow the frame 110 to bend, flex, compress, fold, roll, and/or otherwise reconfigure without plastic or permanent deformation thereof. For example, the frame 110 is compressible to a compressed or delivery configuration for delivery and when released it is configured to return to its original shape (uncompressed, expanded, or released configuration) substantially without plastic or permanent deformation.

The support frame 110 and/or the supra-annular region 120, subannular region 130, and/or transannular region 112 can be formed from or of any suitable material. In some embodiments, the frame 110 and/or one or more portions or regions thereof can be formed from or of a shape-memory or superelastic metal, metal alloy, plastic, and/or the like. For example, the frame 110 (e.g., one or more of the supra-annular region 120, the subannular region 130, and the transannular region 112) can be formed from or of Nitinol or the like. In some embodiments, the frame 110 (and/or any of the regions thereof) can be laser cut from a Nitinol sheet or tube. In other embodiments, the frame 110 (and/or any of the regions thereof) can be formed of or from a Nitinol wire that is bent, kink, formed, and/or manipulated into a desired shape. In still other embodiments, the frame 110 (and/or any of the regions thereof) can be formed of or from a desired material using any suitable additive or subtractive manufacturing process such as those described above. Moreover, the frame 110 and/or one or more of the supra-annular region 120, the subannular region 130, and the transannular region 112 can be formed of or from a metal or other structural frame material, which in turn, is covered by a biocompatible material such as, for example, pericardium tissue (e.g., Dura-Guard®, Peri-Guard®, Vascu-Guard®, etc.), polymers (e.g., polyester, Dacron®, etc.), and/or the like, as described above.

The supra-annular region 120 of the frame 110 can be and/or can form, for example, a cuff or collar that can be attached or coupled to an upper edge or upper portion of the transannular region 112. When the valve 100 is deployed within a human heart, the supra-annular region 120 can be an atrial collar that is shaped to conform to the native deployment location. In a tricuspid and/or mitral valve replacement, for example, the supra-annular region 120 (e.g., atrial collar) can have various portions configured to conform to the native valve and/or a portion of the atrial floor surrounding the tricuspid and/or mitral valve, respectively. In some implementations, the supra-annular region 120 can be deployed on the atrial floor to direct blood from the atrium into the flow control component 150 of the valve 100 and to seal against blood leakage (perivalvular leakage) around the frame 110 (e.g., through the annulus but outside of the flow control component 150).

In some embodiments, the supra-annular region 120 can be and/or can include a wire frame that is laser cut out of any suitable material. In some embodiments, the supra-annular region 120 can be formed from a tube or sheet of a shape-memory or superelastic material such as, for example, Nitinol and, for example, heat-set into a desired shape and/or configuration. In some embodiments, forming the supra-annular region 120 in such a manner can allow the supra-annular region 120 to bend, flex, fold, compress, and/or otherwise reconfigure substantially without plastically deforming and/or without fatigue that may result in failure or breaking of one or more portions thereof. Moreover, the wire frame of the supra-annular region 120 can be covered by any suitable biocompatible material such as any of those described above.

The supra-annular region 120 includes a distal portion and a proximal portion. In some embodiments, the distal portion can be and/or can include a distal supra-annular anchoring element and/or the like that can engage supra-annular native tissue on a distal side of the annulus as the prosthetic valve 100 is seated into the annulus. In some embodiments, the proximal portion can be and/or can include a proximal supra-annular anchoring element and/or the like that can engage supra-annular native tissue on a proximal side of the annulus as the prosthetic valve 100 is seated in the annulus. In some embodiments, the distal portion and/or the distal supra-annular anchoring element can be sized and/or shaped to correspond to a size and/or shape of the distal portion of the atrial floor of the heart in which the prosthetic valve 100 is disposed. Similarly, the proximal portion and/or the proximal supra-annular anchoring element can be sized and/or shaped to correspond to a size and/or shape of a proximal portion of the atrial floor of the heart. In some embodiments, the distal portion (or the distal supra-annular anchoring element) and/or the proximal portion (or the proximal supra-annular anchoring element) can be actuated to transition between two or more configurations and/or states (e.g., during deployment or the like), as described in further detail herein.

Although not shown in FIGS. 1-6, the supra-annular region 120 can be shaped and/or formed to include any number of features configured to engage native tissue and/or one or more other portions of the valve 100, the delivery/deployment system 180, and/or the like. For example, in some embodiments, the supra-annular region 120 can include and/or can form an outer portion and an inner portion that is suspended from and/or coupled to the outer portion. In some implementations, the outer portion can be sized and/or shaped to engage native tissue, the inner portion can provide structure for mounting the flow control component 150 to the support frame 110, and one or more coverings, drums, spacers, struts, splines, and/or structures can be disposed therebetween. In some implementations, a portion of the supra-annular region 120 can be at least temporarily coupled to and/or can at least temporarily receive a portion of the delivery/deployment system 180, at least a portion of an actuator, at least a portion of a guidewire (or guidewire catheter), and/or the like (as described in further detail herein).

The transannular region 112 of the support frame 110 is coupled to the supra-annular region 120 and extends from the supra-annular region 120 and at least partially through the annulus of the native valve when the prosthetic valve 100 is seated therein. In some embodiments, the transannular region 112 can be coupled to the supra-annular region 120 such that a desired amount of movement and/or flex is allowed therebetween (e.g., welded, bonded, sewn, bound, and/or the like). For example, in some implementations, the transannular region 112 and/or portions thereof can be sewn and/or sutured to the supra-annular region 120 (and/or portions thereof).

The transannular region 112 can be shaped and/or formed into a ring, a cylindrical tube, a conical tube, D-shaped tube, and/or any other suitable annular shape. In some embodiments, the transannular region 112 may have a side profile of a flat-cone shape, an inverted flat-cone shape (narrower at top, wider at bottom), a concave cylinder (walls bent in), a convex cylinder (walls bulging out), an angular hourglass, a curved and/or graduated hourglass, and/or a ring or cylinder having a flared top, flared bottom, or both. In some embodiments, the transannular region 112 can have a shape and/or size that is at least partially based on a size, shape, and/or configuration of the supra-annular region 120 (and/or the subannular region 130) and/or the native annulus in which it is configured to be deployed. For example, the transannular region 112 can have an outer circumference surface for engaging native annular tissue that may be tensioned against an inner aspect of the native annulus to provide structural patency to a weakened native annular ring. Moreover, the transannular region 112 can form and/or define an aperture or central channel 114 that extends along the central axis 104 (e.g., the y-axis). The central channel 114 (e.g., a central axial lumen or channel) can be sized and configured to receive the flow control component 150 across at least a portion of a diameter of the central channel 114.

In some embodiments, the transannular region 112 can be and/or can include a wire frame that is laser cut out of any suitable material. For example, the transannular region 112 can be formed from a tube or sheet of a shape-memory or superelastic material such as, for example, Nitinol and, for example, heat-set into a desired shape and/or configuration. Although not shown in FIGS. 1-6, in some embodiments, the transannular region 112 can include and/or can be formed with two laser cut halves that can be formed into a desired shape and/or configuration and coupled together to form the transannular region 112. The transannular region 112 can be formed to include a set of compressible wire cells having an orientation and/or cell geometry substantially orthogonal to the central axis 104 (FIG. 1) to limit and/or substantially minimize wire cell strain when the transannular region 112 is in a vertical compressed configuration, a rolled and compressed configuration, or a folded and compressed configuration. In some embodiments, forming the transannular region 112 in such a manner can allow the transannular region 112 to bend, flex, fold, deform, and/or otherwise reconfigure (substantially without plastic deformation and/or undue fatigue) in response to lateral folding along or in a direction of the lateral axis 106 (FIG. 4) and/or vertical compression along or in a direction of the central axis 104 (FIG. 3), as described in further detail herein.

As described above with reference to the supra-annular region 120, the wire frame of the transannular region 112 can be covered by any suitable biocompatible material such as any of those described above. In some implementations, the wire frame of at least the supra-annular region 120 and transannular region 112 can be flexibly coupled (e.g., sewn or sutured) and then collectively or separately covered in the biocompatible material. Said another way, at least the supra-annular region 120 and the transannular region 112 can be covered with the biocompatible material prior to being coupled or after being coupled. In embodiments in which the wire frames are covered after being coupled, the biocompatible material can facilitate and/or support the coupling therebetween.

The subannular region 130 of the frame 110 can be and/or can form, for example, a cuff or collar along an end of the transannular region 112 opposite the supra-annular region 120. For example, when the valve 100 is deployed within a human heart, the subannular region 130 can be and/or can form a ventricular collar that is shaped to conform to the native deployment location. In a tricuspid and/or mitral valve replacement, for example, the subannular region 130 or collar can have various portions configured to conform to the native valve and/or a portion of the ventricular ceiling surrounding the tricuspid and/or mitral valve, respectively. In some implementations, the subannular region 130 or at least a portion thereof can engage the ventricular ceiling surrounding the native annulus to secure the valve 100 in the native annulus, to stabilize the valve 100 in the annulus, to prevent dislodging of the valve 100, to sandwich or compress the native annulus or adjacent tissue between the supra-annular region 120 and the subannular region 130 (or lower portion of the transannular region 112), and/or to seal against blood leakage (perivalvular leakage and/or regurgitation during systole) around the frame 110.

In some embodiments, the subannular region 130 is a lower or subannular portion of the transannular region 112 (e.g., the transannular region 112 and the subannular region 130 are monolithically and/or unitarily formed). Said another way, a lower or subannular portion of the transannular region 112 can form and/or include the subannular region 130. In other embodiments, the subannular region 130 is a separate and/or independent component that can be attached or coupled to a lower edge or portion of the transannular region 112, as described above with reference to the supra-annular region 120. In such embodiments, for example, the subannular region 130 can be and/or can include a wire frame that is laser cut out of any suitable material such as a shape-memory or superelastic material like Nitinol, heat-set into a desired shape and/or configuration, covered by any suitable biocompatible material, and attached to a lower edge of the transannular region 112, as described above with reference to the supra-annular region 120. In some implementations, forming the subannular region 130 in such a manner can allow the subannular region 130 to bend, flex, fold, compress, and/or otherwise reconfigure substantially without plastically deforming and/or without undue or undesirable fatigue that may result in failure or breaking of one or more portions thereof.

The subannular region 130 of the frame 110 can be shaped and/or formed to include any number of features configured to engage native tissue, one or more other portions of the valve 100, one or more portions of the delivery/deployment system 180, one or more actuators (not shown), and/or the like. For example, as shown in FIG. 1, the subannular region 130 can include and/or can form a distal portion having a distal anchoring element 132 and a proximal portion having a proximal anchoring element 134. In some embodiments, each of the distal anchoring element 132 and the proximal anchoring element 134 are integrally and/or monolithically formed with the subannular region 130 and/or the lower or subannular portion of the transannular region 112.

In some embodiments, the distal anchoring element 132 optionally can include a guidewire coupler 133 configured to selectively engage and/or receive a portion of a guidewire or a portion of a guidewire catheter. The guidewire coupler 133 is configured to allow a portion of the guidewire or guidewire catheter to extend through an aperture of the guidewire coupler 133, thereby allowing the valve 100 to be advanced over or along the guidewire and/or guidewire catheter during delivery and deployment.

The distal anchoring element 132 is configured to engage a desired portion of the native tissue on a distal side of the native annulus to facilitate the seating, mounting, and/or deploying of the valve 100 in the annulus of the native valve. For example, in some implementations, the distal anchoring element 132 can be a projection or protrusion extending from the frame 110 (e.g., the subannular region 130 and/or the lower portion of the transannular region 112) and into a distal subannular position relative to the annulus (e.g., the RVOT for tricuspid valve replacement, and/or the like). In such implementations, the distal anchoring element 132 can be shaped and/or biased such that the distal anchoring element 132 exerts a force on the subannular tissue operable to at least partially secure, stabilize, and/or anchor the distal end portion of the valve 100 in the native annulus. In some embodiments, the distal anchoring element 132 can extend from the distal portion of the subannular region 130 (or lower portion of the transannular region 112) by about 10-40 mm.

The proximal anchoring element 134 is configured to engage subannular tissue on a proximal side of the native annulus to facilitate the deploying, seating, mounting, and/or securing of the valve 100 in the annulus. In some embodiments, the proximal anchoring element 134 can be an anchoring element having a substantially fixed configuration. In such embodiments, the proximal anchoring element 134 can be flexible and/or movable through a relatively limited range of motion but otherwise has a single, fixed configuration. In some such embodiments, the proximal anchoring element 134 can extend from the proximal portion of the subannular region 130 (or lower portion of the transannular region 112) by about 10-40 mm.

In other embodiments, the proximal anchoring element 134 can be configured to transition, move, and/or otherwise reconfigure between two or more configurations. For example, the proximal anchoring element 134 can be transitioned between a first configuration in which the proximal anchoring element 134 extends from the subannular region 130 a first amount or distance and a second configuration in which the proximal anchoring element 134 extends from the subannular region 130 a second amount or distance, different from the first amount or distance. In some embodiments, the proximal anchoring element 134 can have a first configuration in which the proximal anchoring element 134 is in a compressed, contracted, retracted, undeployed, folded, and/or restrained state (e.g., in a position that is near, adjacent to, and/or in contact with the transannular region 112 and/or the supra-annular region 120 of the frame 110), and a second configuration in which the proximal anchoring element 134 is in an expanded, extended, deployed, unfolded, and/or unrestrained state (e.g., extending away from the transannular region 112). In some implementations, the proximal anchoring element 134 in the expanded or deployed configuration (e.g., the second configuration) can extend from the transannular region 112 by about 10-40 mm and in the compressed or undeployed configuration (e.g., the first configuration) can be in contact with the transannular region 112 or can extend from the transannular region 112 by less than about 10 mm. In some implementations, at least a portion of the transannular region 112 can be at least partially reconfigured based on the state and/or configuration of the proximal anchoring element 134. For example, placing the proximal anchoring element 134 in a compressed state or configuration can also at least partially compress or reconfigure at least a proximal portion of the transannular region 112. Moreover, in some implementations, the proximal anchoring element 134 can be transitioned from the first configuration to the second configuration in response to actuation of an actuator, tensile member, portion of the delivery/deployment system 180, and/or the like, as described in further detail herein.

In some implementations, the proximal anchoring element 134 can be transitioned from the first configuration to the second configuration during deployment to selectively engage native tissue, chordae, trabeculae, annular tissue, leaflet tissue, and/or any other anatomic structures to aid in the securement of the valve 100 in the native annulus. The proximal anchoring element 134 (and/or the distal anchoring element 132) can include any suitable feature, surface, member, etc. configured to facilitate the engagement between the proximal anchoring element 134 (and/or the distal anchoring element 132) and the native tissue. For example, in some embodiments, the proximal anchoring element 134 can include one or more features configured to engage and/or become entangled in the native tissue, chordae, trabeculae, annular tissue, leaflet tissue, and/or any other anatomic structures when in the second configuration.

Although not shown in FIGS. 1-6, the subannular region 130 can include and/or form any number of additional anchoring elements such as, for example, a septal anchoring element and/or the like. For example, the subannular region 130 can include a posterior-septal (PS) tab or anchoring element that can engage posterior-septal tissue to help stabilize the valve in the annulus of the native valve. In some embodiments, a septal subannular anchoring element can be included and configured to engage subannular septal tissue, septal leaflet tissue, and/or any other suitable tissue at, near, and/or along the septum of the heart. In some implementations, when the valve 100 is at least partially inserted into the annulus, the septal anchoring element can extend down the septal wall to pin the native septal leaflet away from, for example, the coapting leaflets of the prosthetic valve 100 and/or to stabilize the valve against any intra-annular rolling forces and/or any intra-annular twisting forces that might affect a desired location or positioning of the prosthetic valve within the annulus, (e.g., tilted, angled, twisted, rolled, etc.).

In some embodiments, anchoring elements included in or extending from the subannular region 130 can be configured with a predetermined atrial or ventricular bias, which in some implementations, may be designed, selected, and/or tuned to allow the subannular anchoring elements to engage the native ventricular tissue with a desired amount of force. For example, in some embodiments, the distal subannular anchoring element 132 may have a slight atrial bias meaning the distal anchoring element 132 is disposed at or extends at an angle in a supra-annular direction (e.g., toward the annulus). In other embodiments, the distal subannular anchoring element 132 may have a slight ventricular bias meaning the distal anchoring element 132 is disposed at or extends at an angle in a subannular direction (e.g., away from the annulus). In still other embodiments, the distal subannular anchoring element 132 may have a neutral bias meaning the distal anchoring element 132 is not disposed at angle and/or otherwise extends in a substantially straight or neutral manner. Similarly, any other subannular anchoring element may have an atrial, ventricular, or neutral bias that can be designed, selected, and/or tuned to allow the anchoring element(s) to engage the native ventricular tissue with a desired amount of force.

Although not shown in FIGS. 1-6, the frame 110 may also have and/or form additional functional elements (e.g., loops, anchors, attachment points, etc.) for attaching accessory components such as biocompatible covers, tissue anchors, releasable deployment/retrieval controls (e.g., an actuator, a tensile member, a torque cable, a hypotube, a portion of the delivery/deployment system 180, support members or tethers, and/or other suitable guides, knobs, attachments, rigging, etc.) and so forth.

The flow control component 150 can refer in a non-limiting sense to a device for controlling fluid flow therethrough. In some embodiments, the flow control component 150 can be a leaflet structure having two, three, four, or more leaflets, made of flexible biocompatible material such a treated or untreated pericardium. The leaflets can be sewn or joined to a support structure such as an inner frame, which in turn, can be sewn or joined to the valve frame 110 (i.e., an outer frame). The leaflets can be configured to move between an open and a closed or substantially sealed state to allow blood to flow through the flow control component 150 in a first direction through an inflow end of the valve 100 and block blood flow in a second direction, opposite to the first direction, through an outflow end of the valve 100. For example, the flow control component 150 can be configured such that the valve 100 functions, for example, as a heart valve, such as a tricuspid valve, mitral valve, aortic valve, or pulmonary valve, which can open to blood flowing during diastole from atrium to ventricle, and that can close from systolic ventricular pressure applied to the outer surface.

The inner frame and/or portions or aspects thereof can be similar in at least form and/or function to the valve frame 110 (i.e., outer frame) and/or portions or aspects thereof. For example, the inner frame can be a laser cut frame formed from or of a shape-memory material such as Nitinol. Moreover, the inner frame can be compressible for delivery and configured to return to its original (uncompressed) shape when released (e.g., after delivery). In some embodiments, the inner frame can include multiple portions or parts that are coupled together to collectively form the inner frame. Such an arrangement can allow the inner frame to transition between a compressed and uncompressed state without undue or undesirable plastic deformation, fatigue, and/or the like. In some embodiments, the inner frame can include and/or can form any suitable number of compressible, elastically deformable diamond-shaped or eye-shaped wire cells, and/or the like. The wire cells can have an orientation and cell geometry substantially orthogonal to an axis of the flow control component 150 to limit or substantially minimize wire cell strain when the inner frame is in a compressed configuration.

In some embodiments, the flow control component 150 and/or the inner frame thereof can have a substantially cylindrical or tubular shape when the valve 100 is in the expanded configuration (see e.g., FIG. 2) and can be configured to elastically deform when the valve 100 is placed in the compressed configuration (see e.g., FIGS. 3 and 4). Although not shown in FIGS. 1-6, in some embodiments, the inner frame of the flow control component 150 can include and/or can be formed with two halves that can be coupled together to allow the inner frame to elastically deform in response to lateral compression or folding along or in a direction of the lateral axis 106 (FIG. 3), as described in further detail herein.

As shown in FIGS. 1-6, the flow control component 150 is mounted within the central channel 114 of the frame 110. More specifically, the flow control component 150 is mounted and/or coupled to the supra-annular region 120 (e.g., an inner portion thereof) and is configured to extend into and/or through the central channel 114 formed and/or defined by the transannular region 112. In some embodiments, the flow control component 150 can be coupled to the supra-annular region 120 via tissue, a biocompatible mesh, one or more woven or knitted fabrics, one or more superelastic or shape-memory alloy structures, which is sewn, sutured, and/or otherwise secured to a portion of the supra-annular region 120. In some embodiments, the flow control component 150 can be coupled to the supra-annular region 120 such that a portion of the flow control component 150 is disposed above and/or otherwise extends beyond the supra-annular region 120 (e.g., extends away from the annulus in the direction of the atrium). In some embodiments, the portion of the flow control component 150 extending above and/or beyond the supra-annular region 120 can form a ridge, ledge, wall, step-up, and/or the like. In some implementations, such an arrangement can facilitate ingrowth of native tissue over the supra-annular region 120 without occluding the flow control component 150.

The flow control component 150 can be at least partially disposed in the central channel 114 such that the axis of the flow control component 150 that extends in the direction of blood flow through the flow control component 150 is substantially parallel to the central axis 104 of the frame 110. In some embodiments, the arrangement of the support frame 110 can be such that the flow control component 150 is centered within the central channel 114. In other embodiments, the arrangement of the support frame 110 can be such that the flow control component 150 is off centered within the central channel 114. In some embodiments, the central channel 114 can have a diameter and/or perimeter that is larger than a diameter and/or perimeter of the flow control component 150. Although not shown in FIGS. 1-6, in some embodiments, the valve 100 can include a spacer or the like that can be disposed within the central channel 114 adjacent to the flow control component 150. In other embodiments, a spacer can be a cover, or the like coupled to a portion of the frame 110 and configured to cover a portion of the central channel 114. In some instances, the spacer can be used to facilitate the coupling of the flow control component 150 to the frame 110.

Figure 5:
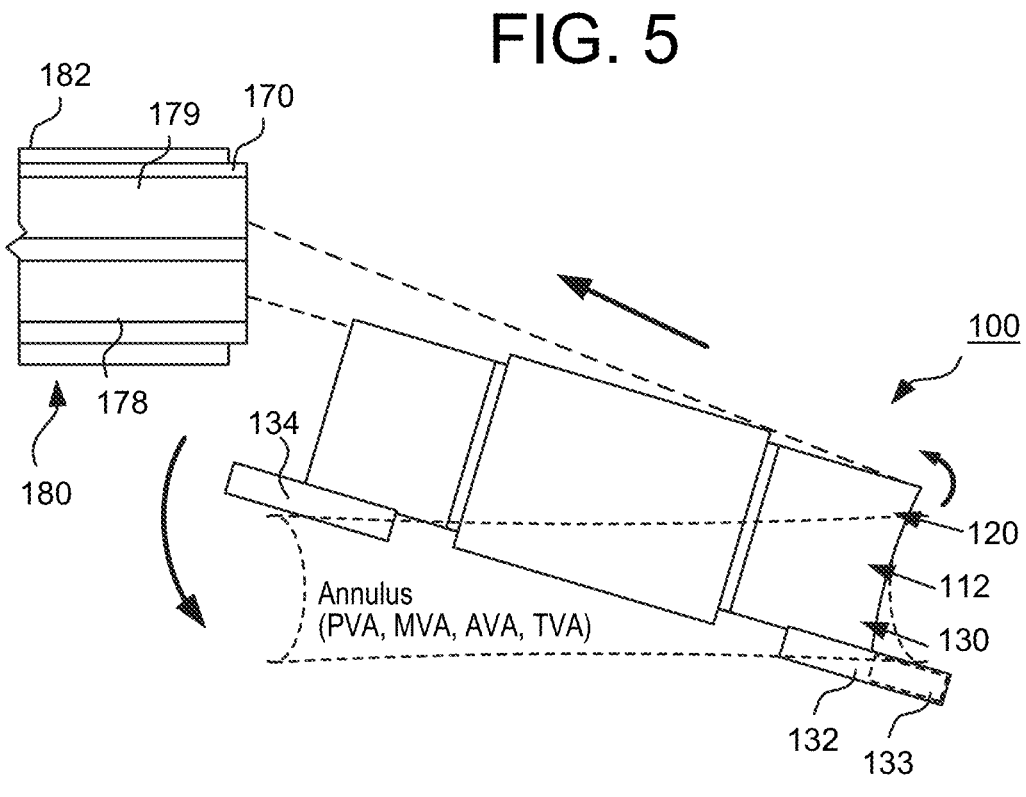

FIG. 5 shows the delivery/deployment system 180 being used to deploy the valve 100 and FIG. 6 shows the valve 100 seated in an annulus of a native heart valve after delivery and deployment. As described above, the prosthetic valve 100 can be a replacement prosthetic valve for any of the native valves of the human heart—the pulmonary valve, mitral valve, aortic valve, and/or tricuspid valve (PV, MV, AV, TV). More specifically, the valve 100 is configured for transcatheter, orthogonal/side delivery through the delivery catheter 182 to the desired location in the body. During delivery through the delivery catheter 182, the valve 100 is compressed in an orthogonal and/or lateral direction relative to the dimensions of the valve 100 in the expanded configuration (e.g., along the central axis 104 and/or the lateral axis 106, as described above) and the longitudinal axis 102 of the valve 100 is substantially parallel to a longitudinal axis of the delivery catheter 182. In some embodiments, the devices and methods for/of delivering the valve 100 to the desired location in the body (e.g., via the delivery/deployment system 180) can be similar to and/or the substantially the same as the delivery system(s) described in the '032 PCT, incorporated by reference above. Accordingly, portions and/or aspects of the devices and/or procedures used to deliver the valve 100 to, for example, the annulus of the native heart valve shown in FIGS. 5 and 6 are not described in further detail herein.

As shown in FIGS. 5 and 6, the delivery/deployment system 180 can be used to deliver the valve 100, for example, to an atrium of the human heart (the right atrium or the left atrium shown in FIG. 6 as (RA, LA)). In some implementations, for example, the valve 100 (e.g., the supra-annular member/region 120) can be removably coupled to a control device 170 included in the delivery/deployment system 180 that can be used to advance the valve 100 in the compressed state through a lumen of the delivery catheter 182, and into the atrium (RA, LA) of the heart, as described in detail with reference to the delivery/deployment systems in the '032 PCT. For example, a distal end portion of the control device 170 can include and/or can be coupled to a connection member 178 that is removably coupled to and in contact with a portion of the valve 100 (e.g., the supra-annular region 120), while a proximal end portion of the control device 170 is proximal to and outside of the delivery catheter 182. Such an arrangement can allow a distally directed force exerted on or at the proximal end portion of the control device 170 to advance the valve 100 along or over a guidewire and/or guidewire catheter (e.g., disposed within and/or extending through the guidewire coupler 133), through the delivery catheter 182, and into the annulus of a native heart valve.

Once in the atrium and released from the delivery catheter 182, the valve 100 can transition to the expanded configuration for deployment into an annulus of a native valve such as, for example, the pulmonary valve, the mitral valve, the aortic valve, and/or the tricuspid valve. In some embodiments, at least portion of the control device 170 or the like can extend through one or more lumens of the delivery catheter 182 to a position that is distal to the delivery catheter 182 and within the atrium, thereby allowing a user (e.g., a doctor, surgeon, technician, etc.) to manipulate a distal end of the control device 170 and thus one or more portions of the valve 100 for deployment into the annulus. For example, the connection member 178 can be included and/or disposed at a distal end of the control device 170 and can be advanced through the delivery catheter 182 and into the atrium of the heart (e.g., distal to the delivery catheter 182). Although not shown in FIGS. 1-6, the connection member 178 can be any suitable shape, size, and/or configuration. For example, the connection member 178 can be a yoke or the like that is removably coupled to the supra-annular region 120 of the valve frame 110, as described in detail in the '996 PCT and/or the '032 PCT. The arrangement of the connection member 178 can allow a user to at least partially control a position, orientation, angle, etc. of the valve 100 while the control device 170 is manipulated to deploy the valve 100 in the annulus.

As described above, in some instances, it may be desirable to include in the delivery/deployment system 180 one or more components, members, features, etc. that can at least temporarily couple to or otherwise engage (e.g., in conjunction with the connection member 178) one or more portions of the valve 100 to provide additional control and/or stability of the valve 100 during deployment. The support can extend through the delivery catheter 182 directly (e.g., through a lumen of the delivery catheter) or indirectly (e.g., via a lumen of a multi-lumen control catheter or a lumen of any other suitable catheter or sheath that extends through the delivery catheter 182). A distal end of the support can be removably coupleable to a portion of the valve 100 and/or valve frame 110, while a proximal end of the support can be maintained proximal to the delivery catheter 182, thereby allowing a user to manipulate the support to at least partially control, support, and/or stabilize one or more portions of the valve 100 during deployment.

FIG. 5 shows an example of such a support in the form of at least one supra-annular support 179. The supra-annular support 179 (also referred to herein as "support") can be any suitable feature, component, member, device, mechanism, and/or the like configured to support at least the supra-annular region 120 of the valve 100 and/or the valve frame 110 during deployment into the annulus. In some embodiments, the support 179 can be one or more tethers, sutures, tensile members, rods, cables, tubes, catheters, and/or the like that extend through the delivery catheter 182 directly or indirectly such that a proximal end portion of the support 179 (not shown) is maintained proximal to the delivery catheter 182 and a distal end portion of the support 179 is removably coupled to the supra-annular region 120 of the valve frame 110. In some implementations, the arrangement of the support 179 (e.g., one or more tethers, sutures, tensile members, rods, cables, tubes, catheters, and/or the like) is such that the support 179 can be placed under tension and/or otherwise allowed to be in a support configuration and/or state after the valve 100 is released from the delivery catheter 182 and allowed to expand to the expanded/deployment configuration, thereby providing additional control, support, and/or stabilization of the valve 100 during deployment. In some implementations, the arrangement of the support 179 is such that the support 179 can have a desired or predetermined stiffness, rigidity, durometer, etc. allowing the support 179 to transmit a distally-directed force onto the supra-annular region 120 of the valve frame 110 (e.g., enabling the support 179 to push the valve 100, for example, toward or into the annulus.

The delivery/deployment system 180 can include any number of supports 1779 configured to removably couple to any number of attachment points at any suitable location along the supra-annular region 120 of the valve frame 110. For example, in some implementations, the delivery/deployment system 180 can include a single support 179 that removably couples to an attachment point at or near a distal end of the supra-annular region 120 of the valve frame 110. In some implementations, the supra-annular region 120 of the valve frame 110 can include two or more attachment points at or near opposite lateral extents thereof with at least one support 179 coupling to each attachment point (e.g., at least two supports 179 extending from the distal end of the delivery catheter 182 in a Y-shape configuration). In such implementations, the attachment points can be distal to a contact point between the supra-annular region 120 of the valve frame 110 and the connection member 178. In some implementations, the delivery/deployment system 180 can include any number of supports 179 that can be coupled to attachment points at any suitable position(s) along the supra-annular region 120 of the valve frame 110 that provide a desired degree of control, support, and/or stability of the valve 100 during deployment, as described in further detail herein.

In some embodiments, the support 179 can be one or more reconfigurable members that can transition from a first state/configuration (e.g., during delivery through the delivery catheter 182) to a second state/configuration (e.g., during deployment into the annulus). For example, the support 179 can be relatively flexible when in the first state and can be relatively rigid or taught when in the second state, thereby forming a substantially rigid or fixed connection between the supra-annular region 120 of the valve frame 110 and a distal end portion of the delivery/deployment system 180 that can support, stabilize, and/or at least partially control the valve 100 during deployment. For example, the support 179 can be one or more tethers that are relatively flexible when in the first state during delivery and that can be placed under tension to transition to the second state in which the tethers form a relatively rigid, taught, and/or fixed connection between the supra-annular region 120 of the valve frame 110 and the distal end portion of the delivery/deployment system 180. In some embodiments, the substantially rigid, taught, and/or fixed connection between the supra-annular region 120 of the valve frame 110 and the distal end portion of the delivery/deployment system 180 can be based on a substantially fixed-length portion of the support 179 being disposed therebetween. In some embodiments, the support 179 can be configured to transition and/or actuate one or more parts of the supra-annular region 120 of the valve frame 110 to facilitate deployment, as described in further detail herein.

In some implementations, the support 179 can extend through the lumen of the delivery catheter 182 (or a lumen of a delivery sheath extending through the delivery catheter 182) while being outside of or otherwise not directly attached to the control device 170. In some implementations, such an arrangement can allow the support 179 to anchor and/or couple the supra-annular region 120 of the valve frame 110 to the delivery/deployment system 180 while allowing the control device 170 to move, transition, and/or otherwise reconfigure to control and deploy the valve 100 into the annulus. In some implementations, the support 179 in the second or support state/configuration can stabilize at least a portion of the valve 100, which in turn, can provide greater control of the valve 100 when moving and/or positioning the valve via the control device 170.

The supra-annular region 120 of the valve frame 110 can include and/or can form one or more attachment points or the like to which the distal end of the support 179 can removably couple. In some such embodiments, the attachment point can be a suture or the like around or through which the support 179 can be wrapped, looped, and/or otherwise removably attached. In some embodiments, the attachment point can be, for example, an opening or hole (e.g., in a drum of the supra-annular region 120 of the valve 100 and/or valve frame 110) through which a portion of the support 179 can extend (e.g., allowing the support 179 to engage a portion of the valve 100 other than the supra-annular region 120 of the valve frame 110). In some embodiments, the supra-annular region 120 of the valve frame 110 can include one or more attachment points such as one or more sutures and can provide and/or define an opening or hole, thereby allowing a first portion of the support 179 to engage or removably couple to the attachment point while a second portion of the support 179 extends through the opening or hole (e.g., allowing the support 179 to engage a portion of the valve 100 other than the supra-annular region 120 of the valve frame 110).

For example, the attachment point can be a suture attached to a distal end or portion of the supra-annular region 120 of the valve frame and the opening or hole can be formed at or along a distal region of the drum (e.g., proximal to the attachment point) allowing a distal portion of the support 179 to extend therethrough. In such embodiments, the distal end of the support 179 can include and/or can form a loop, hoop, ring, etc. that can be disposed over the guidewire catheter, guidewire, and/or subannular portion of the valve 100. In some implementations, such an arrangement can facilitate retrieval and/or retraction of the support 179 once the valve 100 is seated in the annulus. For example, disposing the loop or ring at the distal end of the support 179 around the guidewire catheter can be such that withdrawing the guidewire catheter after seating the valve 100 releases the distal end of the support 179, thereby allowing the support 179 to be withdrawn into the deployment system 180. In some implementations, a distal portion of the support 179 can be run outside the valve 100 along a distal wall of the transannular region 112 from the supra-annular region 120 (or member) to the subannular region 130 (or member), or to the guidewire or guidewire catheter extending therefrom, which can allow the distal portion of the support 179 to be sandwiched or trapped between the wall of the valve 100 and native tissue forming a portion of the annulus, which in turn, can secure or facilitate the securement of the support 179 to the distal portion of the valve 100.

As shown in FIGS. 5 and 6, deployment and/or seating of the valve 100 can include placing the distal anchoring element 132 of the subannular region 130 in a ventricle of the heart (the right ventricle or the left ventricle—(RV, LV) shown in FIG. 6) below the annulus while the remaining portions of the valve 100 are in the atrium (RA, LA). In some instances, the distal anchoring element 132 can be advanced over and/or along the guidewire or guidewire catheter (not shown) to a desired position within the ventricle such as, for example, an outflow tract of the ventricle. For example, in some implementations, the valve 100 can be delivered to the annulus of the native tricuspid valve and at least a portion of the distal anchoring element 132 can be positioned in the RVOT. In other implementations, the valve 100 can be delivered to the annulus of the native mitral valve and at least a portion of the distal anchoring element 132 can be positioned in a subannular position distal to the annulus and/or in any other suitable position in which the distal anchoring element 132 can engage native tissue, leaflets, chordae, etc. A distal portion or surface of the valve 100 can be placed in contact with and/or adjacent to a distal surface of the annular tissue when the distal anchoring element 132 is positioned in the ventricle (e.g., in the RVOT). With the distal portion of the valve 100 in a desired position within the annulus, the control device 170 can be manipulated to pivot the proximal portion of the valve 100 into the annulus, thereby seating the prosthetic valve 100. For example, the control device 170 can be and/or can include a steerable control catheter that can be manipulated (steered) to exert a force on a proximal portion of the valve 100 in a direction toward the annulus, thereby pivoting the valve 100 or at least the proximal portion of the valve 100 toward and/or into the annulus.

As described above, embodiments described herein can be configured to support, stabilize, and/or at least partially control the valve 100 while the valve 100 is being seated in the annulus. For example, FIG. 5 shows, one or more supports 179 can be coupled to the supra-annular region 120 of the valve frame 110 and can be placed in tension and/or otherwise allowed to be in a support configuration to at least partially support, stabilize, and/or control the valve 100 during deployment. For example, in some implementations, the connection member 178 can be configured to removably couple to a proximal portion of the supra-annular region 120 of the valve frame 110 and one or more support(s) 179 can be configured to removably couple to a distal portion of the supra-annular region 120 of the valve frame 110. In some such implementations, the distal portion of the supra-annular region 120 of the valve frame 110 can include one or more attachment points to which the one or more supports 179 can removably couple. In some implementations, a distal portion of the drum or other surface of the valve 100 can form and/or define an opening or hole through which a distal portion of the support 179 can extend. The distal end of the support 179 can include and/or can form a loop, hoop, ring, etc. that can be disposed over, around, or about the guidewire catheter (or guidewire) and/or a subannular portion of the valve 100 to releasably secure and/or anchor the distal portion of the support 179. In some implementations, a distal portion of the support 179 can run along a distal wall of the valve frame 110 from the supra-annular region 120 to the subannular region 130 (or guidewire or guidewire catheter) and can the contact between the surface of the valve 100 and the surface of the annular tissue can sandwich, pinch, retain, constrain, and/or otherwise substantially secure the distal portion of the support 179 to the distal portion of the valve 100.

With the distal portion of the support 179 secured relative to the distal portion of the valve 100 (in any suitable manner such as those described above) the support 179 can be transitioned to the second or support state/configuration. The support 179, in turn, can provide support to at least the distal portion of the valve 100 that can, for example, resist, limit, and/or otherwise prevent a distal supra-annular portion of the valve 100 and/or valve frame 110 from dropping into the annulus. In some implementations, removably coupling the support 179 to the attachment point at or along the distal portion of the supra-annular region 120 of the valve frame 110 (e.g., a distal portion of an outer loop of the supra-annular region 120, also referred to herein as a "atrial distal cuff or portion" of the valve 100) can allow the support 179 to actuate, manipulate, reconfigure, and/or otherwise transition at least the atrial distal portion of the valve 100. For example, as shown in FIG. 5, in the initial stages of deployment, the distal subannular anchoring element 132 can be disposed in the ventricle and a distal wall of the valve 100 (or at least a portion thereof) can be in contact with a distal surface of the annulus, while the proximal subannular anchoring element 134 is in the atrium. As such, the valve 100 is disposed at an angle relative to an annular plane of the annulus. In some embodiments, the size and/or shape of the atrial distal cuff or portion can be in contact with the atrial floor and the angle of the valve 100 may be such that the atrial distal cuff pushes the distal portion of the valve 100 away from the annulus, thereby resisting the process of pivoting and/or seating the valve 100. In some such embodiments, the support 179 removably coupled to the attachment point at or along the atrial distal cuff can allow the support 179 to actuate at least a part of the atrial distal cuff to facilitate the process of seating the valve 100. For example, as indicated by the arrows in FIG. 5, a proximally-directed force can be exerted on or along the support 179, which in turn, can pull, actuate, or otherwise act on the atrial distal cuff to move, bend, flex, and/or transition the atrial distal cuff in a proximal direction away from the atrial floor or atrial tissue defining or surrounding the annulus. Accordingly, transitioning or actuating the atrial distal cuff in such a manner can reduce the contact between the atrial distal cuff and the atrial tissue that may otherwise resist the pivoting motion associated with seating the valve 100 in the annulus.

Although not shown in FIG. 5, in some implementations, the support(s) can include at least two supports 179, each of which is coupled to an attachment point at or near a lateral extent of the supra-annular region 120 and distal to the connection member 178. In such implementations, the supports 179 can stabilize the valve 100, for example, against undesired rotation or spinning about the guidewire or guidewire catheter (or an axis thereof) and relative to an annular plane. In some implementations, the supra-annular region 120 can be coupled to any suitable number of support(s) 179 in any suitable position(s) (or combination of positions) that enable the supports 179 to support, stabilize, actuate, and/or control the valve 100 as the valve 100 is seated in the annulus.

In some implementations, the prosthetic valve 100 can be temporarily maintained in a partially deployed state. For example, the valve 100 can be partially inserted into the annulus and held at an angle relative to the annulus to allow blood to flow from the atrium to the ventricle partially through the native valve annulus around the valve 100, and partially through the valve 100, which can allow for assessment of the valve function. In some instances, the support 179 can support the valve 100 while the valve 100 is in the partially deployed state.

In some implementations, the support 179, and/or the substantially rigid or fixed-length connection between the distal supra-annular portion of the valve 100 and the portion of the delivery/deployment system 180 (e.g., outside of or substantially independent of the control device 170) provided by the support 179, can result in a reaction/opposing force in response to the force exerted by the control device 170 to pivot or seat at least the proximal portion of the valve 100 in the annulus. In some instances, such an arrangement can reduce relative movement of at least a portion of the control device 170 that does not contribute to the deployment of the valve 100, thereby facilitating the deployment process.

As described above, in some implementations, the proximal subannular anchoring element 134 can be maintained in its first configuration during this stage of deployment, which in turn, allows the proximal portion of the valve 100 to "drop" into the annulus. For example, the proximal anchoring element 134 can be in a compressed, contracted, and/or retracted configuration in which the proximal anchoring element 134 is in contact with, adjacent to, and/or near the transannular region 112 and/or the supra-annular region 120 of the frame 110. In turn, this configuration can limit an overall circumference of the subannular region 130 of the frame 110, thereby allowing the subannular region 130 and the transannular region 112 of the frame 110 to be inserted into and/or through the annulus.

FIG. 6 shows the valve 100 (PV, MV, AV, TV) placed and/or seated in an annulus (PVA, MVA, AVA, TVA) of the native valve such that the subannular region 130 (e.g., a ventricular collar) is disposed in a subannular position, the transannular region 112 of the valve frame 110 extends through the annulus, and the supra-annular region 120 (e.g., an atrial collar) remains in a supra-annular position. In some embodiments, the control device 170 of the delivery/deployment system 180 can be configured to actuate one or more portions of the valve 100 such as, for example, the proximal anchoring element 134 between its first and second configurations. For example, the control device 170 can include one or more cables, tethers, linkages, joints, connections, tensile members, etc., that can exert a force (or can remove an exerted force) on a portion of the proximal anchoring element 134 operable to transition the proximal anchoring element 134 between the first and second configuration. In some embodiments, the subannular region 130 of the support frame 110 can be formed with the proximal anchoring element 134 biased in the uncompressed and/or expanded configuration.

Accordingly, the control device 170 can be actuated to exert a force, via the one or more cables, tethers, etc., to transition the proximal anchoring element 134 to the compressed and/or retracted configuration and can be actuated and/or otherwise manipulated to release or reduce the force to transition—or to allow the transitioning of—the proximal anchoring element 134 from the compressed and/or retracted configuration to the expanded or uncompressed configuration. For example, once the valve 100 is seated in the native annulus (PVA, MVA, AVA, TVA), a user can manipulate a portion of the delivery/deployment system 180 to actuate the control device 170, thereby causing the control device 170 to release and/or remove the force exerted on the proximal anchoring element 134 (e.g., via the cable(s), tether(s), etc.). In turn, the proximal anchoring element 134 can return to its original or biased configuration (e.g., a second configuration).

As described above, supra-annular region 120 of the valve frame 110 (e.g., the atrial cuff) can be configured to engage native atrial tissue, the distal anchoring element 132 can be configured to engage native ventricular tissue on a distal side of the annulus, and the proximal anchoring element 134 can be configured to engage native ventricular tissue on a proximal side of the annulus (e.g., when in the second or expanded configuration), thereby securely seating the valve 100 in the native annulus, as shown in FIG. 6. In some implementations, any other or additional portions of the valve 100 can similarly engage native tissue to securely seat the valve 100 in the native annulus and/or to form a seal between the support frame 110 and the tissue forming the native annulus (e.g., an anterior anchoring element can engage subannular tissue on an anterior side of the annulus, or the supra-annular region 120 can include any number of supra-annular anchoring elements for engaging supra-annular tissue (not shown in FIGS. 1-6)). With the valve 100 secured in the annulus, the delivery/deployment system 180 (including the control device 170, the support 179, the guidewire and/or guidewire catheter, and/or any other portion or component of the delivery/deployment system 180) can be decoupled from the valve 100 and retracted/removed from the patient, leaving the prosthetic valve 100 in place. As described above, in some implementations, the arrangement of the support 179 can be such that the distal end is wrapped or looped around the guidewire and/or guidewire catheter. In such implementations, withdrawing the guidewire and guidewire catheter into the delivery/deployment system 180 (e.g., proximal to the valve 100) can release the distal end of the support 179, thereby allowing the support 179 to be retracted and/or withdrawn from the valve 100 and into or through the delivery/deployment system 180. In other implementations, the distal end of the supports 179 can be decoupled from the attachment points in any suitable manner.

Provided below is a discussion of certain aspects or embodiments of side deliverable transcatheter prosthetic valves (e.g., prosthetic valves) and/or delivery systems and methods for delivering such prosthetic valves. The prosthetic valves (or aspects or portions thereof) described below with respect to specific embodiments can be substantially similar in at least form and/or function to the valve 100 (or corresponding aspects or portions thereof). Likewise, the delivery/deployment systems and/or methods (or aspects or portions thereof) described below with respect to specific embodiments can be substantially similar in at least form, function, and/or process as the deployment system 180 or process of using the deployment system 180 (or aspects, portions, and/or processes thereof). Thus, certain aspects and/or portions of the specific embodiments may not be described in further detail herein.

Figures 7, 8:
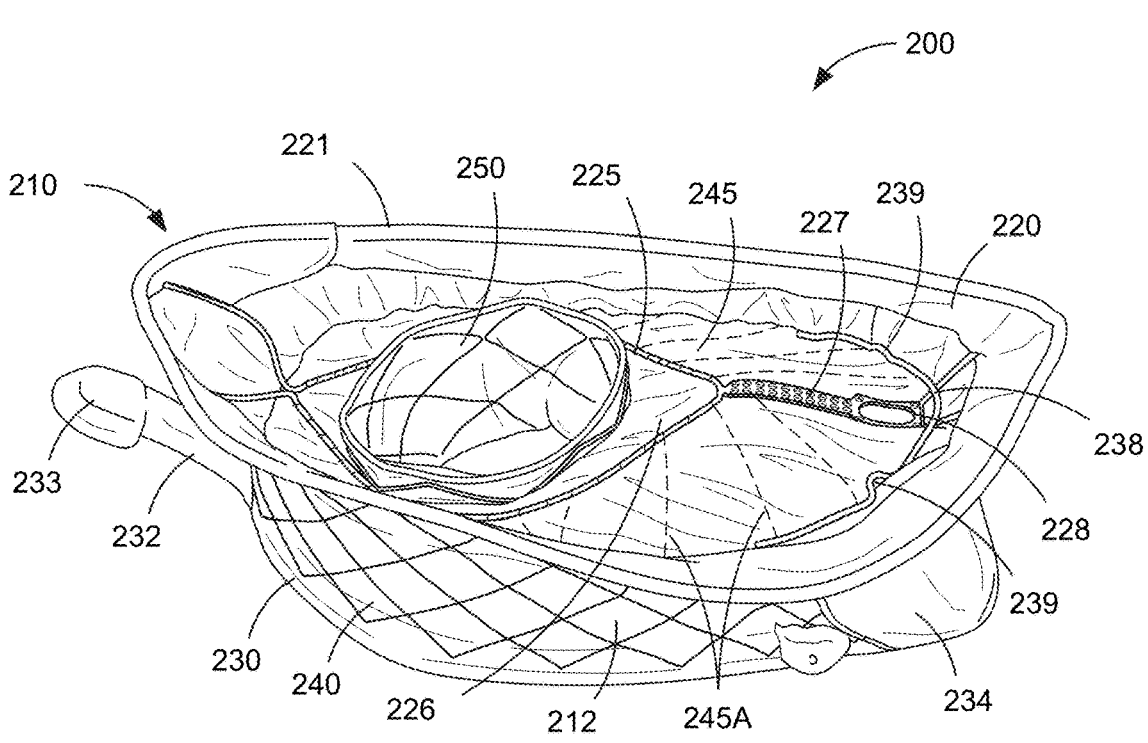
FIGS. 7 and 8 are an elevated side perspective view and
a bottom perspective view, respectively, of a prosthetic valve
according to an embodiment.

FIGS. 7-16 illustrate a side-deliverable (orthogonally deliverable) transcatheter prosthetic heart valve 200 (also referred to herein as "prosthetic valve" or "valve"), according to an embodiment. FIG. 7 is an illustration of a top perspective view of the valve 200. In some implementations, the valve 200 can be deployed in, for example, an annulus of a native tricuspid and/or mitral valve. The valve 200 is configured to permit blood flow in a first direction through an inflow end of the valve 200 and to block blood flow in a second direction, opposite the first direction, through an outflow end of the valve 200. For example, the prosthetic valve 200 can be a side deliverable transcatheter prosthetic heart valve configured to be deployed within the annulus of a native tricuspid valve or native mitral valve of a human heart to supplement and/or replace the functioning of the native valve.

The valve 200 is compressible and expandable in at least one direction relative to an x-axis of the valve 200 (also referred to herein as "horizontal axis," "longitudinal axis," "long axis," and/or "lengthwise axis"). The valve 200 is compressible and expandable between an expanded configuration for implanting at a desired location in a body (e.g., a human heart) and a compressed configuration for introduction into the body using a delivery catheter (not shown in FIG. 7). In some embodiments, the horizontal x-axis of the valve 200 is orthogonal to (90 degrees), or substantially orthogonal to (75-105 degrees), or substantially oblique to (45-135 degrees) to a central (vertical) y-axis when in the expanded and/or compressed configuration. Moreover, the horizontal x-axis of the valve 200 in the compressed configuration is substantially parallel to a lengthwise cylindrical axis of the delivery catheter in which the valve 200 is disposed.

In some embodiments, the valve 200 has an expanded or deployed height of about 5-60 mm, about 5-30 mm, about 5-20 mm, about 8-12 mm, or about 8-10 mm, and an expanded or deployed diameter (e.g., length and/or width) of about 25-80 mm, or about 40-80 mm. In some embodiments, the valve 200 has a compressed height (y-axis) and width (z-axis) of about 6-15 mm, about 8-12 mm, or about 9-10 mm. It some implementations, a length of the valve 200 (e.g., along the x-axis) is not compressed or otherwise reduced since it can extend along the length of the central cylindrical axis of the delivery catheter (e.g., the longitudinal or lengthwise axis).

In certain embodiments, the valve 200 can be centric or eccentric (e.g., radially symmetric or radially asymmetric, respectively, along or relative to the y-axis). In some eccentric embodiments, the frame 210 may have a D-shape in cross-section, with a flat portion or surface configured to substantially match an annulus of a native mitral valve at or near the anterior leaflet. In the example shown in FIGS. 7-16, the valve 200 is eccentric with one or more components being offset or asymmetrical region to the y-axis.

FIGS. 7 and 8 show the valve 200 including an annular outer support frame 210 and a collapsible flow control component 250 mounted within the annular outer support frame 210. The annular outer support frame 210 (also referred to herein as "outer frame") is made from a shape-memory material such as Nickel-Titanium alloy (Nitinol) and is therefore a self-expanding structure from a compressed configuration to an expanded configuration. The outer frame 210 has a transannular member 212 and/or body that circumscribes, forms, and/or defines a central (interior) channel about and/or along the vertical or central axis (y-axis). The outer frame 210 has a supra-annular member 220 attached circumferentially at a top edge of the transannular member 212 and a subannular member 230 attached circumferentially at a bottom edge of the transannular member 212. As shown in FIGS. 7 and 8, at least the outer support frame 210 of the valve 200 is covered, wrapped, and/or surrounded by a biocompatible cover 240. The biocompatible cover 240 can be a mesh material, a pericardial tissue, a woven synthetic polyester material, and/or any other suitable biocompatible material such as those described above.

The biocompatible cover 240 disposed on or along the supra-annular member 220 can form a drum 245 that extends between and/or is coupled to an outer loop and an inner loop of the supra-annular member 220. As such, the drum 245 can cover a space not otherwise occupied by the flow control component 250. The drum 245 can have and/or can form a set of spokes 245A that can be used to increase a stiffness of the drum 245. The drum 245 is further shown having an attachment member 238 that can extend along or across a portion of the drum 245 (or supra-annular member 220). As described in further detail here, the attachment member 238 can facilitate a temporary and/or removable attachment to a portion of a delivery/deployment system such as, for example, a control device, actuator, etc.

The supra-annular member 220 is shaped to conform to the native deployment location. In a tricuspid replacement, for example, the supra-annular member 220 or atrial collar can have a tall back wall portion to conform to the septal area of the native valve and can have a distal and proximal portion. The distal portion can be larger than the proximal portion to account for the larger flat space above (atrial) the ventricular outflow tract (VOT) subannular area. In a mitral replacement, for example, the supra-annular member 220 of the outer frame 210 may be D-shaped or shaped like a hyperbolic paraboloid to mimic the native structure. In some embodiments, the supra-annular member 220 of the outer frame 210 can be substantially similar in at least form and/or function to the supra-annular region 120 (or member) described above. Thus, portions and/or aspects of the supra-annular member 220 may not be described in further detail herein.

Figures 9, 10, 11:
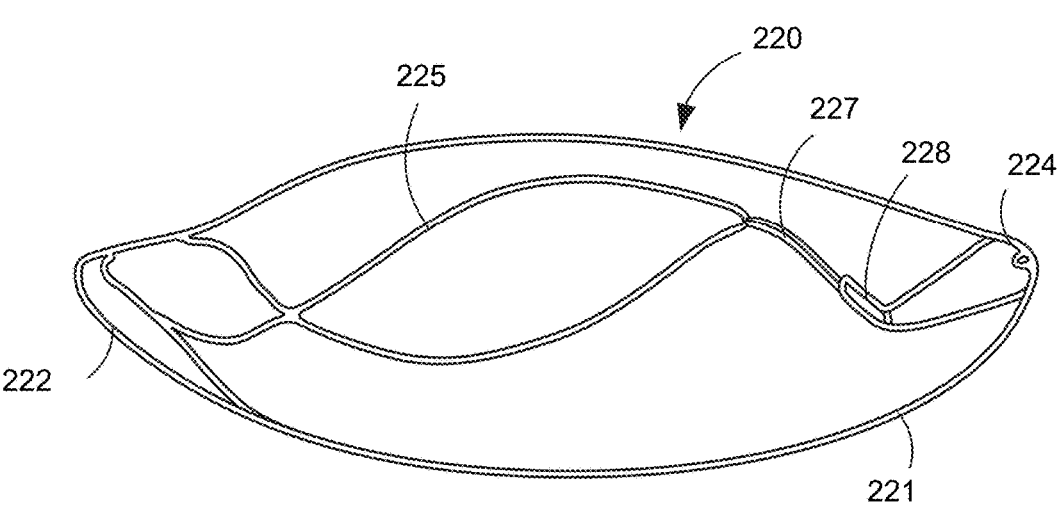
FIG. 9 is an elevated side perspective view of a supra-
annular region of an outer support frame of the prosthetic
valve shown in FIG. 7.
FIG. 10 is a distal perspective view of a transannular
region of the outer support frame of the prosthetic valve
shown in FIG. 7.
FIG. 11 is a distal perspective view of a subannular region
of the outer support frame of the prosthetic valve shown in
FIG. 7.

FIG. 9 shows a laser-cut wire frame portion of the supra-annular member 220 (uncovered). As shown, the supra-annular member 220 includes a distal portion 222, a proximal portion 224, an outer loop 221, an inner loop 225, and at least one spline 227. In some embodiments, the outer loop 221 can be shaped and/or sized to engage native tissue. For example, the distal portion 222 of the supra-annular member 220 (formed at least in part by the outer loop 221) is configured to engage distal supra-annular tissue and the proximal portion 224 (formed at least in part by the outer loop 221) is configured to engage proximal supra-annular tissue. The distal and proximal portions 222 and 224 can have a rounded and/or curved shape, wherein a radius of curvature of the proximal portion 224 is larger than a radius of curvature of the distal portion 222. The distal portion 222 can form, for example, a distal anchoring loop 223 that can engage distal supra-annular tissue to at least partially stabilize and/or secure the frame 210 in the native annulus. Although not shown in FIG. 9, the proximal portion 224 similarly can form a proximal upper anchoring element that can engage proximal supra-annular tissue to at least partially stabilize and/or secure the frame 210 in the native annulus.

The inner loop 225 of the supra-annular member 220 can be substantially circular, oblong, teardrop-shaped, and/or any other suitable shape. The inner loop 225 can be coupled to and/or suspended from the outer loop by the one or more splines 227. As shown in FIG. 7, the inner loop 225 can be coupled to biocompatible material 226, which can be used to couple the inner frame 251 of the flow control component 250 to the inner loop 225 of the outer support frame 210. In some implementations, suspending the inner loop 225 from the outer loop 221 can, for example, at least partially isolate the inner loop 225 (and the flow control component 250 coupled to the inner loop 225) from at least a portion of the force associated with transitioning the frame 210 between the expanded configuration and the compressed configuration, as described above with reference to the frame 210.

The one or more splines 227 of the supra-annular member 220 can be any suitable shape, size, and/or configuration. For example, in some embodiments, the supra-annular member 220 can include a proximal spline 227 and one or more distal splines. The distal splines can couple a distal portion of the inner loop 225 to a distal portion of the outer loop 221. Similarly, the proximal spline 227 can couple a proximal portion of the inner loop 225 to a proximal portion of the outer loop 221. In some embodiments, the proximal spline 227 can be configured to receive, couple to, and/or otherwise engage an actuator, a control device, and/or a portion of a delivery system. For example, the proximal spline 227 includes, forms, and/or can be coupled to a waypoint 228 that can be used to couple and/or to receive one or more portions of the control device and/or delivery system, as described above with reference to the frame 110.

As shown in FIGS. 7-9, in this embodiment, the supra-annular member 220 has a bowed configuration in which the spline 227 protrudes away from other portions of the supra-annular member 220. For example, the laser cut frame of the supra-annular member 220 can be formed with the spline 227 having the bowed configuration (FIG. 9). In some implementations, bowed spline 227 can exert a force on the drum 245 that bows the drum 245 and increases a tension across the area of the drum 245. The increase in tension, alone or in conjunction with the spokes 245A, increases a relative stiffness of the drum 245, which can reduce and/or limit an amount of drum deformation during, for example, diastole or systole, thereby enhancing performance of the valve 200 and/or reduce fatigue in or along the drum 245. Said another way, the pressure produced on the atrial side of the drum 245 during contraction of the atrium (diastole) is not sufficient to invert the bowed configuration of the drum 245 (e.g., will not produce an oil-can like deflection) due to the bowed spline 227. The bowed configuration of the drum 245 can also withstand the greater pressure produced on the ventricle side of the drum 245 during contraction of the ventricle (systole) without substantial deflection. Moreover, the bow in the spline 227 can be such that the waypoint 228 is positioned at a desired angle and/or orientation to facilitate the insertion or retrieval of one or more portions of the delivery system through the waypoint 228.

FIG. 10 is a distal perspective view illustrating the transannular member 212 of the outer frame 210 of the valve 200. In some embodiments, the transannular member 212 of the outer frame 210 can be substantially similar in at least form and/or function to the transannular region 112 (or member) described above. Thus, portions and/or aspects of the transannular member 212 may not be described in further detail herein.

The transannular member 212 can be shaped and/or formed into a ring, a cylindrical tube, a conical tube, and/or any other suitable annular shape. In some embodiments, the transannular member 212 may have a side profile of a concave cylinder (walls bent in); an angular hourglass; a curved, graduated hourglass; a ring or cylinder having a flared top, flared bottom, or both; and/or the like. Moreover, the transannular member 212 can form and/or define an aperture or central channel 214 that extends along the central axis 204 (e.g., the y-axis). The central channel 214 (e.g., a central axial lumen or channel) can be sized and configured to receive the flow control component 250 across a portion of a diameter of the central channel 214. In some embodiments, the transannular member 212 can have a shape and/or size that is at least partially based on a size, shape, and/or configuration of the supra-annular member 220 and/or subannular member 230 of the outer support frame 210, and/or the native annulus in which it is configured to be deployed, as described above.

The transannular member 212 can be and/or can include a wire frame that is laser cut out of Nitinol or the like and, for example, heat-set into a desired shape and/or configuration. The transannular member 212 can be formed to include a set of compressible wire cells 213 having an orientation and/or cell geometry substantially orthogonal to the central axis extending through the central channel 214 to minimize wire cell strain when the transannular member 212 is in a vertical compressed configuration, a rolled and compressed configuration, or a folded and compressed configuration. As shown in FIG. 10, the transannular member 212 includes an anterior side 215 (e.g., first laser-cut half) and a posterior side 216 (e.g., a second laser-cut half) that can be formed into a desired shape and coupled together to form the transannular member 212. The anterior side 215 and the posterior side 216 can be coupled at one or more hinge points 217 along a distal portion and a proximal portion of the transannular member 212. More specifically, the anterior side 215 and the posterior side 216 can be coupled along the distal side of the transannular member 212 via two sutures forming two hinge or coupling points 217 and can be coupled along the proximal side of the transannular member 212 via one suture forming a single hinge or coupling point 217.

In some embodiments, forming the transannular member 212 in such a manner can allow the transannular member 212 to bend, flex, fold, deform, and/or otherwise reconfigure (substantially without plastic deformation and/or undue fatigue) in response to lateral folding along or in a direction of a lateral or z-axis and/or vertical compression along or in a direction of the central or y-axis. Moreover, coupling at the hinge points 217 using sutures can allow for a desired amount of slippage between the sutures and the anterior/posterior sides 215/216, which in turn, can limit and/or substantially prevent binding, sticking, and/or failure in response to folding along the lateral or z-axis.

As shown in FIG. 10, the proximal portion of the transannular member 212 includes a single hinge or coupling point 217. In some embodiments, the transannular member 212 can define a gap or space 218 below the proximal hinge or coupling point 217 that can provide space to allow a proximal anchoring element of the subannular member 230 to transition between a first configuration and a second configuration, as described in further detail herein.

FIG. 11 is a distal perspective view illustrating the subannular member 230 of the outer frame 210 of the valve 200. In some embodiments, the subannular member 230 of the frame 210 can be similar in at least form and/or function to the subannular region 130 (or member) described above.

Thus, portions and/or aspects of the subannular member 230 may not be described in further detail herein.

As shown, the subannular member 230 of the frame 210 includes and/or forms a distal portion having a distal anchoring element 232 and a proximal portion having a proximal anchoring element 234. The anchoring elements 232 and 234 are integrally and/or monolithically formed with the subannular member 230. The distal anchoring element 232 and the proximal anchoring element 234 of the subannular member 230 can be any suitable shape, size, and/or configuration. The distal anchoring element 232 is shown as including an atraumatic end that forms a guidewire coupler 233 configured to selectively engage and/or receive a portion of a guidewire catheter 284 (having a guidewire 285 disposed therein) through an opening, hole, aperture, port, etc., defined by the guidewire coupler 233 (see e.g., FIGS. 15 and 16). With the guidewire catheter 284 extending through the guidewire coupler 233, the valve 200 is allowed to be advanced over or along the placed guidewire 285 disposed in the guidewire catheter 284. In some implementations, the guidewire catheter 284 can extend below the valve 200 and beyond the distal anchoring element 232, and can provide a desired stiffness during delivery and/or deployment.

The anchoring elements 232 and/or 234 are configured to engage a desired portion of the native tissue to mount the frame 210 to the annulus of the native valve in which it is deployed. For example, the distal anchoring element 232 can extend (e.g., about 10-40 mm) from the subannular member 230 and into a RVOT or other ventricular position. The distal anchoring element 232 can be shaped and/or biased such that the distal anchoring element 232 exerts a force on the subannular tissue operable to at least partially secure the distal end portion of the frame 210 in the native annulus.

The proximal anchoring element 234 can be configured to engage subannular tissue on a proximal side of the native annulus to aid in the securement of the frame 210 in the annulus. As described above, the subannular member 230 of the frame 210 can be and/or can include, for example, a laser cut wire frame formed of a shape-memory material such as Nitinol, which is heat-set into a desired shape and wrapped in a biocompatible material (e.g., a fabric and/or the like). The proximal anchoring element 234 is configured to transition, move, and/or otherwise reconfigure between a first configuration in which the proximal anchoring element 234 extends from the subannular member 230 a first amount or distance and a second configuration in which the proximal anchoring element 234 extends from the subannular member 230 a second amount or distance. Said another way, the proximal anchoring element 234 can be, for example, a movable anchoring element configured to be moved and/or otherwise transitioned (e.g., by an actuator) between a first configuration and a second configuration to reduce a perimeter of the subannular member 230 during delivery and/or deployment.

As described above, the proximal anchoring element 234 can be in a compressed, contracted, retracted, undeployed, folded, and/or restrained state (e.g., a position that is near, adjacent to, and/or in contact with the transannular member 212 and/or the supra-annular member 220 of the outer support frame 210) when in the first configuration, and can be in an expanded, extended, deployed, unfolded, and/or unrestrained state (e.g., extending away from the transannular member 212) when in the second state. In some embodiments, the proximal anchoring element 234 can be biased and/or heat-set in the second configuration. Moreover, in some implementations, the space 218 defined by the transannular member 212 of the outer frame 210 is configured to provide sufficient room to allow the proximal anchoring element 234 to transition between the first and second configurations.

The proximal anchoring element 234 can be configured to move in any suitable direction from the first, extended configuration to the second, compressed configuration based at least in part on how the proximal anchoring element 234 is coupled to an actuator and/or the like. For example, the proximal anchoring element 234 can be moved inward toward the inner flow control component 250, moved upward toward the supra-annular member 220 and/or portion thereof, and/or moved toward an anterior side or a posterior side of the valve 200. Moreover, with the transannular member 212 of the frame 210 coupled to the subannular member 230, actuation of an actuator, control device, etc., can, in some instances, move one or more portions of the transannular member 212, as described in further detail herein.

The collapsible (inner) flow control component 250 is mounted within the outer frame 210. The flow control component 250 has a foldable and compressible inner wire frame 35 (also referred to as "inner leaflet frame" or "inner frame") with two (or more) fold areas, hinge areas, coupling areas, elastically deformable regions, etc. A set of 2-4 flexible leaflet components 256 are mounted in or on the inner frame 251 (not shown in FIG. 7). In some embodiments, the flow control component 250 has three leaflet components 256 (e.g., cusps, pockets, or simply leaflets) mounted within the inner frame 251, as described in further detail herein.

The inner flow control component 250, like the outer frame 210, is foldable and compressible. For example, the inner frame 251 is foldable along or in the direction of a z-axis (e.g., foldable at the fold areas or the like) from a cylindrical configuration to a flattened cylinder configuration (or a two-layer band), where the fold areas are located on a distal side and on a proximal side of the inner frame 251. The flow control component 250, like the outer frame 210, is also vertically (y-axis) compressible to a shortened or compressed configuration. By folding (compressing) in the direction of the z-axis and vertically compressing in the y-axis, the valve 200 is permitted to maintain a relatively large dimension along the horizontal (x-axis). In some implementations, the outer frame 210 and the flow control component 250 are reduced along z-axis until the side walls are in contact or nearly so. This also allows the outer frame 210 and the flow control component 250 to maintain the radius along the horizontal axis (x-axis), to limit or substantially minimize the number of wire cells that can be damaged by forces applied during folding and/or compression when loading the valve 200 into the delivery catheter.

The flow control component 250 has a diameter and/or perimeter that is smaller than a diameter and/or perimeter of the central channel of the outer frame 210. The flow control component 250 is mounted to or within the outer frame 210 such that a central or vertical axis (y-axis) of the inner frame 251 is parallel to the central or vertical axis (y-axis) of the outer frame 210. In some embodiments, the y-axis defined by the inner frame 251 is parallel to but offset from the y-axis defined by the outer frame 210 (FIG. 7). In some implementations, a drum 245 (or other spacer element) is disposed within and/or across the central channel and can facilitate the mounting of a portion of the flow control component 250 (e.g., an otherwise unsupported portion) to the outer support frame 210 and/or an ingrowth of native tissue over at least a portion of the supra-annular member 220 of the valve 200.

In certain embodiments, the inner frame 251 can have a diameter of about 25-30 mm, the outer frame 210 (or the transannular member 212 thereof) can have a diameter of about 50-80 mm, and the supra-annular member 220 (or atrial collar) extend beyond the top edge of the transannular member 212 by about 20-30 mm to provide a seal on the atrial floor against perivalvular leaks (PVLs). The flow control component 250 and the outer frame 210 can be foldable (e.g., in the direction of the z-axis) and/or compressible (e.g., in the direction of the y-axis) to reduce a size of the valve 200 to fit within the inner diameter of a 24-36 Fr (8-12 mm inner diameter) delivery catheter (not shown in this FIG. 7).

Figure 12:
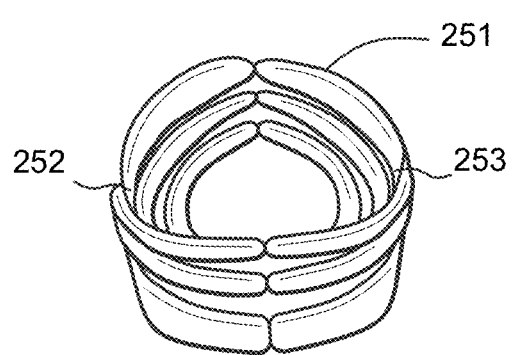
FIG. 12 is a top perspective view of an inner frame of a
flow control component included in the prosthetic valve
shown in FIG. 7.
Figure 13:
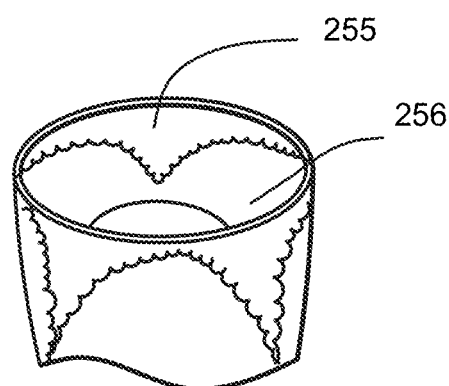
FIG. 13 is a side perspective view of a leaflet band of the
inner flow control component having leaflet pockets sewn
into a structural band and shown in a cylindrical configu-
ration suitable for coupling to the inner frame of FIG. 12.
Figure 14:
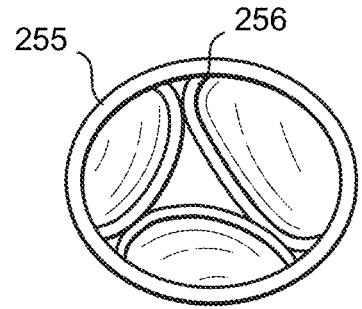
FIG. 14 is a bottom view of the leaflet band of FIG. 13 in
the cylindrical configuration and showing partial coaptation
of the leaflets to form a partially closed fluid-seal.

FIGS. 12-14 illustrate at least a portion of the flow control component 250 included in the valve 200. For example, FIG. 12 is an illustration of a top perspective view of the inner leaflet frame 251. In some embodiments, the inner leaflet frame 251 is formed of two separate wireframe sheets or members that are coupled at lateral connection points 252 and 253 (e.g., fold areas, elastically deformable regions, coupled edged portions, etc.). The inner leaflet frame 251 is shown in an expanded or cylindrical configuration (e.g., prior to being folded and/or compressed).

Although not shown, the inner leaflet frame 251 can be transitioned from the expanded or cylindrical configuration to an at least partially folded configuration. The inner leaflet frame 251 can have wireframe sidewalls that allow for rotating or hinging at least at the lateral connection points 252 and 253. The inner leaflet frame 251 can be configured to fold in response to the valve 200 being folded and/or compressed for delivery. When transitioned, for example, to a completely folded configuration, the wireframe sidewalls can be rotated, hinged, and/or folded at their lateral connection points 252 and 253. In addition, the inner leaflet frame 251 can be vertically compressed into a compressed configuration. The wireframe sidewalls can form cells (e.g., diamond-shaped cells or the like) that can be oriented in a direction of compression to allow for elastic compression of the inner frame 251. In some embodiments, the inner frame 251 can be vertically compressed into a pleated or accordion (compressed) configuration.

In some embodiments, the inner leaflet frame 251 of the flow control component 250 can be formed from a linear wireframe or laser cut sheet prior to being further assembled into a cylinder structure (e.g., as shown in FIG. 12). The inner leaflet frame 251 can be formed into the cylinder structure or configuration (or a conical structure or configuration) with edge portions of the linear wireframe sheet being connected or coupled at the lateral connection points 252 and 253 (e.g., hinge areas, fold areas, etc.). Moreover, the inner leaflet frame 251 can be expanded (e.g., driven, formed, bent, etc.) from the linear sheet configuration into the cylinder structure or configuration.

FIGS. 13 and 14 illustrate a structural band 255 of pericardial tissue with leaflet components 256 sewn into the structural band 255. FIGS. 13 and 14 are a side perspective view and a bottom view, respectively, illustrating the structural band 255 and leaflet components 256 (e.g., pockets) before assembly and/or mounting on and/or into the inner frame 251 to form the collapsible (foldable, compressible) flow control component 250. FIG. 13 shows the structural band 255 formed of pericardial tissue with the leaflet components 256 sewn into the structural band 255. After assembly into the cylindrical leaflet configuration shown, the leaflet components 256 are disposed on an inner surface of the structural band 255. The leaflet components 256 can be sewn into the structural band 255 such that an open edge extends outward, and a sewn edge forms a closed top parabolic edge providing attachment. FIG. 14 is an illustration of a bottom view of the flow control component 250. The cylindrical structural band 255 and leaflet components 256 are shown with partial coaptation towards forming a closed fluid-seal. Although not show, the cylindrical structural band 255 can be mounted to or in the inner leaflet frame 251 (FIG. 12) to collectively form the flow control component 250, which in turn, is mounted to the inner loop 225 of the supra-annular member 220 of the outer support frame 210, as described in detail above with reference to FIGS. 7 and 8.

Figure 15:
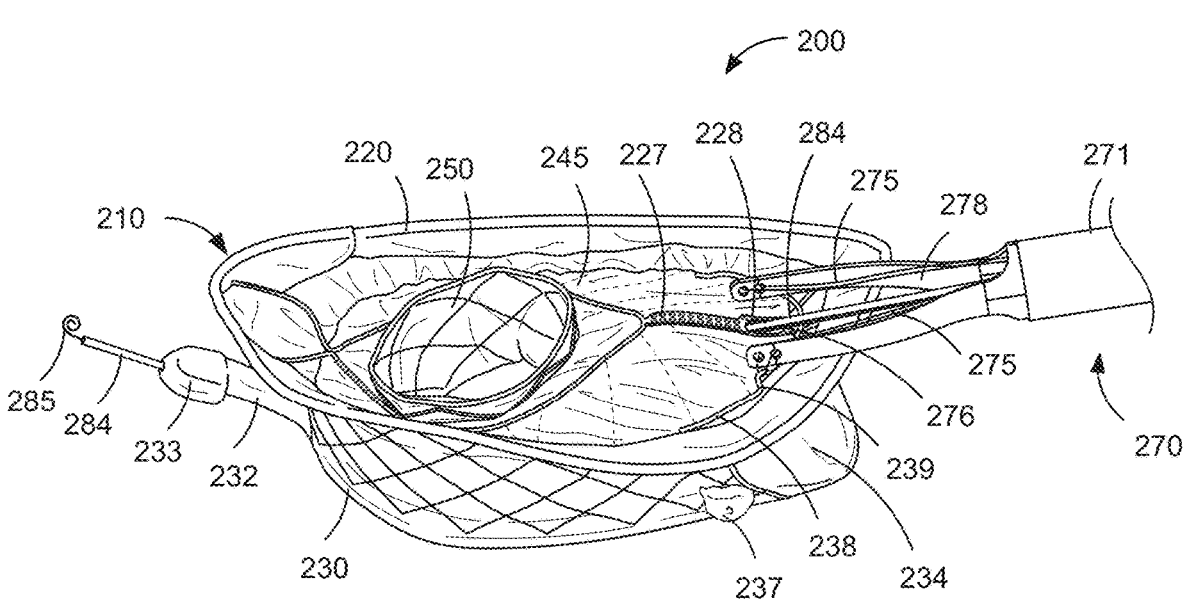
FIGS. 15 and 16 are elevated side perspective views of the
prosthetic valve of FIG. 7 removably coupled to a distal end
portion of a control device included in a delivery system.
Figure 16:
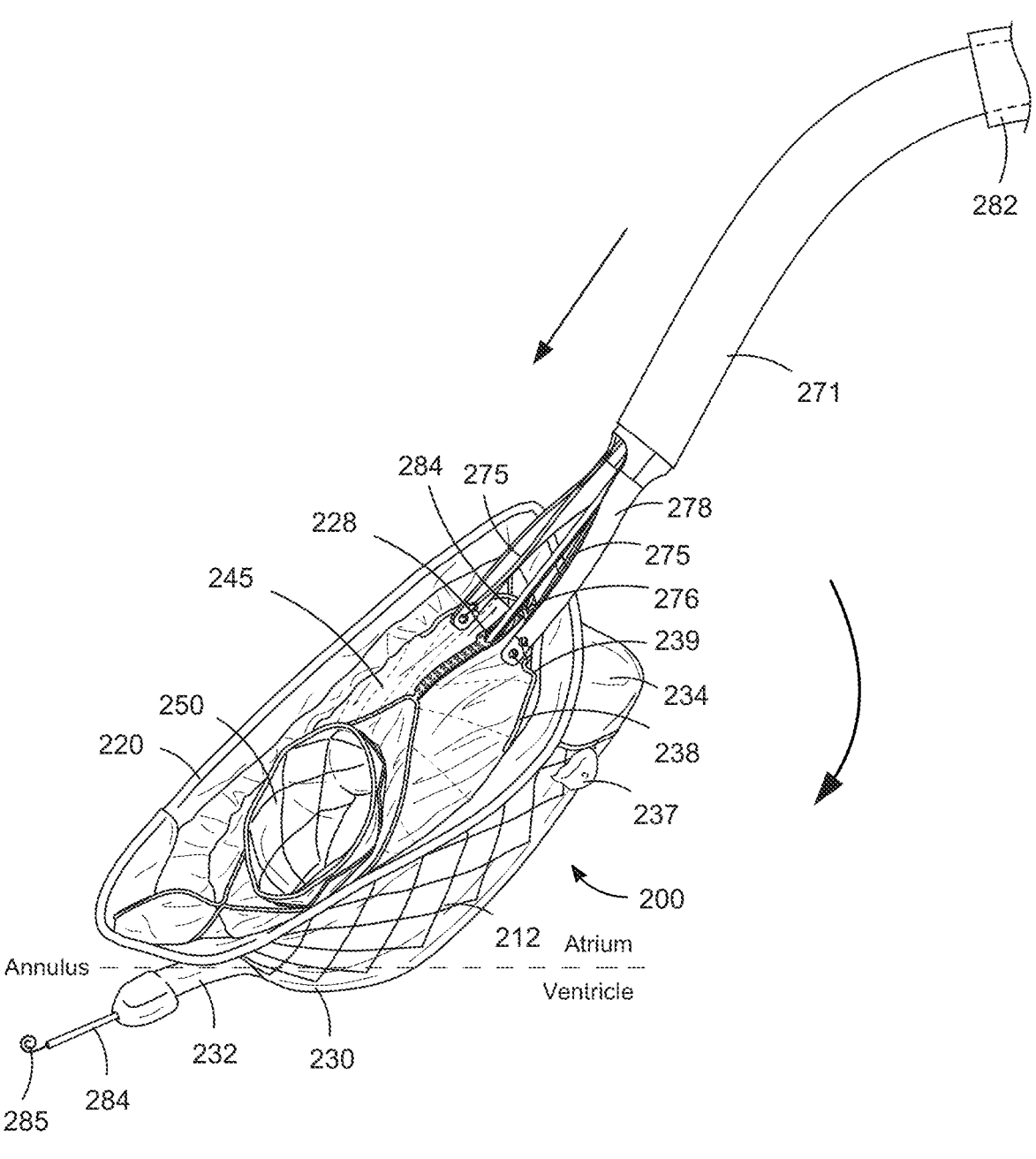

FIGS. 15 and 16 are elevated perspective side views showing the prosthetic valve 200 removably coupled to a control device 270 used to advance, control, and/or retract the valve through a delivery catheter and/or to actuate one or more portions of the valve 200 such as at least the subannular member 230 of the valve frame 210, as described herein. The control device 270 and/or at least a portion thereof includes a control catheter 271 with a connection member 278 coupled to and/or disposed at a distal end. The control catheter 271 can be, for example, a multi-lumen steerable catheter, having one or more components of the control device 270 extending therethrough, as described in detail in the '032 PCT incorporated by reference above. The connection member 278 is removably coupleable to the supra-annular member 220 of the valve frame 210 and thus, connects the valve 200 to the control catheter 271. As described in further detail herein, the control catheter 271 can be manipulated to, for example, advance the prosthetic valve 200 through a delivery catheter (not shown), control or steer the prosthetic valve 200 during deployment, retrieve and/or withdraw the prosthetic valve 200 into the delivery catheter (e.g., after at least partial deployment), and/or the like.

FIG. 15 shows the connection member 278 having a wishbone, yoke, or Y-shape configuration, though other configurations are possible. As such, the connection member 278 can have a first portion, side, and/or arm and a second portion, size, and/or arm opposite the first portion, side, and/or arm. The connection member 278 can be configured to transition between an expanded configuration and a compressed configuration to, for example, allow the control catheter 271 (and the connection member 278 disposed at the distal end thereof) to be advanced through a delivery catheter. The connection member 278 can be formed from any suitable material such as a shape-memory allow like nitinol or the like.

In some embodiments, the connection member 278 can be in contact with and/or removably coupled to the drum 245 of the supra-annular member 220 and/or any other suitable portion of the frame 210 or valve 200. The connection member 278 can removably couple to the valve 200 via sutures, tethers, cables, clips, couplers, and/or any other removable coupling. For example, in some embodiments, the control device 270 can include a set of tethers 275 extending from one or more lumen defined by the control catheter 271. The tethers 275 are shown extending from the control catheter 271, looping through a set of openings defined along or by each side or arm of the connection member 278 (yoke), looping around one or more attachment members 238 of the valve 200, and extending back into the corresponding lumen of the control catheter 271. The attachment member(s) 238 can be formed by, coupled to, and/or extend from the supra-annular member 220 (e.g., the drum 245). In some embodiments, the attachment member 238 of the valve 200 can be a tether, suture, cable, frame structure, and/or the like that can be coupled to and/or extend from a wire frame portion of the supra-annular member 220 or, for example, the drum 245 (or other biocompatible covering). Moreover, the attachment member 238 can form a pair of loops 239 or the like around which the tethers 275 of the control device 270 can be routed or looped.

The looped arrangement of the tethers 275 through and/or around the connection member 278 and the attachment member 238 of the valve 200 is such that each of the proximal end and the distal end of the tether 275 extends through and outside of (e.g., proximal to) a single control arm 277 of the control portion 272. As such, a proximally directed force can be exerted on each of the proximal end and the distal end of the tether(s) 275 to increase a tension along the tether 275, which pulls the connection member 238 toward the drum 245, thereby securing the connection member 278 to the valve. Conversely, a proximally directed force exerted on only one of the proximal end or the distal end of the tether(s) 275 can disengage the tether(s) 275 from the connection member 278 and can withdraw the tether(s) 275 from the control device 270, which in turn, can allow the connection member 278 to be decoupled or removed from the valve 200.

FIG. 15 further shows the guidewire catheter 284 of the delivery system extending through, for example, the waypoint 228 or opening in the supra-annular member 220 and/or drum 245 thereof and extending through the guidewire coupler 233 of the distal anchoring element 232. The guidewire catheter 284 can extend below the flow control component 250 of the valve 200. Prior to and/or as a part of delivery, the guidewire catheter 284 can be advanced and/or inserted through the valve 200 and advanced over the guidewire 285 that is already placed in a desired position within the heart. As such, delivering the valve 200 in a compressed configuration through a delivery catheter includes advancing the guidewire catheter 284 along the guidewire 285. The guidewire catheter 284 can extend through and beyond the guidewire coupler 233 of the distal anchoring element 232 (e.g., a distal end of the guidewire catheter 284 can be distal to the guidewire coupler 233 by about 0.1 cm to about 1.0 cm, or more).

The guidewire catheter 284 can be sufficiently stiff to, for example, limit and/or define (at least in part) a range of motion of the valve 200 during delivery. For example, the guidewire catheter 284 can define an axis about which the valve 200 can rotate during delivery but can substantially limit or oppose movement of the valve 200 in other directions. In some implementations, the arrangement of the connection member 278 (e.g., yoke) and the guidewire catheter 284 can allow for greater control of a position of the valve 200 during delivery. The guidewire catheter 284 and/or one or more portions of the valve 200 (e.g., the subannular member 230) can also include radiopaque markers allowing for enhanced visualization during image guided delivery. For example, in some instances, a radiopaque marker or wire can be placed relative to an annular plane of the native valve and can define a landmark during image guided delivery. In such instances, the radiopaque markers on the guidewire catheter 284 and/or other portion(s) of the valve 200 (e.g., the subannular member 230) can be used to align, orient, locate, index, etc. the valve 200 relative to the landmark, which in turn, corresponds to the annular plane of the native valve. Thus, image guided delivery can allow a user to visualize the valve 200 during delivery and/or deployment and can allow the user to visualize when the valve 200 has been seated in the annulus (e.g., the radiopaque marker bands of the valve 200 are below or in a subannular direction relative to the radiopaque landmark.

FIG. 15 further shows at least one tether 276 (e.g., tethers, sutures, cables, tensile members, and/or the like) extending from the control catheter 271 (e.g., through one or more lumen thereof) and through the waypoint 228. The control device 270 can include a single tether or multiple tethers (e.g., one tether, two tethers, three tethers, four tethers, five tethers, six tethers, seven tethers, eight tethers, nine tethers, ten tethers, or more, each of which can be removably coupled to one or more attachment points on the valve 200). The tether(s) 276 can be configured to actuate and/or transition one or more portions of the valve 200 such as, for example, the subannular member 230 and/or at least the proximal anchoring element 234 thereof. In some embodiments, the tether(s) 276 can extend through the waypoint 228, can be looped around and/or through attachment points along the subannular member 230 or at least the proximal anchoring element, and then can be routed back through the waypoint 228 and the control catheter 271 such that both ends of each tether 276 are outside the patient, thereby allowing manipulation of the tether(s) 276 to actuate the valve 200 and/or to transition a shape of the proximal anchoring element 234, the subannular member 230, and/or other portions of the valve 200 to facilitate seating at least a proximal side of the valve 200 into the native annulus. Said another way, increasing an amount of tension along the tether(s) 276 can be operable to transition at least the subannular member 230 (or portion thereof) between a first configuration and a second configuration. As such, the tether(s) 276 can be actuated (or placed in tension) and/or released in a manner similar to that described above with reference to the tether(s) 275.

FIG. 16 shows the valve 200 and the control device 270 during deployment into a native annulus of the heart. As described above, the control device 270 can advance the valve 200 through the delivery catheter 282 and into the atrium of the heart. In some implementations, the delivery catheter 282 can remain in a substantially fixed position relative to the atrium, or the IVC through which it extends, while a distal end of the control device 270 and the valve 200 are advanced along the guidewire catheter 284 in a distal direction relative to (e.g., away from) the delivery catheter 282 toward the annulus. As such, a length of a portion of the control catheter 271 that is distal to the delivery catheter 282 increases. Because the valve 200 is no longer constrained by the delivery catheter 282, releasing the valve 200 into the atrium allows the valve 200 to transition from the compressed configuration to the expanded configuration.

The control device 270 can be manipulated or steered to place the valve 200 in the expanded configuration at a desired deployment angle in which the distal anchoring element 232 is positioned below the annulus and near, adjacent, and/or at least partially in, for example, a ventricular outflow tract (e.g., the RVOT). At the deployment angle, the supra-annular member 220 of the valve frame 210 and a least a proximal portion of the subannular member 230 of the valve frame 210 remain in the atrium. In some implementations, a distal surface of the transannular member 212 of the valve frame 210 can be placed in contact with native tissue forming a distal surface or wall of the annulus. In some instances, the valve 200 can be temporarily maintained in this partially deployed position (e.g., at the deployment angle) allowing a user to verify the positioning of the valve 200 relative to the angle (e.g., by visualizing radiopaque markers under fluoroscopy) and/or allowing blood flow through the annulus to start to transition from flowing entirely through the native valve to flowing through the flow control component 250. In some instances, this can also allow a user to verify that the flow control component 250 is functioning in a desired manner prior to completely seating the valve 200 in the annulus.

Once the position and/or function of the valve 200 is verified, the control device 270 can be manipulated and/or steered to pivot the valve 200 relative to the annulus such that the proximal portion of the valve 200 is inserted and/or dropped into the annulus. In some implementations, for example, the proximal anchoring element 234 can be in and/or can be transitioned to a compressed configuration such that a perimeter and/or extent of the subannular member 230 of the valve frame 210 is less than a perimeter or extent of the annulus. In some implementations, the control device 270 and/or the control catheter 271 can be manipulated and/or steered such that a distally directed force exerted by a user on the control device 270 results in the connection member 278 pushing the proximal portion of the valve 200 in a direction of the annulus. In some implementations, the pivoting the valve 200 can include "steering" the control catheter 271 such that a distal portion of the control catheter 271 bends relative to a distal end of the delivery catheter 282, allowing the connection member 278 to seat the proximal portion of the valve 200 in the annulus. Once seated, the control device 270 and/or the at least one tether 276 can be actuated to transition the proximal anchoring element 234 to the expanded configuration, as described above with reference to FIG. 15. The delivery/deployment system 280 can then be decoupled from the valve 200 and retracted/removed from the patient, leaving the prosthetic valve 200 in the annulus.

Figure 17:
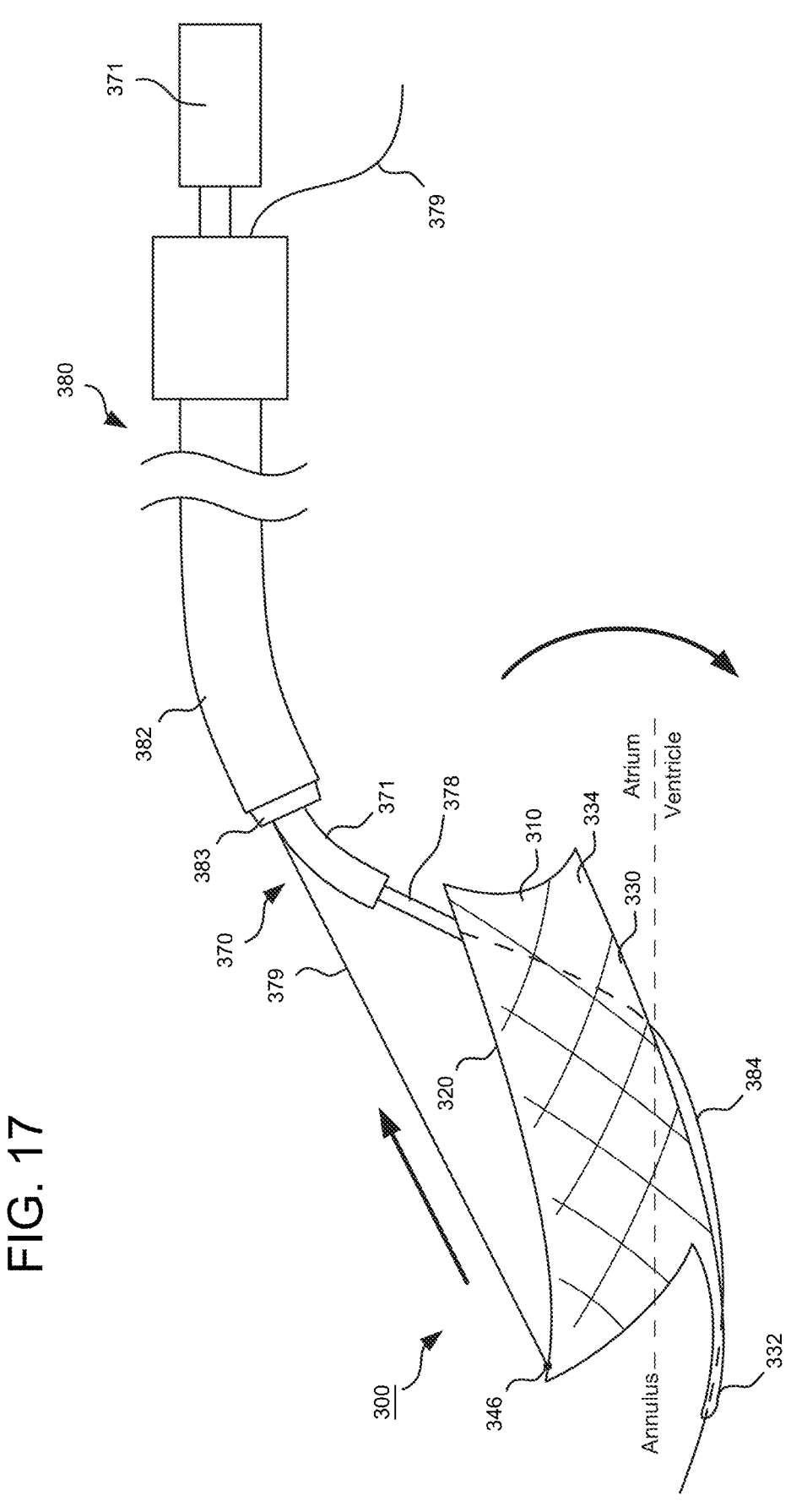
FIG. 17 is a schematic illustration of a side-deliverable
transcatheter prosthetic valve coupled to a delivery system
(or portions thereof) used to deliver and deploy the pros-
thetic valve into an annulus of a native heart valve, accord-
ing to an embodiment.

In some instances, it may be desirable to provide additional support to one or more portions of a prosthetic valve and/or the control device during the deployment process described above with reference to FIG. 16. For example, FIG. 17 is a schematic illustration of a prosthetic valve 300 coupled to the delivery/deployment system 380, according to an embodiment, and shown during the process of deploying the valve 300 in an annulus of a native heart valve. The valve 300 and the delivery/deployment system 380 can be similar to and/or substantially the same as the valve 200 and the delivery deployment system 280, respectively. Thus, the valve 300 (or at least aspects thereof) and the delivery/deployment system 380 (or at least aspects thereof) are not described in further detail herein.

As described above, a control device 370 can include a control catheter 371 with a connection member 378 disposed at a distal end thereof. The connection member 378 is removably coupled to a supra-annular region 320 of the valve 300 (or a valve frame 310 thereof). The coupling, engagement, and/or contact of the connection member 378 and the supra-annular region 320 enables the control device 370 to advance the valve 300 along a guidewire catheter 384 (and/or guidewire disposed in the guidewire catheter 384), through a delivery catheter 382, and into the atrium of the heart. In some implementations, the control device 370 and valve 300 can be disposed within a lumen of a delivery sheath 383, which in turn, is disposed in a lumen of the delivery catheter 382. In such implementations, at least a portion of the delivery sheath 383, at least a portion of the control device 370, and the valve 300 can be advanced through the delivery catheter 382 and into the atrium of the heart, as shown in FIG. 17. In some implementations, the delivery catheter 382 and optionally, the delivery sheath 383, can remain in a substantially fixed position relative to the atrium, or the IVC through which the delivery catheter 382 extends, while a distal end of the control device 370 and the valve 300 are advanced along the guidewire catheter 384 in a distal direction relative to (e.g., away from) the delivery catheter 382 toward the annulus. As such, a length of a portion of the control catheter 371 that is distal to the delivery catheter 382 and/or the delivery sheath 383 increases. Because the valve 300 is no longer constrained by the delivery catheter 382 and/or the delivery sheath 383, releasing the valve 300 into the atrium allows the valve 300 to transition from the compressed configuration to the expanded configuration.

The control device 370 can be manipulated or steered to place the valve 300 (in the expanded configuration) at a desired deployment angle in which a distal anchoring element 332 is positioned below the annulus and near, adjacent, and/or at least partially in, for example, a ventricular outflow tract (e.g., the RVOT). At the deployment angle, a supra-annular region 320 of the valve frame 310 and a least a proximal portion of a subannular region 330 of the valve frame 310 remain in the atrium. In some implementations, a distal surface of a transannular region 312 of the valve frame 310 can be placed in contact with native tissue forming a distal surface or wall of the annulus. In some instances, the valve 300 can be temporarily maintained in this partially deployed position (e.g., at the deployment angle) allowing a user to verify the positioning of the valve 300 relative to the angle (e.g., by visualizing radiopaque markers under fluoroscopy) and/or allowing blood flow through the annulus to start to transition from flowing entirely through the native valve to flowing through the flow control component 350. In some instances, this can also allow a user to verify that the flow control component 350 is functioning in a desired manner prior to completely seating the valve 300 in the annulus.

As described above with reference to the valve 200, the guidewire catheter 384 extending through and below a portion of the valve 300 and out of the distal anchoring element 332 can provide support to at least a portion of the valve 300 during deployment. For example, the guidewire catheter 384 can define an axis about which the valve 300 can rotate while movement of the valve 300 in other directions may be at least partially constrained. In addition to the support provided by the guidewire catheter 384, the delivery/deployment system 380 shown in FIG. 17 also includes a supra-annular support 379 configured to support at least a portion of the valve 300. In some embodiments, the supra-annular support 379 (also referred to herein as "support") can extend through the lumen of the delivery sheath 383. A proximal end of the support 379 is proximal to and/or outside of a proximal end of the delivery catheter 382, thereby allowing a user to manipulate the support 379. A distal end of the support 379 is removably coupleable to a supra-annular portion of the valve 300 and/or valve frame 310. Moreover, the support 379 can extend through the lumen of the delivery sheath 383 while being outside of or otherwise not directly attached to the control device 370. In some implementations, such an arrangement can allow the support 379 to form a supportive connection between a supra-annular portion of the valve 300 and the delivery sheath 383 while allowing the control device 370 to move, transition, and/or otherwise reconfigure to control and deploy the valve 300 into the annulus.

FIG. 17 shows the support 379 removably coupled to an attachment point 346 at or along a distal portion of the supra-annular region 320 of the valve frame 310. The support 379 can be any suitable feature, component, member, device, mechanism, and/or the like configured to support at least a portion of the valve 300 during deployment into the annulus. In some embodiments, the support 379 can be one or more tethers, sutures, tensile members, rods, cables, tubes, catheters, and/or the like or combinations thereof. In some embodiments, the support 379 can be one or more reconfigurable members configured to transition from a first state/configuration (e.g., during delivery through the delivery catheter 382) to a second state/configuration (e.g., during deployment into the annulus). For example, the support 379 can be relatively flexible when in the first state and can be relatively rigid when in the second state, thereby forming a substantially rigid connection between the attachment point 346 and a distal end portion of the delivery sheath 383.

In some embodiments, the support 379 is configured to transition to the second/support configuration in response to being placed under tension after the valve 300 is released from the delivery catheter 382 and allowed to expand to the expanded/deployment configuration. In embodiments where the support 379 is or includes one or more tethers, the tethers can be similar to or substantially the same as the tethers 275 and/or 276 described above with reference to FIG. 15. As such, a proximally directed force can be exerted on the proximal end portion of the support 379 (one or more tethers) that can increase a tension along at least a portion of the support 379, thereby transitioning the support 379 to its second configuration. In some implementations, the support 379 in the second or support state or configuration can stabilize at least a portion of the valve 300, which in combination with the support provided by the guidewire catheter 384, can provide increased control of the valve 300 when moving and/or positioning the valve 300 into the annulus via the control device 370. In addition, in some implementations, the support 379 in the second configuration can provide support to at least the distal supra-annular portion of the valve 300 that can, for example, resist, limit, and/or otherwise prevent the distal supra-annular portion of the valve 300 (and/or the distal portion of the supra-annular region 320 of the valve frame 310) from dropping into the annulus.

With the distal portion of the valve 300 in a desired position within the annulus (and optionally, after verifying the position and/or function of the valve, as described above), the control device 370 can be manipulated and/or steered to pivot the valve 300 such that the proximal portion of the valve 300 is inserted and/or dropped into the annulus. For example, a proximal anchoring element 334 can be in and/or can be transitioned to a compressed configuration such that a perimeter and/or extent of the subannular region 330 of the valve frame 310 is less than a perimeter or extent of the annulus. In some implementations, the control device 370 and/or the control catheter 371 can be manipulated and/or steered such that a distally directed force exerted by a user on the control device 370 results in a connection member 378 at the end of the control catheter 371 pushing the proximal portion of the valve 300 in a direction of the annulus. In some implementations, the pivoting the valve 300 can include "steering" the control catheter 371 such that a distal portion of the control catheter 371 bends relative to a distal end of the delivery catheter 382 and/or delivery sheath 383, allowing the control device 370 to seat the proximal portion of the valve 300 in the annulus.

In some implementations, the support 379, and/or the substantially rigid and/or supporting connection between the attachment point 346 at or along the distal supra-annular portion of the valve 300 and the distal end of the delivery sheath 383 through which the support 379 extends (e.g., outside of or substantially independent of the control device 370), can result in a reaction/opposing force in response to the force exerted by, and/or the bending of, the control catheter 371 operable to pivot or seat at least the proximal portion of the valve 300 in the annulus. In some instances, such an arrangement can reduce relative movement of at least a portion of the control device 370 that does not contribute to the deployment of the valve 300, thereby facilitating the deployment process. For example, while the distal end portion of the control catheter 371 is distally advanced and movable relative to the delivery catheter 382, the distal end portion of the delivery sheath 383 can be in a substantially fixed position relative to the delivery catheter 382.

With the support 379 extending through the lumen of delivery sheath 383 outside of the control catheter 371, the support 379 in the second configuration can form a substantially rigid or substantially fixed-length connection between the attachment point 346 and the delivery sheath 383. The substantially rigid or substantially fixed-length connection, in turn, limits and/or substantially prevents the distal supra-annular portion of the valve 300 from dropping into the annulus while also at least partially directing and/or controlling the bending and/or moving of the distal end portion of the control catheter 371 in a manner that facilitates seating the proximal portion of the valve 300 in the annulus. In some instances, the substantially rigid or substantially fixed-length connection can also limit and/or substantially prevent a portion of the control catheter 371 from pushing away from the annulus, which may otherwise result in the anatomy of the heart (e.g., the IVC) supporting the control catheter 371. In some instances, the placement of the distal anchoring element 332 in, for example, the RVOT and the coupling of the support 379 to the attachment point 346 collectively act to anchor, constrain, secure, and/or otherwise control at least the distal portion of the valve 300 allowing the proximal portion of the valve 300 to pivot into the annulus.

Once valve 300 is seated in the annulus, the control device 370 and/or at least one actuator, tether, tensile member, etc. can be actuated to transition the proximal anchoring element 334 to the expanded configuration (or to otherwise allow the proximal anchoring element 334 to transition), as described above with reference to valve 200 shown in FIG. 15. In some implementations, fully seating the valve 300 as just described is sufficient to secure the valve 300 in the annulus. In other implementations, one or more portions of the valve 300 can be cinched or actuated to, for example, engage native tissue and/or sandwich native tissue forming the annulus, thereby securing the valve 300. With the valve 300 secured in the annulus, the delivery/deployment system 380 can be decoupled from the valve 300 and retracted/removed from the patient, leaving the prosthetic valve 300 in the annulus.

In some implementations, the support 379 can be removably coupled to the valve 300 at the attachment point 346 in a manner that allows the support 379 to be decoupled from the valve and retracted with at least one of the guidewire catheter 384, the control device 370, and/or the delivery sheath 383. For example, the support 379 can be and/or can include a tether that is "looped" through or around the attachment point 346 such that each of the proximal and distal ends of the tether (support 379) is disposed proximal to the delivery catheter 382 and outside the body, as described above with reference to the tethers 275 and/or 276. In some implementations, the support 379 can be and/or can include a tether with the distal end portion of the support 379 removably coupled to the attachment point 346 while the proximal end of the support 379 is disposed outside the body (e.g., the tether and/or support 379 is not "looped" around the attachment point as described above with reference to the tethers 275 and/or 276. In some such implementations, the distal end portion of the support 379 can be wrapped around the attachment point 346 or any other portion of the valve 300, thereby allowing the support 379 to be unwrapped or otherwise decoupled from the valve 300 without having to pull one side of the support 379 through the delivery/deployment system 380, as may be the case when the support 379 is "looped." In some implementations, the attachment point 346 can be a breakaway suture and/or any other suitable temporary attachment that allows the distal end portion of the support 379 to be detached and/or decoupled. In some implementations, the arrangement can be such that the distal end of the support 379 (e.g., a tether or any other form of the supra-annular support) is decoupled from the valve 300 and retracted into the delivery sheath 383 without pulling the support 379 all the way out of the delivery sheath 383. In this manner, the support 379 can be retracted and/or removed from the patient as the delivery catheter 382 and/or delivery sheath 383 is retracted and/or removed.

While the support 379 is described above as being transitioned from the first configuration to the second configuration to, for example, form a substantially rigid or substantially fixed-length connection between the delivery sheath 383 and the attachment point 346 on the valve 300, in other embodiments, the support 379 or at least a portion thereof can be formed from a material that can provide a desired amount of rigidity without transitioning between one or more states or configurations. For example, in some embodiments, the support 379 or at least a portion thereof can be formed from a metal (e.g., stainless steel or the like) or a relatively hard polymer. In some embodiments, the support 379 can include a tether that is at least partially disposed in a catheter having a desired durometer or the like (e.g., similar to the arrangement of the guidewire and guidewire catheter described above with reference to the valve 200 shown in FIGS. 7-16). In some implementations, having a catheter disposed about a portion of the tether can provide sufficient rigidity to allow a user to exert, for example, a distally directed force on the supra-annular region 320 of the valve 300 and/or valve frame 310. For example, with the support being coupled to a distal supra-annular portion of the valve 300, the distally-directed force can be used to push at least the distal supra-annular portion of the valve 300 and/or valve frame 310 into a desired position relative to the annulus (or to aid the advancement of the valve 300 through the delivery sheath 383 and/or delivery catheter 382).

Figure 18:
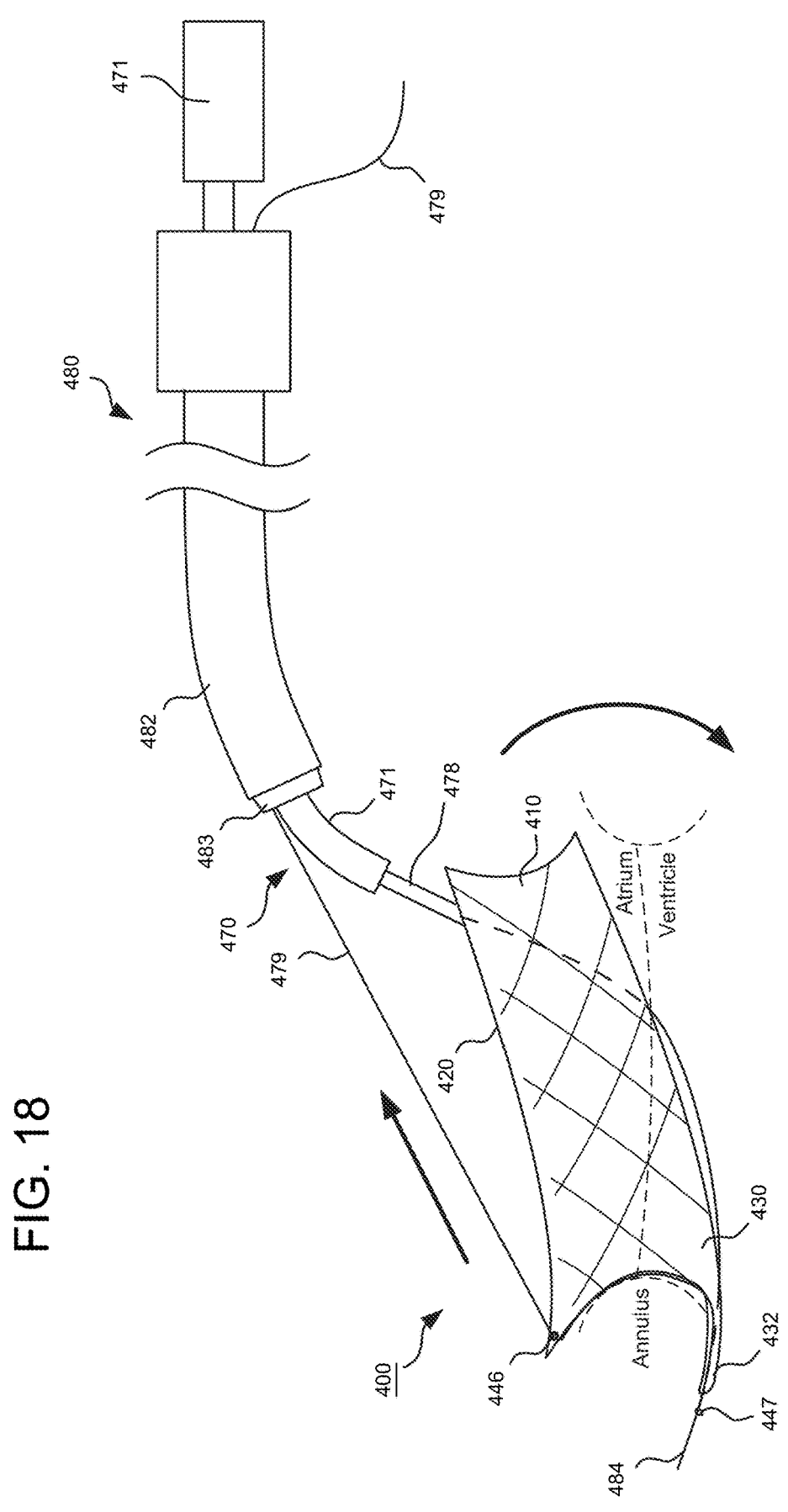
FIG. 18 is a schematic illustration of a side-deliverable
transcatheter prosthetic valve coupled to a delivery system
(or portions thereof) used to deliver and deploy the pros-
thetic valve into an annulus of a native heart valve, accord-
ing to an embodiment.

FIG. 18 is a schematic illustration of a prosthetic valve 400 coupled to the delivery/deployment system 480, according to another embodiment, and is shown during the process of deploying the valve 400 in an annulus of a native heart valve. The valve 400 and the delivery/deployment system 480 can be similar to and/or substantially the same as the valve 300 and the delivery/deployment system 380, respectively. Thus, the valve 400 (or at least aspects thereof) and the delivery/deployment system 480 (or at least aspects thereof) are not described in further detail herein.

As described above, a control device 470 can include a control catheter 471 with a connection member 478 disposed at a distal end thereof. The connection member 478 is removably coupled to a supra-annular region 420 of the valve 400 (or a valve frame 410 thereof). The coupling, engagement, and/or contact of the connection member 478 and the supra-annular region 420 enables the control device 470 to advance the valve 400 along a guidewire catheter 484 (and/or guidewire disposed in the guidewire catheter 484), through a delivery catheter 482, and into the atrium of the heart. The delivery catheter 482 and optionally, the delivery sheath 483, can remain in a substantially fixed position relative to the atrium, or the IVC through which the delivery catheter 482 extends, while a distal end of the control device 470 and the valve 400 are advanced along a guidewire catheter 484 in a distal direction relative to (e.g., away from) the delivery catheter 482 toward the annulus. As such, a length of a portion of the control catheter 471 that is distal to the delivery sheath 483 increases. Because the valve 400 is no longer constrained by the delivery catheter 482 and/or the delivery sheath 483, releasing the valve 400 into the atrium allows the valve 400 to transition from the compressed configuration to the expanded configuration.

The control device 470 can be manipulated or steered to place the valve 400 in the expanded configuration at a desired deployment angle in which a distal anchoring element 432 is positioned below the annulus and near, adjacent, and/or at least partially in, for example, a ventricular outflow tract (e.g., the RVOT). At the deployment angle, a supra-annular region 420 of the valve frame 410 and a least a proximal portion of a subannular region 430 of the valve frame 410 remain in the atrium. In some implementations, a distal surface of a transannular region 412 of the valve frame 410 can be placed in contact with native tissue forming a distal surface or wall of the annulus. In some instances, the valve 400 can be temporarily maintained in this partially deployed position (e.g., at the deployment angle) allowing a user to verify the positioning of the valve 400 relative to the angle (e.g., by visualizing radiopaque markers under fluoroscopy) and/or allowing blood flow through the annulus to start to transition from flowing entirely through the native valve to flowing through the flow control component 450. In some instances, this can also allow a user to verify that the flow control component 450 is functioning in a desired manner prior to completely seating the valve 400 in the annulus.

As described above with reference to the delivery/deployment system 380, the delivery/deployment system 480 shown in FIG. 18 includes a support 479 configured to provide support to one or more portions of the valve 400 during deployment. The support 479 can extend through the lumen of the delivery sheath 483 and outside of the control device 470. A proximal end of the support 479 is proximal to and/or outside of the delivery catheter 482, thereby allowing a user to manipulate the support 479. A distal end of the support 479 is removably coupleable to and/or is otherwise configured to selectively engage a distal portion of the valve 400 and/or valve frame 410.

The support 479 can be similar to and/or substantially the same as the support 379 described above with reference to FIG. 17. For example, the support 479 can be and/or can include one or more tethers, sutures, cables, rods, tensile members, tubes, catheters, and/or the like or combinations thereof. In some embodiments, the support 479 can be configured to transition to a support configuration in response to being placed under tension, as described in detail above with reference to the support 379. However, while the support 379 is described above as being removably coupled to the attachment point 346 at or along the distal portion of the supra-annular region 320 of the valve frame 310, the distal portion of the support 479 shown in FIG. 18 can engage and/or can be at least temporarily secured to the distal portion of the valve 400 via one or more other features, components, members, securements, coupling mechanisms, etc.

For example, FIG. 18 shows the distal portion of the support extending through an attachment or anchoring point 446, which in this embodiment, is a hole, an opening, an aperture, a slit, a waypoint, a passthrough, and/or the like. The distal portion of the support 479 extends outside of the valve frame 410 along an outer surface or wall. The distal end of the support 479 is shown as including and/or forming a loop, hoop, ring, etc. that is disposed over a guidewire catheter 484 (at least during deployment). Said another way, the loop at the distal end of the support 479 receives and/or otherwise allows the guidewire catheter 484 to extend therethrough. In some implementations, routing the distal portion of the support 479 along a distal wall of the valve 400 from the supra-annular member or region 420 of the valve frame 410 to the subannular member or region 430 of the valve frame 410 can result in the distal portion of the support 479 being sandwiched or trapped between the wall of the valve 400 and native tissue forming a portion of the annulus, which in turn, can anchor and/or secure the support 479 to the distal portion of the valve 400 (e.g., in a manner similar to the support 379 removably coupling to the attachment point 346).

For example, FIG. 18 shows the distal anchoring element 432 of the subannular region 430 below the annulus at, near, or at least partially within the ventricular outflow tract (e.g., the RVOT), while the remaining portions of the valve 400 are in the atrium. Positioning the distal anchoring element 432 in the ventricle (e.g., in the RVOT) can be such that the distal portion or surface of the valve 400 is placed in contact with and/or adjacent to a distal surface of the native tissue forming the annulus. Thus, the contact between the surface of the valve 400 and the surface to the annular tissue can sandwich, pinch, retain, constrain, anchor, and/or otherwise substantially secure the distal portion of the support 479 to the distal portion of the valve 400, thereby allowing the support 479 to be in and/or to be transitioned to the second or support state/configuration (e.g., by placing the support under tension, as described in detail above).

In some embodiments, the support 479 can be formed from a material that can provide a desired rigidity and/or that can define a substantially fixed length without transitioning (e.g., without being placed under tension). In some embodiments, the support 479 can include a tether that is disposed in a tube, catheter, conduit, etc. along a portion proximal to the attachment and/or passthrough point 446 (e.g., similar to the guidewire and guidewire catheter arrangement described above with reference to the valve 200). In such embodiments, the tube, catheter, conduit, etc. can provide a desired rigidity and/or can define the substantially fixed-length between the delivery sheath 483 and the attachment and/or passthrough point 446, while a distal portion of the tether can extend through the attachment and/or passthrough point 446 to allow the loop and/or ring 479B to be disposed about the guidewire catheter 484. Moreover, at least the distal portion of the tether can be relatively flexible allowing the tether to bend, flex, and/or reconfigure based on a shape of the outer wall of the valve 400 and/or the native tissue forming a portion of the annulus (e.g., when being sandwiched, pinched, constrained, compressed, etc.).

With the portion of the support 479 that is distal to the attachment point 446 (e.g., the hole, waypoint, passthrough, etc.) being secured or anchored, the portion of the support between the attachment point 446 and the delivery sheath 483 can function in substantially the same manner as described above with reference to the support 379. Thus, the support 479 can provide support to at least the distal portion of the valve 400 that can resist, limit, and/or otherwise prevent the distal supra-annular portion of the valve 400 and/or valve frame 410 from dropping into the annulus; can at least partially direct and/or control the bending and/or moving of a distal end portion of the control device 470 in a manner that facilitates seating the proximal portion of the valve 400 in the annulus; can limit and/or substantially prevent a portion of the control device 470 from pushing away from the annulus; and can provide a reaction point, pivot point, fulcrum, etc., that can facilitate the proximal portion of the valve 400 being pivoted or "dropped" into the annulus, as described above with reference to the support 379.

Once the valve 400 is secured in the annulus, the delivery/deployment system 480 (including the control device 470, the support 479, the guidewire catheter 484, and/or any other portion or component of the delivery/deployment system 480) can be decoupled from the valve 400 and retracted/removed from the patient, leaving the prosthetic valve 400 in place. In some implementations, with the loop or ring 479B at the distal end of the support 479 being disposed about the guidewire catheter 484, withdrawing the guidewire catheter 484 from the distal anchoring element 432 into the delivery/deployment system 480 (e.g., proximal to the valve 400) releases the distal end of the support 479. Accordingly, the support 479 can be retracted in a proximal direction such that the distal end of the support 479 is pulled through the attachment point 446 (e.g., opening, hole, waypoint, passthrough, etc.). In some instances, the distal end of the support 479 can be withdrawn or retracted into the lumen of the delivery sheath 483 prior to removing the delivery/deployment system 480 from the body of the patient. In other instances, the support 479 is not retracted into the delivery sheath 483 (e.g., the support can be pulled behind the rest of the delivery/deployment system 480 as it is withdrawn from the body of the patient).

Figure 19:
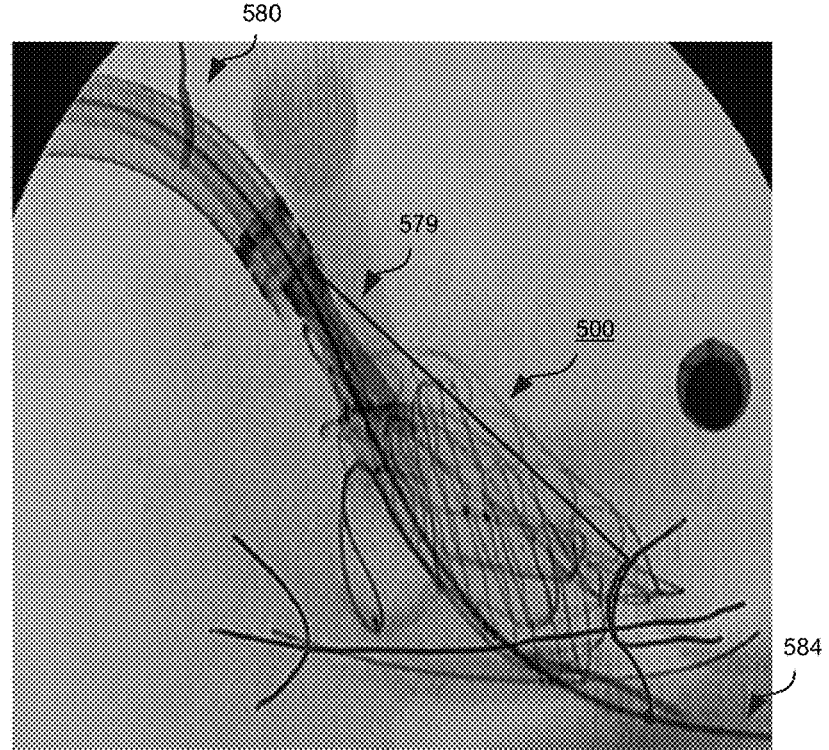
FIGS. 19 and 20 are side view fluoroscopic images
showing the delivery system engaging the prosthetic valve
during deployment, shown in a state prior to seating the
valve in the annulus (FIG. 19) and in a state during and/or
after at least partially seating the valve in the annulus (FIG.
20).
Figure 20:
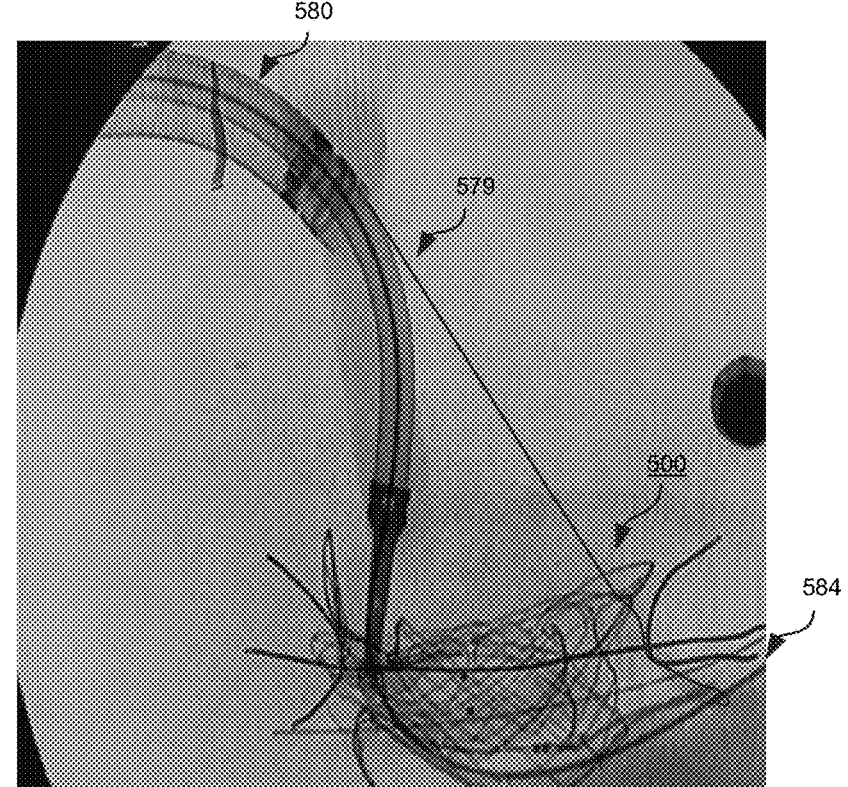

FIGS. 19 and 20 are side view fluoroscopic images showing a delivery/deployment system 580 engaging a prosthetic valve 500 during deployment, according to an embodiment. FIG. 19 shows the valve 500 in a state prior to fully inserting and/or seating the valve 500 in an annulus of a native heart valve. FIG. 20 shows the valve 500 in a state during and/or after inserting and at least partially seating the valve 500 in the annulus. The delivery/deployment system 580 includes a support 579 (e.g., a distal support, a supra-annular support, and/or the like) that can be passed through a distal supra-annular portion of the valve 500 and looped or removably coupled to a guidewire catheter 584, as described in detail above with reference to the valve 400. In other implementations, the support 579 can be configured to removably couple to an attachment point or the like at or along distal supra-annular portion of the valve 500, as described in detail above with reference to the valve 300.

In some implementations, the support 579 can be formed of a radiopaque material or can include portions formed of a radiopaque material, allowing visualization of the support 579 (or at least portions thereof) under fluoroscopy or other image-guided procedures, as shown in FIGS. 19 and 20. In some implementations, the support 579 can be and/or can include a tether that is at least partially disposed in a tube or catheter. The tube or catheter can, in turn, be formed of a radiopaque material and/or any other material allowing visualization during image-guided procedures like fluoroscopy. As described above, at least a portion of the support 579 between a delivery sheath or catheter of the delivery/ deployment system 580 and the attachment and/or pass-through point on the valve 500 can be in and/or can be placed in a substantially rigid and/or substantially fixed-length state or configuration during deployment that can reduce a likelihood of the distal supra-annular portion of the valve 500 dropping into the annulus during deployment; can reduce and/or limit undesirable motion of the valve relative to the delivery/deployment system 580; and/or can reduce and/or limit undesirable motion of at least a portion of the delivery/deployment system 580 as a proximal portion of the valve 500 is being pushed or pivoted into the annulus. Accordingly, the support 579 can be similar to and/or substantially the same as the supports 379 and/or 479 described in detail above with reference to FIGS. 17 and 18, respectively.

While the supports 379, 479, and 579 are shown as being coupled to and/or otherwise supporting a distal supra-annular region of the valves 300, 400, and 500, respectively, it should be understood that such embodiments are presented by way of example only and not limitation. Any of the valves and/or delivery/deployment systems described herein can be used with a support that is at least temporarily coupled to any suitable portion of the valve and/or at any suitable position along a supra-annular region of the valve. Moreover, the valves and/or delivery/deployment systems described herein can be used with any suitable number of supports having any suitable configuration (or combination of different configuration).

Figure 21:
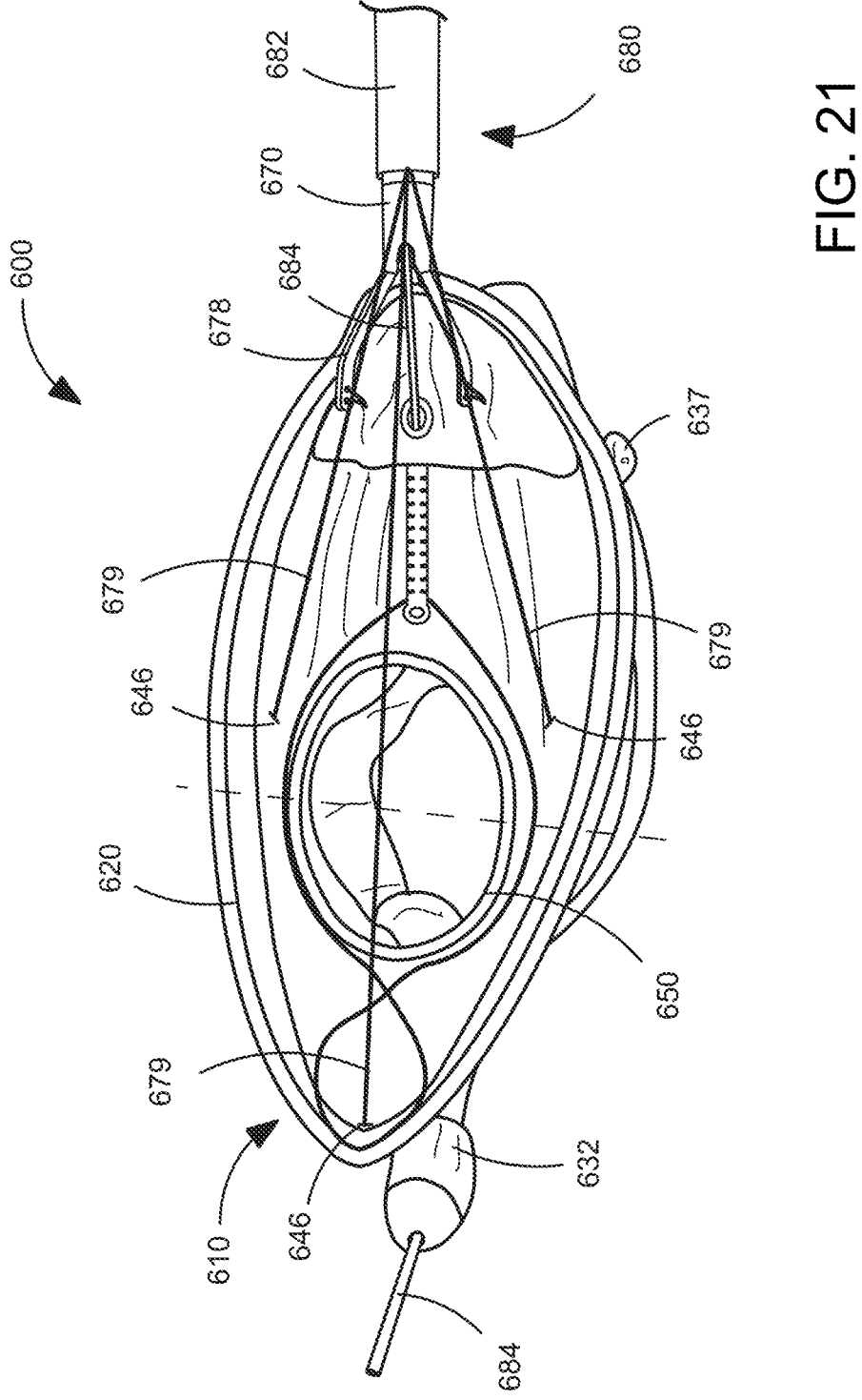
FIG. 21 is a top perspective view of a side-deliverable
transcatheter prosthetic valve coupled to a delivery system
(or portions thereof) used to deliver and deploy the pros-
thetic valve into an annulus of a native heart valve, accord-
ing to an embodiment.

For example, FIG. 21 is a schematic illustration of a prosthetic valve 600 coupled to a delivery/deployment system 680 that includes multiple supra-annular supports. The valve 600 and the delivery/deployment system 680 can be similar to and/or substantially the same as the valves 300, 400, and/or 500 and the delivery/deployment systems 380, 480, and/or 580, respectively. Thus, the valve 600 (or at least aspects thereof) and the delivery/deployment system 680 (or at least aspects thereof) are not described in further detail herein.

As described above, a control device 670 can advance the valve 600 along a guidewire catheter 684 (and/or guidewire) and through a delivery catheter 682 and/or delivery sheath (not shown) and into the atrium of the heart. The delivery catheter 682 and optionally, the delivery sheath, can remain in a substantially fixed position relative to the atrium, or the IVC through which the delivery catheter 682 extends, while a distal end of the control device 670 and the valve 600 are advanced along the guidewire catheter 684 in a distal direction relative to (e.g., away from) the delivery catheter 682 toward the annulus. Because the valve 600 is no longer constrained by the delivery catheter 682 and/or the delivery sheath, releasing the valve 600 into the atrium allows the valve 600 to transition from a compressed configuration to an expanded configuration. The control device 670 can then be manipulated or steered to seat and/or deploy the valve 600 into the annulus of the native heart valve, as described in detail above.

The embodiment shown in FIG. 21 includes multiple supports 679 that are coupled to a supra-annular region 620 of the valve 600 (or a valve frame 610 thereof). As described above, the supports 679 are configured to provide support to one or more portions of the valve 600 during deployment. The supports 679 can be similar to and/or substantially the same as the support 379, 479, and/or 579 described above. For example, each of the supports 679 can be and/or can include one or more tethers, sutures, cables, rods, tensile members, tubes, catheters, and/or the like or combinations thereof. As described above, the supports 679 can be configured to transition to a support configuration in response to being placed under tension or can be formed from a material that can provide a desired rigidity and/or that can define a substantially fixed length without transitioning (e.g., without being placed under tension).

The supports 679 are configured to extend through the lumen of the delivery catheter 682 and/or delivery sheath (not shown) and outside of the control device 670. A proximal end of each support 679 is proximal to and/or outside of the delivery catheter 682, thereby allowing a user to manipulate each support 679. A distal end of each support 679 is removably coupleable to and/or is otherwise configured to selectively engage an attachment point 646 along the supra-annular region 620 of the valve frame 610. The supports 679 can removably couple to the supra-annular region 620 in any suitable manner. In some embodiments, one or more of the supports 679 can be tethers that are looped around the attachment points 646 in a manner similar to the tethers 275 and 276 described above (e.g., double-backed such that both ends of the supports are proximal to the delivery catheter 682). In some embodiments, a distal end of one or more of the supports 649 can be wrapped around a corresponding attachment point without being "looped." In some embodiments, one or more attachment point 646 can be an opening through which a portion of a corresponding support 679 can extend, as described above with reference to the support 479. In some embodiments, the supports 679 can be removably coupled to the supra-annular region 620 of the valve frame 610 using any combination of attachment methods. For example, an attachment point 646 at or near a distal end of the supra-annular region 620 can be an opening allowing a portion of the corresponding support 679 to extend therethrough. In some implementations, the end of the support 679 can have a loop allowing it to be disposed about or around the guidewire catheter 684, as described above with reference to the support 479. In this example, the other attachment points 646 can be sutures configured to be temporarily coupled to the corresponding supports 679.

The example shown in FIG. 21 includes a distal supra-annular support 679 and two additional supports 679. The distal supra-annular support 679 is coupled to and/or otherwise engages the attachment point at or near the distal end of the supra-annular region 620 (referred to as the "distal attachment point") can be similar to or substantially the same as the support 379 or 479 and thus is not described in further detail. The additional supports 679 are shown as extending from the delivery catheter 682 (or delivery sheath) to attachment points at positions along the supra-annular region 620 that are at or near opposite lateral extents of the supra-annular region 620. In other words, the attachment points 646 are at or near the lateral edges or perimeter of the supra-annular region 620 (referred to as the "lateral attachment points"). In addition, the attachment points 646 are laterally outward of, and distal to, the connection member 678 of the control device 670. More particularly, the lateral attachment points 646 are shown as being laterally outward of the flow control component 650 and proximal to a center of the flow control component 650 (represented in FIG. 21 by the dashed line). In other embodiments, the lateral attachment points 646 can be at any position along a section of the supra-annular region 620 between the flow control component 650 and the lateral edge or perimeter.

As described above, the supports 679 are configured to support and/or stabilize the valve 600 during deployment. In some implementations, the support coupled to and/or otherwise engaging the distal attachment point 646 can be configured to support at least a distal portion of the valve 300 and can restrict, limit, and/or substantially prevent the distal supra-annular portion of the valve 300 from dropping into the annulus, as described above with reference to the supports 379, 479, and 579. The supports 679 coupled to and/or otherwise engaging the lateral attachment points 646 can similarly provide support and/or stability to at least a portion of the valve 300. For example, the supports 679 that are removably coupled to the lateral attachment points 646 can support and/or stabilize the valve 600 against and/or with respect to lateral movement or orientation, axial alignment with a centerline of the annular plane, rotation about an axis defined at least in part by the guidewire catheter 684, and/or the like. In some implementations, the attachment points 646 being laterally outward of the connection member 678 result in the supports 679 engaging the supra-annular region 620 at a wider point, which in turn, may allow for increased sensitivity with respect to adjusting a rotational position, orientation, and/or angle of the valve 600 relative to the axis defined by the guidewire catheter 684 and/or an annular plane.

While FIG. 21 is shown as including three supports 679, it should be understood that the embodiment is provided by way of example only and not limitation. For example, valve 600 and delivery/deployment system 680 can be configured for use with more than three supports 679 or fewer than three supports 679. In some embodiments, for example, the valve 600 and the delivery/deployment system 680 can be used with the supports removably coupled to the lateral attachment points 646 without the support 679 removably coupled to the distal attachment point 646. In some embodiments, a position of the lateral attachment points 646 can be modified to be distal to the centerline of the flow control component 650, which may allow the supports 679 coupled thereto to provide the lateral support/stability described above as well as restricting, limiting, and/or substantially preventing the distal supra-annular portion of the valve 600 from dropping into the annulus. In other words, the lateral attachment points 646 may be disposed along the supra-annular region 620 in positions that allow the supports 679 to support the valve 600 in a manner otherwise provided by a support 679 removably coupled to the distal attachment point. In other embodiments, the valve 600 can include attachment points at any other suitable position along the supra-annular region 620 and/or along any other portion of the valve 600.

Figure 22:
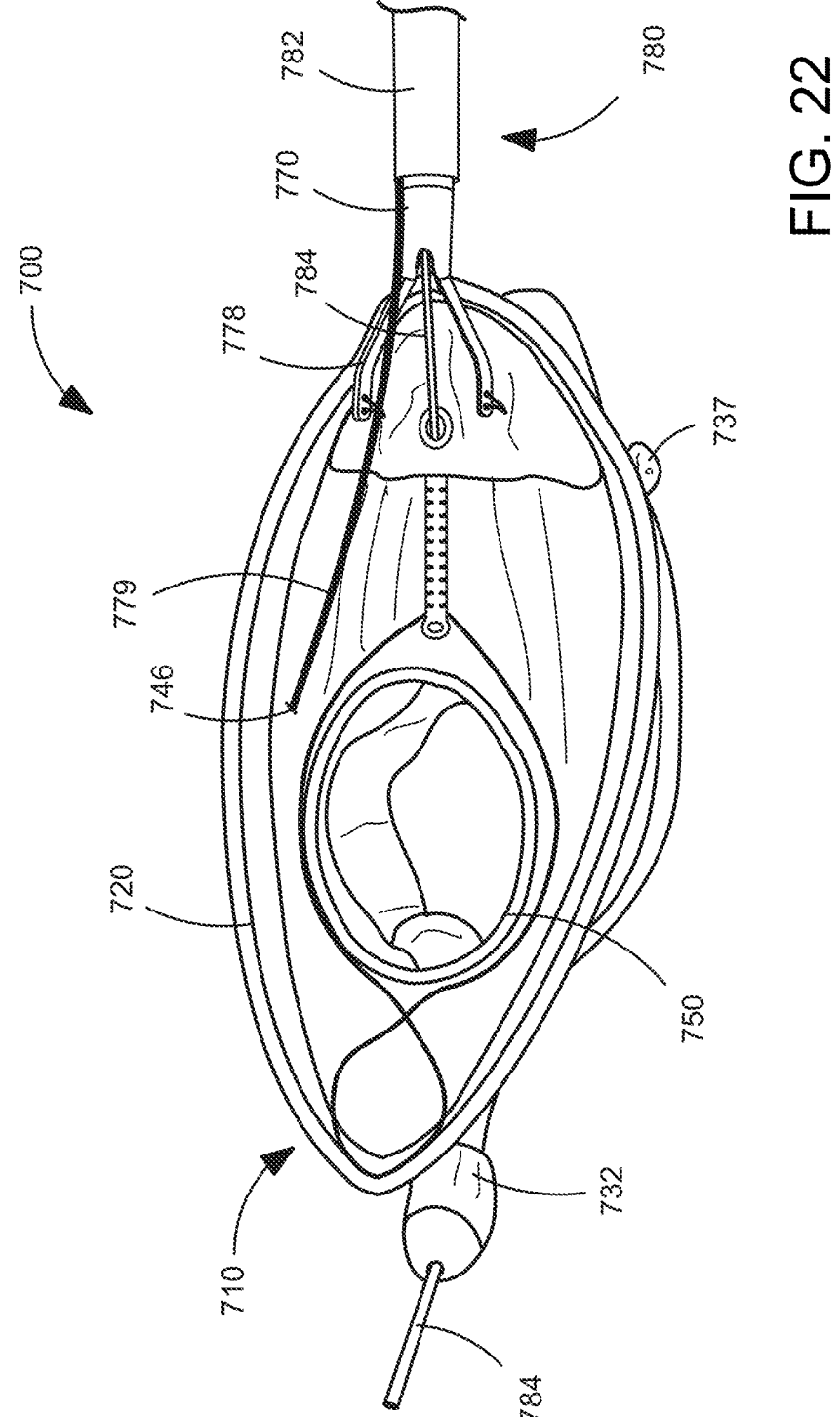
FIG. 22 is a top perspective view of a side-deliverable
transcatheter prosthetic valve coupled to a delivery system (or portions thereof) used to deliver and deploy the pros-
thetic valve into an annulus of a native heart valve, accord-
ing to an embodiment.

FIG. 22 is a schematic illustration of a prosthetic valve 700 coupled to a delivery/deployment system 780 that includes a supra-annular support 779, according to an embodiment. The valve 700 (or at least aspects thereof) and the delivery/deployment system 780 (or at least aspects thereof) can be similar to and/or substantially the same as the valves 300, 400, 500, and/or 600 and the delivery/deployment systems 380, 480, 580, and/or 680, respectively. Thus, the valve 700 (or at least aspects thereof) and the delivery/deployment system 780 (or at least aspects thereof) are not described in further detail herein.

As described above, a control device 770 can advance the valve 700 along a guidewire catheter 784 (and/or guidewire) and through a delivery catheter 782 and/or delivery sheath (not shown) and into the atrium of the heart. The delivery catheter 782 and optionally, the delivery sheath, can remain in a substantially fixed position relative to the atrium, or the IVC through which the delivery catheter 782 extends, while a distal end of the control device 770 and the valve 700 are advanced along the guidewire catheter 784 in a distal direction relative to (e.g., away from) the delivery catheter

782 toward the annulus. Because the valve 700 is no longer constrained by the delivery catheter 782 and/or the delivery sheath, releasing the valve 700 into the atrium allows the valve 700 to transition from a compressed configuration to an expanded configuration. The control device 770 can then be manipulated or steered to seat and/or deploy the valve 700 into the annulus of the native heart valve, as described in detail above.

The embodiment shown in FIG. 22 includes a support 779 that is coupled to a supra-annular region 720 of the valve 700 (or a valve frame 710 thereof). As described above, the support 779 is configured to provide support to one or more portions of the valve 700 during deployment and/or is configured to facilitate the deployment and/or seating of the valve 700 in the annulus, as described in further detail herein. The support 779 can be similar to and/or substantially the same as the supports 179, 379, 479, 579, and/or 679 described above. For example, the support 779 can be and/or can include one or more tethers, sutures, cables, rods, tensile members, tubes, catheters, hypotubes, and/or the like or combinations thereof.

The support 779 is configured to extend through the lumen of the delivery catheter 782 and/or delivery sheath (not shown) and outside of the control device 770. A proximal end of the support 779 is proximal to and/or outside of the delivery catheter 782, thereby allowing a user to manipulate the support 779. A distal end of the support 779 is removably coupleable to and/or is otherwise configured to selectively engage the supra-annular region 720 of the valve frame 710. More particularly, the support 779 is coupled to an attachment point 746 in a position along the supra-annular region 720 of the valve frame 710 that is at or near a free wall side of the valve 700. For example, the prosthetic valve 700 can be a prosthetic tricuspid valve and can be configured for side delivery through the IVC into the right atrium. As the valve 700 is released into the atrium, a first side of the valve 700 is in contact with and/or adjacent to a septal wall of the heart (e.g., a "septal side" of the prosthetic valve 700) and a second side of the valve 700 is opposite the first side and the septum of the heart (e.g., a "free wall side" of the prosthetic valve 700). In the embodiment shown in FIG. 22, the septal side of the valve 700 includes a posterior-septal (PS) tab or anchoring element 737 that can engage septal tissue to at least partially stabilize the valve 700. In addition, the supra-annular region 720 of the valve frame 710 includes an attachment point 746 that is, for example, between the flow control component 750 and a lateral edge of the supra-annular region 720 on the free wall side of the prosthetic valve 700. The support 779, in turn, is removably coupled to the attachment point 746 and is configured to support, stabilize, and/or at least partially control the free wall side of the prosthetic valve 700.

While the attachment point 746 is shown in a specific position along the free wall side of the prosthetic valve 700, it should be understood that the attachment point 746 can be at any suitable position along the supra-annular region 720. For example, the attachment point 746 can be in a position along the free wall side of the supra-annular region 720 that is proximal or distal to a centerline of the flow control component 750. In some implementations, the proximal-distal positioning of the attachment point 746 can be based at least in part of the anatomy of the heart into which the valve 700 is being deployed. In some implementations, it may be desirable to include the attachment point 746 at a position that is laterally outward of the connection member 778, as shown in FIG. 22.

In the embodiment shown in FIG. 22, the support 779 is configured to be and/or to include a support formed from a material that can provide a desired rigidity and/or that can define a substantially fixed length without being placed under tension (e.g., as described above with reference to the supports 379, 479, 579, and/or 679). More particularly, the support 779 or at least a portion thereof can be formed from a metal (e.g., stainless steel or the like) or a relatively hard polymer. In some embodiments, the support 779 can be and/or include a support catheter having a desired durometer. In some embodiments, the support 779 can be a cable, a hypotube, and/or any other suitable support. In some implementations, a distal end portion of the support 779 (e.g., catheter, cable, hypotube, etc.) can include a tether that facilitates a removable coupling of the support 779 to the attachment point 746. In some implementations, the distal end portion of the support 779 can be removably coupled to the attachment point 746 in any suitable manner (e.g., via a threaded coupling, ball-and-socket coupling, and/or any other removable coupling).

In some implementations, the support 779 formed as and/or otherwise including a catheter, cable, hypotube, and/or or other relatively rigid or semi-rigid member can provide sufficient rigidity and/or stiffness to allow a user to exert, for example, a distally-directed force on the proximal end portion of the support, which in turn, is at least partially transmitted along the support 779 such that the distal end portion of the support 779 exerts at least a portion of the distally-directed force of the supra-annular region 320 of the valve frame 310. In some implementations, it may be advantageous to include such a support 779 that removably couples to the supra-annular region 720 at or near the free wall side of the prosthetic valve 700 to facilitate seating of the valve 700 into the annulus. More specifically, in some instances, the anatomy of the heart may present challenges to seating the valve 700 in the annulus using only the contact between the connection member 778 (yoke) and the supra-annular region 720 of the valve frame 710. For example, the position of an outlet of the IVC relative to the annulus may restrict or limit a degree of control that may otherwise be associated with deploying the valve 700 using just the control device 770. In some instances, the anatomy of the heart may present challenges with seating the free wall side of the valve 700 into the annulus. Thus, including the support 779 described above with reference to FIG. 22, can allow a user to exert a distally-directed force on the supra-annular region 720 of the valve frame 710 at a position along the free wall side of the valve 700, which can push the free wall side of the prosthetic valve 700 in a direction toward the annulus, thereby facilitating deployment and/or seating of the valve 700 in the annulus.

Figure 23:
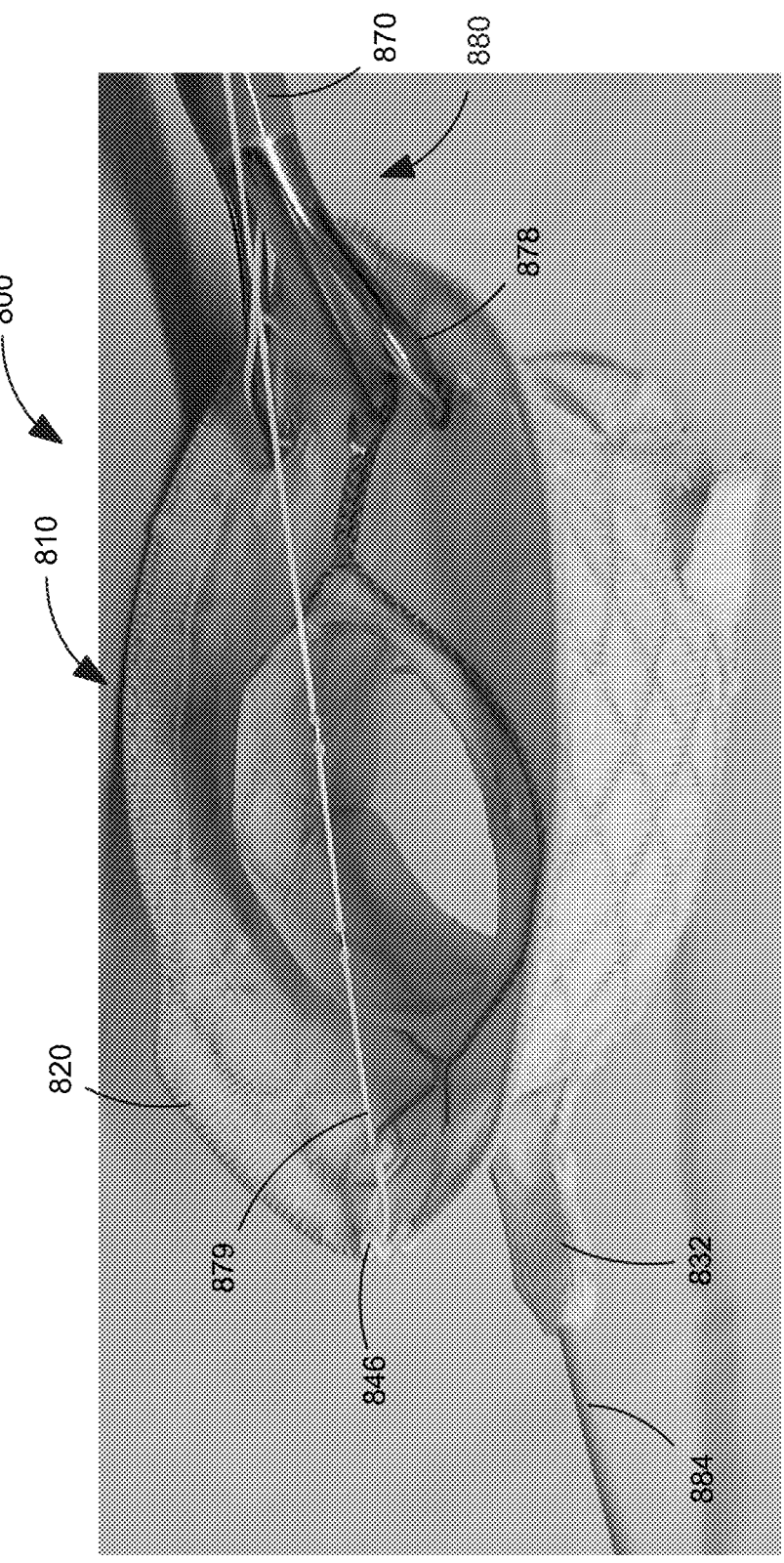
FIG. 23 is a top perspective view of a side-deliverable
transcatheter prosthetic valve coupled to a delivery system
(or portions thereof) used to deliver and deploy the pros-
thetic valve into an annulus of a native heart valve, accord-
ing to an embodiment.
Figure 24:
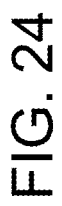
FIGS. 24 and 25 are side views of the prosthetic valve and
the delivery system (or portions thereof) showing a distal
portion or a supra-annular region of the valve in a first state
and a second state, respectively.
Figure 25:
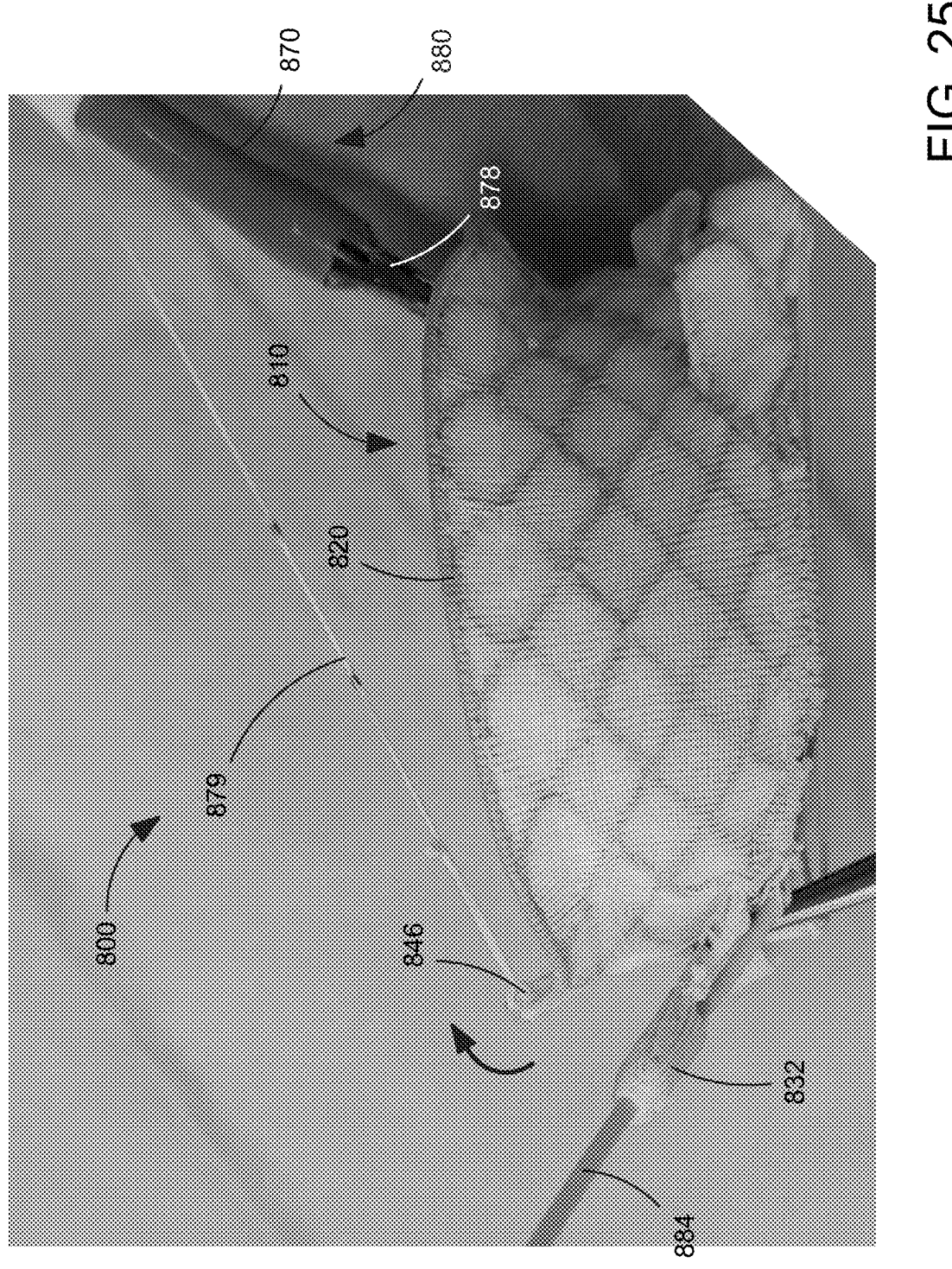

FIGS. 23-25 are various views of a prosthetic valve 800 coupled to a delivery/deployment system 880 having a distal supra-annular support 879, according to another embodiment. The valve 800 can be similar to and/or substantially the same as any of the valves described herein (e.g., the valve 100, 200, 300, 400, 500, 600, and/or 700). Similarly, the delivery/deployment system 880 can be similar to and/or substantially the same as any of the delivery deployment systems described herein (e.g., the delivery/deployment system 180, 380, 480, 580, 680, and/or 780). Thus, the valve 800 (or at least aspects thereof) and the delivery/deployment system 880 (or at least aspects thereof) are not described in further detail herein.

As described above, a control device 870 can include a connection member 878 disposed at a distal end of a control catheter. The connection member 878 is removably coupled to a supra-annular region 820 of the valve 800 (or a valve frame 810 thereof). The coupling, engagement, and/or contact of the connection member 878 and the supra-annular region 820 enables the control device 870 to advance the valve 800 along a guidewire catheter 884 (and/or guidewire) and through a delivery catheter and/or delivery sheath (not shown) and into the atrium of the heart. The delivery catheter and optionally, the delivery sheath, can remain in a substantially fixed position relative to the atrium, or the IVC through which the delivery catheter extends, while a distal end of the control device 870 and the valve 800 are advanced along the guidewire catheter 884 in a distal direction relative to (e.g., away from) the delivery catheter toward the annulus. Because the valve 800 is no longer constrained by the delivery catheter and/or the delivery sheath, releasing the valve 800 into the atrium allows the valve 800 to transition from a compressed configuration to an expanded configuration. The control device 870 can then be manipulated or steered to seat and/or deploy the valve 800 into the annulus of the native heart valve, as described in detail above.

The control device 870 can be manipulated or steered to place the valve 800 (in the expanded configuration) at a desired deployment angle in which a distal anchoring element 832 is positioned below the annulus and near, adjacent, and/or at least partially in, for example, a ventricular outflow tract (e.g., the RVOT). At the deployment angle, a supra-annular region 820 of the valve frame 810 and a least a proximal portion of a subannular region 830 of the valve frame 810 remain in the atrium. In some implementations, a distal surface of a transannular region of the valve frame 810 can be placed in contact with native tissue forming a distal surface or wall of the annulus. As described above with reference to the valve 200, the guidewire catheter 884 extending through and below a portion of the valve 800 and out of the distal anchoring element 832 can provide support to at least a portion of the valve 800 during deployment.

The embodiment shown in FIGS. 23-25 also includes a distal supra-annular support 879 that is removably/releasably coupled to a distal supra-annular region 820 of the valve 800 (or a valve frame 810 thereof). As described above, the support 879 can be configured to support and/or to actuate one or more portions of the valve 800 during deployment. The support 879 can be similar to and/or substantially the same as the support 179, 379, 479, 579, and/or 679 described above. More specifically, the support 879 shown in FIGS. 23-25 is a tether that is removably/releasably coupled to a distal portion of the supra-annular region 820 of the valve 800 or valve frame 810 thereof (also referred to herein as an "atrial distal cuff"). As described above, in some implementations, the support 879 can be configured to transition to a support configuration in response to being placed under tension to provide a desired amount of rigidity and/or support to the atrial distal cuff. In addition, the support 879 can include radiopaque markers allowing the support to be visualized during image-guided procedures such as fluoroscopy.

The support 879 is configured to extend through the lumen of the delivery catheter and/or delivery sheath (not shown) and outside of the control device 870. A proximal end of each support 879 is proximal to and/or outside of the delivery catheter, thereby allowing a user to manipulate the support 879. A distal end of the support 879 is removably coupleable to and/or is otherwise configured to selectively engage an attachment point 846 at or along the atrial distal cuff. More specifically, the attachment point 846 can be attached to an outer wire loop of the supra-annular region 820 of the valve frame 810 (e.g., similar to or substantially the same as the outer loop 221 of the supra-annular member 220 (or region) shown in FIG. 9). In the embodiment shown in FIGS. 23-25, the attachment point 846 is a suture through which at least a portion of the support 879 is looped or wound. In addition, the supra-annular region 820 of the valve frame 810 defines an opening or hole through which a portion of the support 879 can extend, as described above with reference to the support 479. For example, the opening and/or hole is proximal to the attachment point 846 (e.g., along a drum of the supra-annular region 820) allowing a distal portion of the support 879 to extend therethrough. Although not shown, the end of the support 879 forms a loop allowing it to be disposed about or around the guidewire catheter 884 to secure and/or anchor the distal end of the support 879, as described above with reference to the support 479.

The support 879 shown in FIGS. 23-25 is configured to actuate and/or transition at least a portion of the atrial distal cuff between two or more configurations and/or states, as described in further detail herein. For example, FIG. 24 is a side view of the valve 800 and delivery/deployment system 880 showing the atrial distal cuff in a first or unactuated state (the support 879 is shown in tension for illustration purposes, but is not under sufficient tension to actuate the atrial distal cuff). As described above with reference to the valve 100, the atrial distal cuff can be sized and shaped to substantially correspond to the atrial floor distal to the annulus. However, because the process of seating a side-deliverable valve includes inserting the distal subannular portion of the valve 800 into the ventricle and then pivoting the proximal end portion of the valve 800 into the annulus, the shape and size of the atrial distal cuff may, in some instances, push the distal portion of the valve 800 away from the distal annular wall, thereby resisting the process of deploying the valve 800 into the annulus.

Accordingly, as shown in FIG. 25, the support 879 can be transitioned from the first state to a second state and/or can otherwise be placed under sufficient tension to transition the atrial distal cuff from the first or unactuated state (FIG. 24) to a second or actuated state (FIG. 25). Said another way, a proximally directed force can be exerted on the support 879 to actuate the atrial distal cuff. For example, as indicated by the arrow in FIG. 25, the support 879 can be configured to exert a force on or at the attachment point that is operable to actuate at least a part of the atrial distal cuff to facilitate the process of seating the valve 800 by pulling, actuating, and/or otherwise acting on the atrial distal cuff to move, bend, flex, and/or transition the atrial distal cuff in the proximal direction away from the atrial floor or atrial tissue defining or surrounding the annulus. Accordingly, transitioning or actuating the atrial distal cuff in such a manner can reduce the contact between the atrial distal cuff and the atrial tissue that may otherwise resist the pivoting motion associated with seating the valve 800 in the annulus, as described above with reference to the valve 100 and support 179.

FIG. 26 is a flowchart illustrating a method 10 of delivering and deploying a side-deliverable transcatheter prosthetic valve into an annulus of a native valve according to an embodiment. The side-deliverable transcatheter prosthetic valve can be similar to and/or substantially the same as any of the prosthetic valves described herein. For example, the prosthetic valve can include an outer support frame and an (inner) flow control component that is mounted in and/or to the outer support frame. The outer support frame can include, for example, a supra-annular member or region, a subannular member or region, and a transannular member or region coupled therebetween. The flow control component is mounted to the outer support frame such that is extends through a portion of the transannular member or region, as described above with reference to the valve 100 and/or 200.

The method 10 includes removably coupling a control device to a proximal supra-annular portion of the prosthetic valve, at 11. For example, in some embodiments, the supra-annular member can include a proximal attachment member or the like that can be used to temporarily couple the delivery/deployment system to the valve, as described above with reference to the valve 200 shown in FIGS. 7-16. For example, the delivery/deployment system can include a control device or the like that can include a control catheter and a connection member coupled to the distal end of the control catheter. The connection member can be removably coupleable to the attachment member of the valve via one or more tethers and/or the like, as described above with reference to the valve 200.

A supra-annular support of the delivery/deployment system is removably coupled to a supra-annular portion of the prosthetic valve, at 12. The supra-annular support can be any suitable shape, size, and/or configuration. For example, the supra-annular support can be similar to or substantially the same as any of the supra-annular supports 179, 379, 479, 579, 679, 779, and/or 879 described in detail above. In some embodiments, for example, the supra-annular support ("support") can be one or more tethers, tensile members, rods, cables, connectors, etc. configured to removably couple to an attachment point or the like at or along a supra-annular portion of the valve (e.g., a supra-annular region of a valve frame). For example, the support can be and/or can include a tether that is removably coupled to and/or otherwise engaged with an attachment point at a distal supra-annular portion of the valve, as described above with reference to the supports 379, 479, 579, and/or 879. In some embodiments, the support can be and/or can include a pair of supports (e.g., tethers) that are distal to and laterally outward of a connection member of the control device, as described above with reference to the "lateral" supports 679 shown in FIG. 21. For example, the supports can be removably coupled to a portion of the supra-annular portion of the valve at or near the flow control component. In some embodiments, the support can be and/or can include a support catheter that is removably coupled to and/or otherwise engaged with an attachment point that is distal to and laterally outward of the connection member of the control device, as described above with reference to the support 779. In such embodiments, the position of the attachment point along the supra-annular portion of the prosthetic valve can be at or near a free wall side of the prosthetic valve (e.g., a side of the valve that is opposite or not in contact with a septal wall of the heart). In some embodiments, multiple supra-annular supports having any combination of arrangements, configurations, etc. can be used and coupled to the supra-annular region of the valve frame in one or more positions that can support and/or stabilize the valve during deployment into the native annulus.

The control device and the prosthetic valve in a compressed configuration are advanced through a lumen of a delivery catheter to place a distal end portion of the control device and the prosthetic valve into a chamber of the heart, at 13. As described above with reference to the valve 100 and/or 200, the prosthetic valve can be placed into the delivery configuration and loaded into the lumen of the delivery catheter and/or delivery sheath. In some instances, placing the valve into the delivery configuration can include, for example, folding the valve in a lateral direction or along a lateral axis and compressing the valve in an axial or blood flow direction or along a central axis of the valve. In some instances, the control device (or connection member thereof) is removably coupled to the proximal supra-annular portion of the valve prior to being advanced through the lumen of the delivery catheter. As such, the control device can be used to advance the prosthetic valve in the compressed and/or delivery configuration through the lumen of the delivery catheter and into the chamber of the heart. In some instances, the chamber of the heart can be an atrium of the heart. Moreover, the prosthetic valve can be allowed to transition from the compressed configuration to the expanded configuration when the valve is released from the delivery catheter and/or delivery sheath and disposed in the atrium.

The supra-annular support is transitioned from a first state to a second state, at 14. For example, after the prosthetic valve is released from the delivery catheter and/or delivery sheath and allowed to expand to the expanded and/or deployment configuration, a user can manipulate the supra-annular support to transition the support from the first state to the second state. In some implementations, the support can be one or more tethers that can be transitioned from the first state to the second state in response to a proximally directed force exerted by a user on a proximal end portion of the support. In this manner, the proximally directed force can place at least a portion of the support in tension, thereby forming a substantially rigid or substantially fixed-length connection between a distal end of the delivery sheath (from which the support extends) and the attachment portion at or along the distal supra-annular portion of the valve. In some implementations, the support can be one or more tethers that can be transitioned from the first state to the second state in response to the proximally directed force, which in turn, can actuate, reconfigure, and/or otherwise transition one or more portions of the supra-annular region of the valve or valve frame (e.g., an atrial distal cuff). For example, the support can be configured to actuate the atrial distal cuff to move, bend, flex, and/or otherwise transition the atrial distal cuff in a proximal direction (e.g., away from atrial tissue defining and/or surrounding the annulus).

The prosthetic valve is seated in the native annulus while the supra-annular support is in the second state, at 15. The support in the second or support state or configuration can stabilize at least a portion of the valve, which can provide increased control of the valve when moving and/or positioning the valve into the annulus via the control device. In addition, the support can be in a substantially rigid and/or substantially fixed-length configuration during deployment, which can reduce a likelihood of the distal supra-annular portion of the valve dropping into the annulus during deployment, can reduce and/or limit undesirable motion of the valve relative to the delivery/deployment system, can reduce and/or limit undesirable lateral or rotational motion of the valve relative to an annular plane of the native valve, and/or can reduce and/or limit undesirable motion of at least a portion of the delivery/deployment system as a proximal portion of the valve is being pushed or pivoted into the annulus, as described in detail above with reference to the supports 179, 379, 479, 579, 679, 779, and/or 879.

After seating the valve, each of the control device and the supra-annular support is decoupled from the prosthetic valve, at 16. For example, in some implementations, control device can be removably coupled to the proximal portion of the valve via one or more tethers that are "looped" through or around portions of the valve such that each of the proximal and distal ends of the tethers and/or are disposed outside the body. In this manner, a change in force exerted on each end of a tether can be operable to actuate the tether, the control device, and/or a portion of the valve, while a proximally directed force exerted on one of the proximal end or the distal end can be operable to decouple the tether from the valve and withdraw the tether into and/or through the control device. In some implementations, the supra-annular support can be removably coupled to an attachment point or the like at or along the distal supra-annular portion of the valve in a substantially similar manner (e.g., an optional configuration of the support 379).

In other embodiments, a proximal end portion of the support can be proximal to the delivery catheter and/or sheath and disposed outside the body (allowing a user to manipulate the support), while a distal end portion of the support is removably coupled to and/or otherwise removably engaged with the distal supra-annular portion of the valve, a guidewire, a guidewire catheter, and/or the like. For example, the supra-annular portion of the valve can define or form an opening, hole, waypoint, passthrough, etc. configured to allow a distal portion of the support to extend therethrough. In such embodiments, the distal end of the support can include a loop or ring that can be disposed on or about the guidewire catheter (or other component, feature, etc. external to the valve) to secure or anchor the distal end of the support, as described in detail above with reference to the supports 479 and/or 879. In this manner, retracting the guidewire catheter (or other component, feature, etc.) from the distal anchoring element and/or the valve in general, releases the distal end of the support and allows the support to be retracted through the attachment point (e.g., opening, etc.) and into the delivery sheath. Accordingly, the delivery/deployment system can be decoupled from the valve and removed from the patient, as described in detail above with reference to the delivery/deployment systems 180, 280, 380, 480, 580, 680, 780, and/or 880.

While various embodiments have been described above, it should be understood that they have been presented by way of example only, and not limitation. Likewise, it should be understood that the specific terminology used herein is for the purpose of describing particular embodiments and/or features or components thereof and is not intended to be limiting. Various modifications, changes, and/or variations in form and/or detail may be made without departing from the scope of the disclosure and/or without altering the function and/or advantages thereof unless expressly stated otherwise. Functionally equivalent embodiments, implementations, and/or methods, in addition to those enumerated herein, will be apparent to those skilled in the art from the foregoing descriptions and are intended to fall within the scope of the disclosure.

Where schematics, embodiments, and/or implementations described above indicate certain components arranged in certain orientations or positions, the arrangement of components may be modified. Although various embodiments have been described as having particular features and/or combinations of components, other embodiments are possible having a combination of any features and/or components from any of embodiments described herein, except mutually exclusive combinations. The embodiments described herein can include various combinations and/or sub-combinations of the functions, components, and/or features of the different embodiments described.

Where methods described above indicate certain events occurring in certain order, the ordering of certain events may be modified. Additionally, certain of the events may be performed concurrently in a parallel process when possible, as well as performed sequentially as described above. While methods have been described as having particular steps and/or combinations of steps, other methods are possible having a combination of any steps from any of methods described herein, except mutually exclusive combinations and/or unless the context clearly states otherwise.

What is claimed:

1. A delivery system for delivering and deploying a side-deliverable prosthetic heart valve that includes a transannular member configured to extend through an annulus of a native heart valve, a supra-annular member coupled to an upper edge of the transannular member, and a subannular member coupled to a lower edge of the transannular member, the delivery system comprising:

a delivery sheath;

a control device movable through a lumen of the delivery sheath, the control device including a control catheter and a connection member coupled to a distal end of the control catheter, the connection member configured to removably couple to the prosthetic valve at a proximal position along the supra-annular member of the prosthetic valve, the control device operable to advance the prosthetic valve in a compressed configuration through the lumen of the delivery sheath and into a chamber of a heart and deploy the prosthetic valve in an expanded configuration from the chamber of the heart into the annulus of the native heart valve; and at least one supra-annular support movable through the lumen of the delivery sheath and outside of the control catheter, the at least one supra-annular support being separate from the control device and configured to removably couple to an attachment point at a distal position along the supra-annular member of the prosthetic valve, the at least one supra-annular support configured to stabilize or actuate at least a distal supra-annular portion of the prosthetic valve relative to an annular plane of the native heart valve during deployment.

2. The delivery system of claim 1, wherein the connection member forms a yoke configured to contact the supra-annular portion of the prosthetic valve.

3. The delivery system of claim 2, wherein the yoke has a first arm and a second arm arranged in a Y-shape, the at least one supra-annular support is configured to removably couple to the attachment point along the supra-annular member of the prosthetic valve at a position distal to and laterally outward of one of the first arm of the yoke or the second arm of the yoke.

4. The delivery system of claim 3, wherein the at least one supra-annular support is at least one of a catheter, a cable, or a hypotube having a rigidity sufficient to transmit a distally directed force exerted on a proximal end portion thereof to the supra-annular member of the prosthetic valve operable to push a portion of the prosthetic valve toward the annulus.

5. The delivery system of claim 1, wherein the at least one supra-annular support includes at least one tether that is removably coupleable to the attachment point.

6. The delivery system of claim 5, wherein the at least one tether is configured to transition from a first configuration to a second configuration in response to a proximally directed force exerted on a proximal end portion thereof.

7. The delivery system of claim 6, wherein the at least one tether in the second configuration forms a substantially fixed-length connection between a distal end portion of the delivery sheath and the distal supra-annular portion of the prosthetic valve.

8. The delivery system of claim 1, wherein the prosthetic valve has a valve frame and a flow control component mounted in the valve frame, the valve frame including the supra-annular member, the transannular member, and the subannular member, and the at least one supra-annular support includes at least one tether that is removably coupleable to the attachment point, the attachment point being along a distal portion of the supra-annular member of the valve frame.

9. The delivery system of claim 8, wherein the at least one tether is removably coupleable to the attachment point such that a proximally directed force exerted on a proximal end portion of the at least one tether actuates the distal portion of the supra-annular member of the valve frame.

10. The delivery system of claim 9, wherein the at least one tether actuating the distal portion of the supra-annular member of the valve frame includes moving the distal portion of the supra-annular member of the valve frame in a proximal direction away from native tissue defining or surrounding at least a distal portion of the annulus.

11. The delivery system of claim 1, wherein the subannular member coupled to the lower edge of the transannular member is configured to be disposed in a ventricle of the heart, and the supra-annular member coupled to the upper edge of the transannular member is configured to be maintained in an atrium of the heart.

12. A delivery system for delivering and deploying a side-deliverable prosthetic heart valve that includes a transannular member configured to extend through an annulus of a native heart valve, a supra-annular member coupled to an upper edge of the transannular member, and a subannular member coupled to a lower edge of the transannular member, the delivery system comprising:

a delivery sheath;

a control device movable through a lumen of the delivery sheath, the control device including a control catheter and a connection member coupled to a distal end of the control catheter, the connection member configured to removably couple to a proximal portion of the supra-annular member of the prosthetic valve, the control device operable to advance the prosthetic valve in a compressed configuration through the lumen of the delivery sheath and into a chamber of a heart and deploy the prosthetic valve in an expanded configuration from the chamber of the heart into the annulus of the native heart valve; and a supra-annular support disposed outside of the control catheter and movable through the lumen of the delivery sheath, the supra-annular support being separate from the control catheter and configured to removably couple to an attachment point at or along a distal portion of the supra-annular member of the prosthetic valve, the supra-annular support configured to transition from a first state to a second state when the prosthetic valve is in the expanded configuration, the supra-annular support in the second state forming a substantially fixed-length connection between the delivery sheath and the distal portion of the supra-annular member of the prosthetic valve.

13. The delivery system of claim 12, further comprising:

a delivery catheter including a distal end configured to be advanced through a vasculature of a patient and into the chamber of the heart and a proximal end disposed outside the patient, the delivery sheath being movable through a lumen of the delivery catheter.

14. The delivery system of claim 12, wherein the connection member of the control device is configured to removably couple to the proximal portion of the supra-annular member of the prosthetic valve via a set of tethers.

15. The delivery system of claim 12, wherein the supra-annular support is at least one tether.

16. The delivery system of claim 12, wherein the attachment point is at least one suture.

17. The delivery system of claim 12, wherein the prosthetic valve has a valve frame and a flow control component mounted in the valve frame, the valve frame including the supra-annular member, the transannular member, and the subannular member, and the attachment point is at least one suture attached to the distal portion of the supra-annular member of the valve frame.

18. The delivery system of claim 17, wherein the supra-annular support is configured to removably couple to the attachment point such that a distal end portion of the supra-annular support extends through an opening at or along the distal portion of the supra-annular member of the valve frame.

19. The delivery system of claim 18, wherein the distal end of the supra-annular support forms a loop configured to be disposed about a guidewire catheter removably coupled to the subannular member of the valve frame.

20. The delivery system of claim 19, wherein deploying the prosthetic valve in the expanded configuration from the chamber of the heart into the native annulus is such that a distal wall of the prosthetic valve is placed in contact with native tissue forming at least a portion of the annulus, and the distal portion of the supra-annular support is configured to be secured relative to the attachment point in response to the contact between the distal wall of the valve and the native tissue forming at least the portion of the annulus.

21. The delivery system of claim 12, wherein the subannular member coupled to the lower edge of the transannular member is configured to be disposed in a ventricle of the heart, and the supra-annular member coupled to the upper edge of the transannular member is configured to be maintained in an atrium of the heart.

22. A method of delivering and deploying a side-deliverable prosthetic valve into a native valve annulus of a heart, the prosthetic valve including a transannular member configured to extend through the native valve annulus, a supra-annular member coupled to an upper edge of the transannular member, and a subannular member coupled to a lower edge of the transannular member, the method comprising:

removably coupling a connection member of a control device to a proximal portion of the supra-annular member of the prosthetic valve;

removably coupling a supra-annular support to an attachment point along a distal portion of the supra-annular member of the prosthetic valve, the supra-annular support being separate from and disposed outside of a control catheter of the control device and movable through a lumen of a delivery sheath;

advancing the control device and the prosthetic valve in a compressed configuration through a lumen of a delivery catheter to place a distal end portion of the control device and the prosthetic valve into a chamber of the heart, the prosthetic valve in an expanded configuration when in the chamber of the heart;

transitioning the supra-annular support from a first state to a second state to form a substantially rigid connection between a distal end of the delivery catheter and the distal portion of the supra-annular member;

seating the prosthetic valve in the native valve annulus while the supra-annular support is in the second state; and decoupling each of the connection member of the control device and the supra-annular support from the supra-annular member of the prosthetic valve after the seating.

23. The method of claim 22, wherein the supra-annular support includes at least a support catheter.

24. The method of claim 23, wherein the transitioning the supra-annular support from the first state to the second state includes exerting a distally directed force on a proximal end portion of the support catheter, and the seating the prosthetic valve in the native valve annulus while the supra-annular support is in the second state includes transmitting, via the support catheter, at least a portion of the distally directed force to the distal portion of the supra-annular member of the prosthetic valve, thereby pushing at least a distal portion of the prosthetic valve into the native valve annulus.

25. The method of claim 23, wherein the seating the prosthetic valve in the native annulus includes seating the prosthetic valve such that the subannular member of the prosthetic valve is disposed in a ventricle of the heart, the transannular member of the prosthetic valve extends through the native valve annulus, and the supra-annular member is maintained in an atrium of the heart.

26. The method of claim 22, wherein the supra-annular support is at least one tether.

27. The method of claim 26, wherein a proximal end of the at least one tether is proximal to the delivery catheter, the method further comprising:

exerting a proximally directed force on the proximal end of the at least one tether to increase a tension along the at least one tether, the increased tension along the at least one tether operable to transition the at least one tether from the first state to the second state.

28. The method of claim 27, further comprising:

actuating the distal portion of the supra-annular member in response to the proximally directed force exerted on the proximal end of the at least one tether, the actuating operable to move the distal portion of the supra-annular member in a proximal direction away from native tissue defining or surrounding at least a distal portion of the native valve annulus.

29. The method of claim 26, wherein the removably coupling the at least one tether to the attachment point is such that a distal end portion of the at least one tether extends through an opening along a distal portion of the prosthetic valve to allow a loop at a distal end of the at least one tether to be disposed about a guidewire catheter that is removably coupled to the subannular member of the prosthetic valve.

30. The method of claim 29, wherein after the seating the prosthetic valve in the native valve annulus the method further comprising:

moving the guidewire catheter in a proximal direction such that a distal end of the guidewire catheter is at least partially disposed in the delivery catheter and decoupled from the subannular member of the prosthetic valve; and releasing the loop at the distal end of the at least one tether from the guidewire catheter in response the guidewire catheter moving in the proximal direction.

* * * * *